(12) United States Patent
Kossmann et al.

(10) Patent No.: US 6,570,065 B1
(45) Date of Patent: May 27, 2003

(54) NUCLEIC ACID MOLECULES ENCODING ALTERNANSUCRASE

(75) Inventors: Jens Kossmann, Berlin (DE); Thomas Welsh, Berlin (DE); Martin Quanz, Berlin (DE); Karola Knuth, Berlin (DE)

(73) Assignee: Max-Planck-Gesellschaft zur Forderung der Wissenschaften e.v., Berlin (DE)

( * ) Notice: Subject to any disclaimer, the term of this patent is extended or adjusted under 35 U.S.C. 154(b) by 0 days.

(21) Appl. No.: 09/499,203

(22) Filed: Feb. 8, 2000

(30) Foreign Application Priority Data

Feb. 8, 1999 (DE) .......................................... 199 05 069

(51) Int. Cl.$^7$ ......................... C12N 15/82; C12N 15/31; C12N 15/54; C12N 15/70; A01H 5/00
(52) U.S. Cl. ....................... 800/284; 800/278; 800/288; 800/305; 800/306; 800/312; 800/314; 800/317.2; 800/320; 800/320.1; 800/320.2; 800/320.3; 800/322; 435/69.1; 435/70.1; 435/71.1; 435/101; 435/193; 435/252.3; 435/252.33; 435/320.1; 435/419; 435/468; 435/471; 435/476; 536/23.2; 536/23.7
(58) Field of Search ................................ 800/284, 288, 800/278, 305, 306, 312, 314, 317.2, 317.4, 320, 320.1, 320.2, 320.3, 322; 435/101, 193, 419, 468, 320.1, 69.1, 252.3, 252.33, 471, 476, 70.1, 71.1; 536/23.2, 23.7

(56) References Cited

U.S. PATENT DOCUMENTS 6,127,602 A * 10/2000 Nichols ...................... 800/284

OTHER PUBLICATIONS

Hanada et al. Infection and Immunity 57(7) : 2079–2085, Jul. 1989.*
Shiroza et al. J. Bacteriology 169(9) : 4263–4270, Sep. 1987.*
Fuchs, A. Biochem. Soc. Trans. 19 : 555–560, 1991.*
Sneekers et al. Biochem. Soc. Trans. 19 : 565–569, 1991.*
Turk et al. New Phytol. 136 (1) : 29–38, 1997.*
Carbohydrate Polymers (1992) 19: 249–52, Cote, Low–viscosity . . . .
Carbohydrate Research (1979) 74: 41–62, Seymour et al, "Structural . . . ".
Sciences des Aliments (1991) 11: 465–76, Pelenc et al, "Enzymatic . . . ".
Applied and Environmental Microbiology (Mar. 1995) 1120–23, Zahnley et al, vol. 61 (3).
Annals New York Academy of Sciences : 717–722, Lopez–Munguia et al, "Production . . . " vol. 613 (1990).
Enzyme Microb. Technol. (Aug. 1994) 16: 659–64, Kim et al, Production . . . .
Journal of General Microbiology (1985) 131: 3347–53, Tsumori et al.
Journal of General Microbiology (1989) 135: 2055–63, Mukasa et al.
Eur. J. Biochem. (1994) 226: 633–39, Biely et al, "Purification . . . ".
Carbohydrate Research (1982) 101: 57–74, Cote et al, "Isolation and partial . . . ".
Journal of Industrial Microbiology & Biotechnology (1997) 18: 278–83, Leathers et al.
Enzyme Microb. Technol. (1993) 15 (Jan.):77–85, Lopez–Munguia et al.
Abstract from GenBank, Accession No. AJ250173.
FEMS Microbiol Lett 182 (1) (2000) 81–85, ARguello–Morales et al "Sequence analysis of the gene encoding alternansucrase, a sucrose . . . ".

* cited by examiner

Primary Examiner—David T. Fox
(74) Attorney, Agent, or Firm—Birch, Stewart, Kolasch & Birch, LLP

(57) ABSTRACT

Nucleic acid molecules encoding an alternansucrase are provided. Moreover, vectors, host cells and plant cells transformed by the herein-described nucleic acid molecules and plants containing them are provided. Furthermore, methods are described for preparing transgenic plants which synthesize the carbohydrate alternan, because of the insertion of nucleic acid molecules encoding an alternansucrase. Moreover, methods for preparing alternan and products resulting from them are provided.

17 Claims, 12 Drawing Sheets

NUCLEIC ACID MOLECULES ENCODING ALTERNANSUCRASE

FIELD OF THE INVENTION

The present invention relates to nucleic acid molecules encoding an alternansucrase. Moreover, this invention relates to vectors, host cells and plant cells transformed with the herein-described nucleic acid molecules, and plants containing said cells. Moreover, methods for preparing transgenic plants which due to the insertion of DNA molecules encoding an alternansucrase, synthesize the carbohydrate alternan, are described. Furthermore, methods for preparing alternan are described.

Prior art documents, the disclosure content of which is included into the present application by reference thereto, are cited hereinafter.

Alternan is a polysaccharide composed of glucose units. The glucose units are linked to each other via α-1,3- and α-1,6-glycosidic bonds, and said two types of bonds predominantly appear alternatingly. However, alternan is not a linear polysaccharide, but may contain branches (Seymour et al., Carbohydrate Research 74, (1979), 41–62). Because of its physico-chemical properties, the possibilities of application of alternan both in the pharmaceutical industry, for instance as a carrier of pharmaceutically active ingredients and as an additive in the textile, cosmetics and food industry have been discussed (Lopez-Munguia et al., Enzyme Microb. Technol. 15, (1993), 77–85; Leathers et al., Journal of Industrial Microbiology & Biotechnology 18, (1997), 278–283). Moreover, it can be used as a substitute for gum arabic (Coté, Carbohydrate Polymers 19, (1992), 249–252).

Industry has a high interest in biotechnological methods for preparing oligosaccharides and polysaccharides, and in particular alternan which is hardly or not at all accessible to classical organic synthesis. Compared to the classical approach of organic synthesis chemistry, biotechnological processes offer advantages. For instance, enzymatically catalyzed reactions as a rule show much higher specificities (regio specificity, stereo specificity) and higher reaction speeds, proceed under milder reaction conditions and lead to higher yields. These factors are of outstanding importance in the preparation of new oligosaccharides and polysaccharides.

Alternan is prepared enzymatically with the use of enzymes possessing the biological activity of alternansucrases. Alternansucrases belong to the group of glucosyltransferases, which, starting from saccharose, are able to catalyze the formation of alternan and fructose. So far, alternansucrases have only been found in the bacterium *Streptococcus mutans* (Mukasa et al. (J. Gen. Microbiol. 135 (1989), 2055–2063); Tsumori et al. (J. Gen. Microbiol. 131 (1985), 3347–3353)) and in specific strains of the gram positive bacterium *Leuconostoc mesenteroides* where they are, as a rule, present together with other polysaccharide-forming enzymes, such as for instance dextran-forming dextransucrases, or together with polysaccharide-degrading enzymes, such as alternanases. Hence, the naturally occurring strains also produce dextran in addition to alternan.

So far, alternan has been prepared in a cell-free system using partially purified proteins or by fermentation using alternansucrase-producing strains of *Leuconostoc mesenteroides*.

Various purification methods for the purification of alternansucrases have been described (Lopez-Munguia et al., Enzyme Microb. Technol. 15 (1993), 77–85; Lopez-Munguia et al., Annals New York Academy of Sciences 613 (1990), 717–722; Coté and Robyt, Carbohydrate Research 101 (1982), 57–74). These methods are complex and relatively costly, and, as a rule, lead to low protein yields (Leathers et al., Journal of Industrial Microbiology & Biotechnology 18 (1997), 278–283). None of these methods allows highly pure alternansucrase protein to be produced, and therefore sequencing of the protein and the isolation of the corresponding DNA sequences have not been successful so far. If the alternansucrase protein purified according to these methods is used for in vitro preparation of alternan, then the dextransucrase protein residues contained in the alternansucrase preparation produce dextran impurities in the alternan produced. The separation of alternan and dextran is relatively time-consuming and costly (Leathers et al., Journal of Industrial Microbiology & Biotechnology 18 (1997), 278–283). Another disadvantage of the dextransucrase protein impurities contained in the enzyme preparation of alternansucrase protein is the fact that a part of the saccharose substrate is converted into dextran and not into alternan, which results in a reduction of the alternan yield.

The fermentative preparation by means of Leuconostoc also leads to the formation of product mixtures of alternan and dextran. In order to increase the amount of alternansucrase from Leuconostoc strains, mutants have been isolated, such as the mutant NRRL B-21138, which secrete the alternansucrase and lead to a higher proportion of the amount of alternansucrase formed relative to dextransucrase. However, if such mutants are fermented with sucrose, the alternan obtained continues to show dextran impurities (Leathers et al., Journal of Industrial Microbiology & Biotechnology 18 (1997), 278–283).

As can be seen from the prior art discussed above, it has not been possible to provide highly purified alternansucrase protein so far.

Hence, the present invention addresses the problem of providing means and methods allowing alternan to be prepared in a time-saving and inexpensive manner.

This problem is solved by the provision of the embodiments characterized in the patent claims.

SUMMARY OF THE INVENTION

Consequently, the present invention relates to a nucleic acid molecule encoding a protein possessing the biological activity of an alternansucrase selected from the group consisting of (a) nucleic acid molecules encoding at least the mature form of a protein which comprises the amino acid sequence indicated in Seq. ID No. 2 or the amino acid sequence encoded by the cDNA contained in plasmid DSM 12666;

(b) nucleic acid molecules comprising the nucleotide sequence indicated in Seq. ID No. 1 or the nucleotide sequence of the cDNA contained in plasmid DSM 12666 or a corresponding ribonucleotide sequence;

(c) nucleic acid molecules encoding a protein, the amino acid sequence of which has a homology of at least 40% to the amino acid sequence indicated in Seq. ID No. 2;

(d) nucleic acid molecules, one strand of which hybridizes with the nucleic acid molecules as defined in (a) or (b);

(e) nucleic acid molecules comprising a nucleotide sequence encoding a biologically active fragment of the protein which is encoded by any one of the nucleic acid molecules as defined in (a), (b), (c) or (d); and (f) nucleic acid molecules, the nucleotide sequence of which deviates because of the degeneration of the genetic code from the sequence of the nucleic acid molecules as defined in (a), (b), (c), (d) or (e).

Consequently, the present invention relates to nucleic acid molecules encoding proteins possessing the biological activity of an alternansucrase, said molecules preferably encoding proteins comprising the amino acid sequence indicated in Seq. ID No.2.

An enzyme possessing the enzymatic or biological activity of an alternansucrase (E.C. 2.4.1.140) is understood to mean an enzyme which is able to catalyze the conversion of saccharose into alternan and fructose. This conversion may occur both in the presence and absence of external acceptors (for instance maltose, isomaltose, isomaltotriose etc.). In the absence of external acceptors, alternansucrases starting from saccharose catalyze the release of fructose and high molecular alternan, a polysaccharide composed of glucose units, the backbone of which consists of glucose units predominantly connected to each other alternatingly by α-1,3- and α-1,6-glycosidic bonds. Concerning the percentage of α-1,3- and α-1,6-linked glucose units the literature displays different values. According to Mukasa et al. (J. Gen. Microbiol. 135 (1989), 2055–2063), alternan consists of 76 mol % α-1,3-linked glucose and 24 mol % α-1,6-linked glucose. Tsumori et al. (J. Gen. Microbiol. 131 (1985), 3347–3353) describe alternan as a polyglucan containing 49.1 mol % α-1,6-linked glucose and 33.9 mol % α-1,3-linked glucose with 13.6 mol % terminal glucose and 3.3 mol % α-1,3,6-branched glucose. In the presence of external acceptors, such as maltose, isomaltose, isomaltotriose and methyl-α-D-glucan, alternansucrase can catalyze the synthesis of α-D-glucan chains, in which the glucose residues are predominantly alternatingly connected by α-1,6- and α-1,3-glycosidic bonds, and the synthesis of fructose at these polysaccharide acceptors. Depending on the acceptor used, the products formed have different structures. The enzymatic activity of an alternansucrase can for instance be detected as described by Lopez-Munguia (Annals New York Academy of Sciences 613 (1990), 717–722) or as described in the examples of the present application.

The invention in particular relates to nucleic acid molecules containing the nucleotide sequence indicated under Seq. ID No. 1 or a part thereof, and preferably to molecules, which comprise the coding region indicated in Seq. ID No. 1 or corresponding ribonucleotide sequences.

Moreover, the present invention relates to nucleic acid molecules which encode an alternansucrase and the one strand of which hybridizes with one of the above-described molecules.

The present invention also relates to nucleic acid molecules which encode a protein, which has a homology, that is to say an identity of at least 40%, preferably at least 60%, preferably at least 70%, especially preferably at least 80% and in particular at least 90% to the entire amino acid sequence indicated in Seq. ID No. 2, the protein possessing the biological activity of an alternansucrase.

The present invention also relates to nucleic acid molecules, which encode an alternansucrase and the sequence of which deviates on account of the degeneration of the genetic code from the nucleotide sequences of the above-described nucleic acid molecules.

The invention also relates to nucleic acid molecules possessing a sequence which is complementary to the whole or a part of the above-mentioned sequences.

The nucleic acid sequence indicated in Seq. ID No. 1 for instance encodes an extracellular alternansucrase. Secretion is ensured by a signal sequence which comprises the first approximately 39 N-terminal amino acid groups of the Seq. ID No. 2. In certain circumstances it may be desirable for only the mature protein to be expressed without naturally occurring signal sequences and/or together with other signal sequences. Hence, the above-described nucleic acid molecules encode at least the mature form of a protein possessing the biological activity of an alternansucrase.

Within the present invention the term "hybridization" means hybridization under conventional hybridization conditions, preferably under stringent conditions, as for instance described in Sambrook et al., Molecular Cloning, A Laboratory Manual, $2^{nd}$ edition (1989) Cold Spring Harbour Laboratory Press, Cold Spring Harbour, N.Y. Within an especially preferred meaning the term "hybridization" means that hybridization occurs under the following conditions:

Hybridization buffer: 2×SSC; 10×Denhardt solution (Fikoll 400+PEG+BSA; ratio 1:1:1); 0.1% SDS; 5 mM EDTA; 50 mM $Na_2HPO_4$;250 μg/ml of herring sperm DNA; 50 μg/ml of tRNA; or 0.25 M of sodium phosphate buffer, pH 7.2;

1 mM EDTA

7% SDS

Hybridization temperature T=60° C.

Washing buffer: 2×SSC; 0.1% SDS

Washing temperature T=60° C.

Nucleic acid molecules which hybridize with the nucleic acid molecules of the invention can, in principle, encode alternansucrases from any organism expressing such proteins.

Nucleic acid molecules which hybridize with the molecules of the invention can for instance be isolated from genomic libraries of microorganisms. Alternatively, they can be prepared by genetic engineering or chemical synthesis.

Such nucleic acid molecules may be identified and isolated with the use of the molecules of the invention or parts of these molecules or reverse complements of these molecules, for instance by hybridization according to standard methods (see for instance Sambrook et al., 1989, Molecular Cloning. A Laboratory Manual, $2^{nd}$ edition, Cold Spring Harbor Laboratory Press, Cold Spring Harbor, N.Y.). Nucleic acid molecules possessing the same or substantially the same nucleotide sequence as indicated in Seq. ID No. 1 or parts thereof can, for instance, be used as hybridization probes. The fragments used as hybridization probes can also be synthetic fragments which are prepared by usual synthesis techniques, and the sequence of which substantially coincides with that of an inventive nucleic acid molecule.

The molecules hybridizing with the nucleic acid molecules of the invention also comprise fragments, derivatives and allelic variants of the above-described nucleic acid molecules encoding an alternansucrase of the invention. Herein, fragments are understood to mean parts of the nucleic acid molecules which are long enough to encode one of the described proteins, preferably showing the biological activity of an alternansucrase. In this connection, the term derivative means that the sequences of these molecules also differ from the sequences of the above-described nucleic acid molecules in one or more positions and show a high degree of homology to these sequences. In this context, homology means a sequence identity of at least 40%, in particular an identity of at least 60%, preferably more than 80% and particularly preferably more than 90%. Deviations from the above-described nucleic acid molecules may have been produced by deletion, substitution, insertion and/or recombination.

Preferably, the degree of homology is determined by comparing the respective sequence with the nucleotide sequence of the coding region of SEQ ID No.1. When the sequences which are compared do not have the same length, the degree of homology preferably refers to the percentage of nucleotide residues in the shorter sequence which are identical to nucleotide residues in the longer sequence. The degree of homology can be determined conventionally using known computer programs such as the ClustalW program (Thompson et al., Nucleic Acids Research 22 (1994), 4673–4680) distributed by Julie Thompson (Thompson@EMBL-Heidelberg.DE) and Toby Gibson (Gibson@EMBL-Heidelberg.DE) at the European Molecular Biology Laboratory, Meyerhofstrasse 1, D 69117 Heidelberg, Germany. ClustalW can also be downloaded from several websites including IGBMC (Institut de Génétique et de Biologie Moléculaire et Cellulaire, B.P.163, 67404 Illkirch Cedex, France; ftp://ftp-iabmc.u-strasbg.fr/pub/) and EBI (ftp://ftp.ebi.ac.uk/pub/software/) and all sites with mirrors to the EBI (European Bioinformatics Institute, Wellcome Trust Genome Campus, Hinxton, Cambridge CB10 1SD, UK).

When using ClustalW program version 1.8 to determine whether a particular sequence is, for instance, 90% identical to a reference sequence according to the present invention, the settings are set in the following way for DNA sequence alignments:

KTUPLE=2, TOPDIAGS=4, PAIRGAP=5, DNAMATRIX:IUB, GAPOPEN=10, GAPEXT=5, MAXDIV=40, TRANSITIONS: unweighted.

For protein sequence alignments using ClustalW program version 1.8 the settings are the following: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Furthermore, homology means preferably that the encoded protein displays a sequence identity of at least 40%, more preferably of at least 60%, even more preferably of at least 80%, in particular of at least 90% and particularly preferred of at least 95% to the amino acid sequence depicted under SEQ ID NO: 2.

Homology, moreover, means that there is a functional and/or structural equivalence between the corresponding nucleic acid molecules or proteins encoded thereby. Nucleic acid molecules which are homologous to the above-described molecules and represent derivatives of these molecules are, as a rule, variations of these molecules which represent modifications having the same biological function. They may be either naturally occurring variations, for instance sequences from other microorganisms, or mutations, and said mutations may have formed naturally or may have been produced by deliberate mutagenesis. Furthermore, the variations may be synthetically produced sequences. The allelic variants may be naturally occurring variants or synthetically produced variants or variants produced by recombinant DNA techniques.

In a further preferred embodiment the term "derivative" encompasses a nucleic acid molecule coding for a protein which comprises at least one, more preferably at least three, even more preferably at least five, in particular at least ten and particularly preferred at least twenty of the peptide motifs selected from the group consisting of a) MKOQE (SEQ ID NO: 22),
b) KKVPV (SEQ ID NO: 23),
c) KDDEN (SEQ ID NO: 24),
d) IDGNL (SEQ ID NO: 25),
e) YVADS (SEQ ID NO: 26),
f) HLRKN (SEQ ID NO: 27),
g) NENTP (SEQ ID NO: 28),
h) NVDGY (SEQ ID NO: 29),
i) NPDLK (SEQ ID NO: 30),
j) SNDSG (SEQ ID NO: 31),
k) NTFVK (SEQ ID NO: 32),
l) ISGYL (SEQ ID NO: 33),
m) SNAAL (SEQ ID NO: 34),
n) RQYTD (SEQ ID NO: 35),
o) QLYRA (SEQ ID NO: 36),
p) DDKAP (SEQ ID NO: 37),
q) TRQYT (SEQ ID NO: 38),
r) ITFAG (SEQ ID NO: 39),
s) NQYKG (SEQ ID NO: 40),
t) LFLNA (SEQ ID NO: 41),
u) QVSDT (SEQ ID NO: 42),
v) LITLN (SEQ ID NO: 43),
w) GRYVH (SEQ ID NO: 44),
x) TAPYG (SEQ ID NO: 45),
y) VVDYQ (SEQ ID NO: 46),
z) LSGQE (SEQ ID NO: 47).

The proteins encoded by the different variants of the nucleic acid molecules of the invention possess certain characteristics they have in common. These include for instance enzymatic activity, molecular weight, immunological reactivity, conformation, etc., and physical properties, such as for instance the migration behavior in gel electrophoreses, chromatographic behavior, sedimentation coefficients, solubility, spectroscopic properties, stability, pH optimum, temperature optimum etc.

Alternansucrase (E.C. 2.4.1.140) is an enzyme belonging to the group of glucosyltransferases. So far, alternansucrase activity has not been found in plants, but only in the bacterium *Streptococcus mutans* (Mukasa et al. (J. Gen. Microbiol. 135 (1989), 2055–2063); Tsumori et al. (J. Gen. Microbiol. 131 (1985), 3347–3353)) and in specific strains of the bacterium *Leuconostoc mesenteroides*, for instance in NRRL B-1355, NRRL B-1498 and NRRL B-1501. As a rule, these strains contain different glucosyltransferases and secrete dextransucrases apart from alternansucrases if they are allowed to grow on saccharose-containing media. As a rule, these two sucrases possess a high binding affinity to the polysaccharides synthesized by them (Lopez-Munguia et al., Annals New York Academy of Sciences 613 (1990), 717–722) with the result that these polysaccharides must be separated from the protein in the purification of the enzymes from *Leuconostoc mesenteroides* strains grown on saccharose-containing medium (Lopez-Munguia et al., Enzyme Microb. Technol. 15 (1993), 77–85; Leathers et al., Journal of Industrial Microbiology & Biotechnology 18 (1997), 278–283).

In the absence of external acceptors, alternansucrases, starting from saccharose, catalyze the release of fructose and high molecular alternan, a polysaccharide which is composed of glucose units, and the backbone of which consists of glucose units predominantly linked to each other alternatingly by α-1,3- and α-1,6-glycosidic bonds and which according to light scattering measurement data should have a molecular weight of $>10^7$ (Coté, Carbohydrate Polymer 19 (1992), 249–252). To date there has been no report of alternan possessing a terminal fructose residue. Nevertheless, the existence of a terminal fructose unit in alternan can not be completely excluded. Lopez-Munguia et al. (Enzyme Microb. Technol. 15 (1993) 77–85) describe that alternan is resistant to degradation by dextranases. However, it can be degraded by so-called alternanases, whereby ring-shaped oligomers of alternan of different polymerization degree can be produced (Biely et al., Eur. J. Biochem. 226 (1994), 633–639). Ultrasonic treatment of high molecular alternan allows the molecular weight of alternan to be reduced to <$10^6$ (Coté, Carbohydrate Polymers 19 (1992), 249–252). If aqueous solutions of this ultrasonically treated alternan are prepared, then these solutions show rheological properties comparable to those of aqueous solutions of gum arabic. So-called "limit alternan" having a molecular weight of about 3500 can be produced by enzymatic degradation using isomaltodextranase from *Arthrobacter globiformis* (NRRL B-4425) (Cote, Carbohydrate Polymers 19 (1992), 249–252).

In the presence of external acceptors, such as for instance maltose, isomaltose, isomaltotriose and methyl-α-D-glucan, alternansucrase catalyzes at said saccharide acceptors the synthesis of α-D-glucan chains, in which the glucose moieties are predominantly alternatingly linked by α-1,6- and α-1,3 glycosidic bonds, and the synthesis of fructose. Depending on the acceptor used, the resulting products have different structures and a molecular weight which is lower than that of high molecular alternan and a polymerization degree of <15. Because of the polymerization degree, these products are often also referred to as oligoalternans (Pelenc et al., Sciences Des Aliments 11 (1991), 465–476). However, within the framework of the present invention these low molecular products which can be prepared in the presence of external acceptors are also to be referred to as alternan.

In the preparation of oligoalternans by means of partially purified alternansucrase protein, maltose is an acceptor (Lopez-Munguia et al., Enzyme Microb. Technol. 15 (1993), 77–85) producing high oligoalternan yields. Panose (degree of polymerization (d.p.) of 3) is the first acceptor product which is formed starting from maltose through the formation of an α-1,6-glycosidic bond.

In contrast thereto, isomaltose is a less effective acceptor which leads to lower yields of oligoalternan (Lopez-Munguia et al., Enzyme Microb. Technol. 15 (1993), 77–85).

Alternansucrase is relatively stable and has a half life period of 2 days in 50 mM of acetate buffer, pH 5.4 at 40° C. (Lopez-Munguia et al., Enzyme Microb. Technol. 15 (1993), 77–85). The enzyme shows maximum activity at a temperature of 40° C. and a pH value of 5.6 (Lopez-Munguia et al., Enzyme Microb. Technol. 15 (1993), 77–85).

In the absence of the substrate saccharose, alternansucrase catalyzes disproportionation reactions leading to a (partial) rearrangement of alternan. In particular when partially purified alternansucrase preparations containing dextransucrase contaminations were used to prepare oligoalternans, high disproportionation rates were found which lead to a complete rearrangement of oligoalternan (Lopez-Munguia et al., Enzyme Microb. Technol. 15 (1993), 77–85). For the molecular weight of alternansucrase according to SDS PAGE determination, different numerical values can be found: 135 kDa, 145 kDa, 173 kDa and 196 kDa, respectively (Leathers et al., Journal of Industrial Microbiology & Biotechnology 18 (1997), 278–283; Kim & Robyt, Enzyme Microb. Technol. 16 (1994), 659–664; Zhanley & Smith, Applied and Environmental Microbiology 61(3) (1995), 1120–1123).

The enzymatic activity of an alternansucrase can be shown for instance as described in Lopez-Munguia et al. (Annals New York Academy of Sciences 613 (1990), 717–722) or as described in the examples of the present application. One activity unit (1u) can be defined as the amount of enzyme leading to the release of 1 μmol of fructose within one minute.

The nucleic acid molecules of the invention can be DNA molecules, in particular genomic molecules. Moreover, the nucleic acid molecules of the invention may be RNA molecules. The nucleic acid molecules of the invention can be obtained for instance from natural sources or may be produced synthetically or by recombinant techniques.

The nucleic acid molecules of the invention allow host cells to be prepared which produce recombinant alternansucrase protein of high purity and/or in sufficient quantities, and genetically engineered plants possessing an activity of these enzymes leading to the formation of alternan in planta. Within the framework of the present invention the term "high purity" means that the protein according to the invention displays a degree of purity of at least 80%, preferably of at least 90%, even more preferably of at least 95%. Moreover, means and methods are provided which may be used for preparing alternan using host cells and/or for preparing recombinant alternansucrase protein. Consequently, the provision of the nucleic acid molecules of the invention permits the preparation of alternan of high purity by methods which are relatively inexpensive and consume relatively little time.

In a preferred embodiment, the nucleic molecules of the invention are derived from microorganisms, preferably from bacteria, more preferably from gram-positive bacteria and in particular preferably from bacteria belonging to the genus Leuconostoc. Nucleic acid molecules from bacteria belonging to the species *Leuconostoc mesenteroides* are particularly preferred.

The invention also relates to oligonucleotides specifically hybridizing to a nucleic acid molecule of the invention. Such oligonucleotides have a length of preferably at least 10, in particular at least 15, and particularly preferably of at least 50 nucleotides. They are characterized in that they specifically hybridize to the nucleic acid molecules of the invention, that is to say that they do not or only to a very minor extent hybridize to nucleic acid sequences encoding other proteins, in particular other glucosyltransferases. The oligonucleotides of the invention can be used for instance as primers for amplification techniques such as the PCR reaction or as a hybridization probe to isolate related genes.

Moreover, the invention relates to vectors, in particular plasmids, cosmids, viruses, bacteriophages and other vectors commonly used in gene technology, which contain the above-described nucleic acid molecules of the invention. In a preferred embodiment of the invention, the vectors of the invention lend themselves to the transformation of fungal cells or cells of microorganisms. Preferably, such vectors are suitable to transform plant cells. Particularly preferably, such vectors permit the integration of the nucleic acid molecules of the invention, possibly together with flanking regulatory regions, into the genome of the plant cell. Examples thereof are binary vectors which can be used in the Agrobacteria-mediated gene transfer, and some are already commercially available.

In another preferred embodiment, the nucleic acid molecules contained in the vectors are connected to regulatory elements ensuring the transcription and synthesis of a translatable RNA in prokaryotic or eukaryotic cells.

The expression of the nucleic acid molecules of the invention in prokaryotic or eukaryotic cells, for instance in *Escherichia coli*, is interesting because it permits a more precise characterization of the enzymatic activities of the enzymes encoded by these molecules. Moreover, it is possible to express these enzymes in such prokaryotic or eukaryotic cells which are free from interfering enzymes, such as dextransucrases or other polysaccharide-forming or polysaccharide-degrading enzymes. In addition, it is possible to insert different mutations into the nucleic acid molecules by methods usual in molecular biology (see for instance Sambrook et al., 1989, Molecular Cloning, A Laboratory Manual, $2^{nd}$ edition, Cold Spring Harbor Laboratory Press, Cold Spring Harbor, N.Y.), leading to the synthesis of proteins possibly having modified biological properties. On the one hand it is possible in this connection to produce deletion mutants in which nucleic acid molecules are produced by progressive deletions from the 5' or 3' end of the coding DNA sequence, and said nucleic acid molecules lead to the synthesis of correspondingly shortened proteins. Such deletions at the 5' end of the nucleotide sequence for instance allow amino acid sequences to be identified which are responsible for the secretion of the enzyme in microorganisms (transit peptides). This permits the deliberate preparation of enzymes which are no longer secreted by the removal of the corresponding sequences, but remain within the cell of the corresponding host organism or are localized in other compartments, for instance in the plastids, mitochondria, vacuole, on account of the addition of other signal sequences.

On the other hand, the introduction of point mutations is also conceivable at positions at which a modification of the amino acid sequence for instance influences the enzyme activity or the control of the enzyme. In this manner, it is for instance possible to produce mutants which possess a modified stereo and regio selectivity or a modified Km value or which are no longer subject to the control mechanisms normally existing in the cell and realized via an allosteric control or covalent modification.

Moreover, mutants possessing a modified substrate or product specificity can be prepared. Furthermore, it is possible to prepare mutants having a modified activity-temperature-profile.

Furthermore, in the case of expression in plants, the insertion of mutations into the nucleic acid molecules of the invention allows the gene expression rate and/or the activity of the proteins encoded by the nucleic acid molecules of the invention to be increased.

For genetic engineering in prokaryotic cells, the nucleic acid molecules of the invention or parts of these molecules can be introduced into plasmids which permit mutagenesis or sequence modification by recombination of DNA sequences. Standard methods (see Sambrook et al., 1989, Molecular Cloning: A laboratory manual, $2^{nd}$ edition, Cold Spring Harbor Laboratory Press, NY, USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Moreover, the invention relates to plasmid pAlsu-pSK (see FIG. 2 and Example 2) which was deposited at Deutsche Sammlung fur Mikroorganismen und Zelikulturen (DSMZ), Braunschweig, under the accession No. DSM 12666 on Feb. 4, 1999, and to the nucleic acid molecules contained in the insert of plasmid DSM 12666 and encoding a protein possessing the enzymatic activity of an alternansucrase. Moreover, the present invention also relates to nucleic acid molecules which hybridize to the insertion of plasmid DSM 12666. Also, the present invention relates to nucleic acid molecules the nucleotide sequence of which deviates from that of the nucleic acid molecules of the plasmid DSM 12666 insert, because of the degeneration of the genetic code. Furthermore, the present invention relates to nucleic acid molecules which have a homology, that is to say a sequence identity of at least 40%, preferably of at least 60%, more preferably of at least 80%, even more preferably of at least 90%, and most preferably of at least 95% to the sequence of the insertion of plasmid DSM 12666.

Another embodiment of the invention relates to host cells, in particular prokaryotic or eukaryotic cells transformed with an above-described nucleic acid molecule of the invention or with a vector of the invention, and to cells descended from such transformed cells and containing a nucleic acid molecule or vector of the invention.

According to another preferred embodiment, the host cells are cells of microorganisms. In the context of the present invention, the term "microorganism" comprises bacteria and all protists (e.g. fungi, in particular yeasts, algae) as defined Schlegel's "Aligemeine Mikrobiologie" (Georg Thieme Verlag, 1985, 1–2). A preferred embodiment of the invention relates to cells of algae and host cells belonging to the genera Aspergillus, Bacillus, Saccharomyces or Pichia (Rodriguez, Journal of Biotechnology 33 (1994), 135–146, Romanos, Vaccine, Vol. 9 (1991), 901 et seq.). A particularly preferred embodiment of the invention relates to *E. coli* cells. Alternansucrase is especially preferably secreted by the host cell. The preparation of such host cells for the production of recombinant alternansucrase can be carried out by methods known to a man skilled in the art. In a preferred embodiment of the invention, the host cells of the invention show no interfering enzymatic activities, such as those of polysaccharide-forming and/or polysaccharide-degrading enzymes.

An overview of different expression systems is for instance contained in Methods in Enzymology 153 (1987), 385–516, in Bitter et al. (Methods in Enzymology 153 (1987), 516–544) and in Sawers et al. (Applied Microbiology and Biotechnology 46 (1996), 1–9), Billman-Jacobe (Current Opinion in Biotechnology 7 (1996), 500–4), Hockney (Trends in Biotechnology 12 (1994), 456–463), Griffiths et al, Methods in Molecular Biology 75 (1997), 427–440). An overview of yeast expression systems is for instance given by Hensing et al. (Antonie van Leuwenhoek 67 (1995), 261–279), Bussineau et al. (Developments in Biological Standardization 83 (1994), 13–19), Gellissen et al. (Antonie van Leuwenhoek 62 (1992), 79–93, Fleer (Current Opinion in Biotechnology 3 (1992), 486–496), Vedvick (Current Opinion in Biotechnology 2 (1991), 742–745) and Buckholz (Bio/Technology 9 (1991), 1067–1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters producing a constitutive expression of the gene and inducible promoters which permit a deliberate control of the expression of the postconnected gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of the postconnected gene are for instance the T7 promoter (Studier et al., Methods in Enzymology 185 (1990), 60–89), lacUV5, trp, trp-lacUV5 (DeBoer et al., in Rodriguez and Chamberlin (Eds), Promoters, Structure and Function; Praeger, N.Y., (1982), 462–481; DeBoer et al., Proc. Natl. Acad. Sci. USA (1983), 21–25), Ip1, rac (Boros et al., Gene 42 (1986), 97–100). As a rule, the protein amounts are highest from the middle up to about the end of the logarithmic phase of the growth cycle of the microorganisms. Therefore, inducible promoters are preferably used for the synthesis of proteins. These promoters often lead to higher protein yields than do constitutive promoters. The use of highly constitutive promoters leads to the continuous transcription and translation of a cloned gene and thus often has the result that energy is lost for other essential cells functions with the effect that cell growth is slowed down (Bernard R. Glick/Jack J. Pasternak, Molekulare Biotechnologie (1995). Spektrum Akademischer Verlag GmbH, Heidelberg, Berlin, Oxford, p. 342). Therefore, in order to obtain an optimum amount of protein, a two-stage process is often used. First, the host cells are cultured under optimum conditions up to a relatively high cell density. In the second step, transcription is then induced depending on the type of promoter used. In this connection, a tac promoter is particularly suitable which can be induced by lactose or IPTG (=isopropyl-β-D-thiogalactopyranoside) (deBoer et al., Proc. Natl. Acad. Sci. USA 80 (1983), 21–25). Termination signals for transcription are also described in the literature.

The transformation of the host cell with DNA encoding an alternansucrase can, as a rule, be carried out by standard methods, as for instance described in Sambrook et al., (Molecular Cloning: A Laboratory Course Manual, $2^{nd}$ edition (1989) Cold Spring Harbor Press, New York; Methods in Yeast Genetics, A Laboratory Course Manual, Cold Spring Harbor Laboratory Press, 1990). The host cell is cultured in nutrient media meeting the requirements of the particular host cell used, in particular in respect of the pH value, temperature, salt concentration, aeration, antibiotics, vitamins, trace elements etc.

Moreover, the invention relates to proteins and biologically active fragments thereof, which are encoded by the nucleic acid molecules of the invention and to methods for their preparation, wherein a host cell according to the invention is cultured under conditions permitting the synthesis of the protein, and the protein is subsequently isolated from the cultured cells and/or the culture medium.

According to a preferred embodiment of the invention, the alternansucrase is a recombinantly produced protein. In the context of the present invention, this is a protein prepared by inserting a DNA sequence encoding the protein into a host cell and expressing it therein. The protein can then be isolated from the host cell and/or the culture medium.

The nucleic acid molecules of the invention now allow host cells to be prepared which produce recombinant alternansucrase protein of high purity and/or in sufficient amounts. Within the framework of the present invention the term "high purity" means that the protein according to the invention displays a degree of purity of at least 80%, preferably of at least 90%, even more preferably of at least 95%. The time-consuming and costly methods already mentioned above, whereby alternansucrase protein which to date can only be obtained from particular Leuconostoc strains can be purified from other components such as for instance dextransucrases, polysaccharides, are dispensed with, because alternansucrase can be produced in host cells not possessing any adverse polysaccharide-synthesizing activities. Moreover, host cells and vectors can also be used, which allow the alternansucrase protein to be produced in the absence of saccharose, with the result that an additional separation of the alternansucrase protein from polysaccharides is no longer necessary. Moreover, the selection of suitable host cells and vectors allows alternansucrase protein to be provided in sufficient amounts, which has not been possible with the systems so far described.

Alternansucrase produced by the host cells can be purified by conventional purification methods, such as precipitation, ion exchange chromatography, affinity-chromatography, gel filtration, HPLC Reverse Phase Chromatography etc. The modification of the nucleic acid molecules of the invention encoding an alternansucrase and expressed in the host cells, allows to produce a polypeptide in the host cell which is easier to isolate from the culture medium because of particular properties. Thus, the protein to be expressed can be expressed as a fusion protein with an additional polypeptide sequence, the specific binding properties of which permit the isolation of the fusion protein by affinity chromatography (e.g. Hopp et al., Bio/Technology 6 (1988), 1204–1210; Sassenfeld, Trends Biotechnol. 8 (1990), 88–93).

Another embodiment of the invention relates to proteins possessing the enzymatic activity of an alternansucrase, in particular that from microorganisms, preferably Gram-positive microorganisms, particularly microorganisms of the genus Leuconostoc, and particularly preferably that from *Leuconostoc mesenteroides*. The molecular weight of the protein indicated in Seq. ID No. 2, as determined by calculation, is 228.96 kDa. The invention also relates to alternansucrases which possess a molecular weight of 229 kDa±120 kDa, preferably 229 kDa±50 kDa, and particularly preferably 230 kDa±25 kDa. The molecular weight of the mature protein, as determined by calculation, is 224.77 kDa.

The provision of the nucleic acid molecules of the invention, for the first time, makes it possible to prepare alternansucrase-expressing plant cells by means of genetic engineering, which was not possible so far, because classical culturing methods do not allow bacterial and fungal genes to be expressed in plants.

The invention, therefore, also relates to transgenic plant cells transformed by a nucleic acid molecule of the invention or a vector of the invention or descended from such cells, the nucleic acid molecule which encodes the protein that has the biological activity of an alternansucrase being under the control of regulatory elements permitting the transcription of a translatable mRNA in plant cells.

The introduction of the activity of the proteins of the invention, for instance by expression of corresponding nucleic acid molecules, opens the possibility of producing alternan in plant cells correspondingly modified by genetic engineering. Hence, the expression of the nucleic acid molecules of the invention in plant cells is possible, allowing an additional, corresponding alternansucrase activity not present in the wild type to be introduced. Moreover, it is possible to modify the nucleic acid molecules of the invention according to methods known to a skilled person, in order to obtain alternansucrases of the invention which for instance possess modified temperature dependencies or substrate or product specificities. Such methods have already been described in more detail in a different context above.

A plurality of techniques is available by which DNA can be inserted into a plant host cell. These techniques include the transformation of plant cells by T-DNA using *Agrobacterium tumefaciens* or *Agrobacterium rhizogenes* as a transforming agent, the fusion of protoplasts, injection, electroporation of DNA, insertion of DNA by the biolistic approach and other possibilities.

The use of the Agrobacteria-mediated transformation of plant cells has been extensively investigated and sufficiently described in EP 120 516; Hoekema, In: The Binary Plant Vector System, Offsetdrukkerij Kanters B. V., Alblasserdam (1985), Chapter V; Fraley et al, Crit. Rev. Plant Sci. 4 (1993), 1–46 and An et al., EMBO J. 4 (1985), 277–287. Regarding the transformation of potatoes see for instance Rocha-Sosa et al. (EMBO J. 8 (1989), 29–33).

The transformation of monocotyledonous plants by means of Agrobacterium-based vectors has also been described (Chan et al., Plant Mol. Biol. 22 (1993), 491–506; Hiei et al., Plant J. 6 (1994) 271–282; Deng et al, Science in China 33 (1990), 28–34; Wilmink et al, Plant Cell Reports 11 (1992), 76–80; May et al., Bio/Technology 13 (1995), 486–492; Conner and Dormisse, Int. J. Plant Sci. 153 (1992), 550–555; Ritchie et al. Transgenic Res. 2 (1993), 252–265). An alternative system for transforming monocotyledonous plants is the transformation by the biolistic approach (Wan and Lemaux, Plant Physiol. 104 (1994), 37–48; Vasil et al., Bio/Technology 11 (1993), 1553–1558; Ritala et al., Plant Mol. Biol. 24 (1994) 317–325; Spencer et al., Theor. Appl. Genet. 79 (1990), 625–631), protoplast transformation, electroporation of partially permeabilized cells, insertion of DNA via glass fibers. The transformation of maize in particular has been repeatedly described in the literature (see for instance WO 95/06128, EP 0 513 849, EP 0 465 875, EP 29 24 35; Fromm et al, Biotechnology 8, (1990), 833–844; Gordon-Kamm et al., Plant Cell 2, (1990), 603–618; Koziel et al., Biotechnology 11 (1993), 194–200; Moroc et al., Theor. Appl. Genet. 80, (1990), 721–726).

The successful transformation of other types of cereals has also been described for instance of barley (Wan and Lemaux, supra; Ritala et al., supra, Krens et al., Nature 296 (1982), 72–74) and wheat (Nehra et al., Plant J. 5 (1994), 285–297). Generally, any promoter active in plant cells is suitable to express the nucleic acid molecules in plant cells. The promoter can be so chosen that the expression in the plants of the invention occurs constitutively or only in a particular tissue, at a particular time of plant development or at a time determined by external influences. The promoter may be homologous or heterologous to the plant.

Suitable promoters are for instance the promoter of 35S RNA of the Cauliflower Mosaic Virus (see for instance U.S. Pat. No. 5,352,605) and the ubiquitin-promoter (see for instance U.S. Pat. No. 5,614,399) which lend themselves to constitutive expression, the patatin gene promoter B33 (Rocha-Sosa et al., EMBO J. 8 (1989), 23–29) which lends itself to a tuber-specific expression in potatoes or a promoter ensuring expression in photosynthetically active tissues only, for instance the ST-LS1 promoter (Stockhaus et al., Proc. Natl. Acad. Sci. USA 84 (1987), 7943–7947; Stockhaus et al., EMBO, J. 8 (1989) 2445–2451), the Ca/b-promoter (see for instance U.S. Pat. No. 5,656,496, U.S. Pat. No. 5,639,952, Bansal et al., Proc. Natl. Acad. Sci. USA 89 (1992), 3654–3658) and the Rubisco SSU promoter (see for instance U.S. Pat. No. 5,034,322; U.S. Pat. No. 4,962,028) or the glutelin promoter from wheat which lends itself to endosperm-specific expression (HMW promoter) (Anderson, Theoretical and Applied Genetics 96, (1998), 568–576, Thomas, Plant Cell 2 (12), (1990), 1171–1180), the glutelin promoter from rice (Takaiwa, Plant Mol. Biol. 30(6) (1996), 1207–1221, Yoshihara, FEBS Lett. 383 (1996), 213–218, Yoshihara, Plant and Cell Physiology 37 (1996), 107–111), the shrunken promoter from maize (Maas, EMBO J. 8 (11) (1990), 3447–3452, Werr, Mol. Gen. Genet. 202(3) (1986), 471–475, Werr, Mol. Gen. Genet. 212(2), (1988), 342–350), the USP promoter, the phaseolin promoter (Sengupta-Gopalan, Proc. Natl. Acad. Sci. USA 82 (1985), 3320–3324, Bustos, Plant Cell 1 (9) (1989), 839–853) or promoters of zein genes from maize (Pedersen et al., Cell 29 (1982), 1015–1026; Quatroccio et al., Plant Mol. Biol. 15 (1990), 81–93). However, promoters which are only activated at a point in time determined by external influences can also be used (see for instance WO 93/07279). In this connection, promoters of heat shock proteins which permit simple induction may be of particular interest. Moreover, seed-specific promoters such as the USP promoter from Vicia faba which ensures a seed-specific expression in Vicia faba and other plants may be used (Fiedler et al., Plant Mol. Biol. 22 (1993), 669–679; Bäumlein et al., Mol. Gen. Genet. 225 (1991), 459–467). Moreover, fruit-specific promoters, such as described in WO 91/01373 may be used too.

Moreover, a termination sequence may be present, which serves to terminate transcription correctly and to add a poly-A-tail to the transcript, which is believed to have a function in the stabilization of the transcripts. Such elements are described in the literature (see for instance Gielen et al., EMBO J. 8 (1989), 23–29) and can be replaced at will.

Such cells can be distinguished from naturally occurring plant cells inter alia by the fact that they contain a nucleic acid molecule of the invention which does not naturally occur in these cells. Moreover, such transgenic plant cells of the invention can be distinguished from naturally occurring plant cells in that they contain at least one copy of the nucleic acid molecule of the invention stably integrated in their genome.

Moreover, the plant cells of the invention can preferably be distinguished from naturally occurring plant cells by at least one of the following features: If the inserted nucleic acid molecule of the invention is heterologous to the plant cell, then the transgenic plant cells are found to have transcripts of the inserted nucleic acid molecules of the invention. The latter can be detected for instance by Northern blot analysis. The plants cells of the invention preferably contain a protein encoded by an inserted nucleic acid molecule of the invention. This can be shown for instance by immunological methods, in particular by Western blot analysis.

Transgenic plant cells can be regenerated to whole plants according to methods known to a person skilled in the art.

The present invention also relates to the plants obtainable by regeneration of the transgenic plant cells of the invention. Furthermore, it relates to plants containing the above-described transgenic plant cells.

In most plants, the photoassimilates in the form of sugars formed during photosynthesis within a plant, i.e. mainly in the form of saccharose, are transported to the corresponding target organs. As saccharose is the substrate of the polymerization reaction of alternansucrase, all plants, both monocotyledonous and dicotyledonous can, in principle, be modified by the nucleic acid molecule of the invention in respect of alternansucrase expression.

The expression in plants of the nucleic acid molecules of the invention encoding a protein having the enzymatic activity of an alternansucrase can, for instance, be used to achieve a modification of the viscosity of the extracts possibly obtained from the plants, said modification being achieved by the synthesis of alternan. In this connection, for instance tomatoes are of interest. The expression of an alternansucrase in a tomato fruit leads to the synthesis of alternan and results in a modification of the viscosity of extracts obtained from these fruits for instance for the production of tomato puree or tomato ketchup.

The expression of the nucleic acid molecules of the invention is in particular advantageous in those organs of the plant which show a higher saccharose content or store saccharose. Such organs are for instance the beet of sugar beet or the cane of sugar cane. As these plants normally do not store any appreciable amounts of starch, the alternans synthesized by the alternansucrase from these plants could be isolated in the pure form.

The site where the biosynthesis of the saccharose in the plant cell occurs is the cytosol. The storage site, however, is the vacuole. During its transport into the storage tissue of the sugar beet or the potato or during its transport into the endosperm of seeds, the saccharose must pass the apoplast. Hence, all three compartments, i.e. the cytosol, the vacuole, the apoplast, lend themselves to the expression of the nucleic acid molecules for the synthesis of alternan. In addition, the plastids also lend themselves thereto, as could for instance be shown by the expression of bacterial fructosyl transferases in amyloplasts. Said fructosyl transferases which likewise require saccharose as a substrate, were able to mediate the formation of "amylofructan" in amyloplasts (Smeekens, Trends in Plant Science, Vol. 2, No. 8 (1997), 286–288).

In the case of starch-producing plants, such as potatoes and maize, where the starch biosynthesis and starch storage normally take place in the amyloplasts, an expression of the alternansucrase in apoplasts, in the cytosol or in the vacuole would lead to an additional synthesis of oligosaccharides and/or polysaccharides in these compartments, which can mean an overall increase in the yield.

As in the case of potatoes the starch synthesized in the amyloplasts can be separated from the alternan synthesized in the apoplast, in the cytosol or in the vacuole, the very same plant can be used to recover starch and alternan.

Moreover, transgenic potato and maize plants are known, the starch synthesis of which in the tubers and grains, respectively, is completely inhibited due to the inhibition of ADP-glucose-pyrophosphorylase by an antisense construct. In the case of potatoes, soluble sugars, in particular saccharose and glucose, accumulate instead, for instance in the tubers (Müller-Röber et al., EMBO J. 11 (1992), 1229–1238). Alternan can be prepared in the cytosol, the vacuole or apoplast of these plants by the expression of an alternansucrase which uses saccharose as a substrate.

Therefore in another embodiment of the invention the plant cells of the invention are further characterized by a reduced ADP glucose pyrophosphorylase (AGPase) activity compared to corresponding cells from wild-type plants.

DNA molecules encoding AGPase are well known to the person skilled in the art and described for example in Müller-Röber et al. (Mol. Gen. Genet. 224 (1) (1990), 136–146). By using DNA molecules encoding an AGPase it is possible to produce plants by means of recombinant DNA techniques (for example by an antisense, a ribozyme or a cosuppression approach) showing a reduced AGPase activity. Furthermore AGPase mutants, for example from maize (brittle-2 and shrunken-2), with reduced AGPase activity are known to the person skilled in the art.

The term "reduced" means preferably a reduction of AGPase activity of at least 10%, more preferably of at least 50% and even more preferably of at least 80% in comparison to corresponding wild-type cells.

The activity of an AGPase can be determined according to Müller-Röber et al. (Mol. Gen. Genet. 224 (1) (1990), 136–146) or to methods known to a person skilled in the art.

The reaction which is catalyzed by alternansucrase is distinguished by the fact that a glucose moiety is transferred directly from saccharose to an existing carbohydrate acceptor. By contrast, in the case of plants, the biosynthesis of linear glucans from saccharose, proceeds in such a way that the saccharose is first separated into glucose and fructose, which are then each converted into activated intermediate ADP-glucose. The glucose moiety is transferred by the enzyme starch-synthase from the ADP glucose to an already existing glucan, whereby ADP is released. The conversion of saccharose into two ADP glucose molecules requires several energy consuming reactions. Therefore, the energy consumption of the reaction catalyzed by alternansucrase is substantially lower than the energy consumption in the synthesis of polysaccharides from saccharose in plant cells, which can lead to an increased yield of synthesized oligo and/or polysaccharides in plants containing the nucleic acid molecules of the invention.

In the expression of the nucleic acid molecules in plants there exists in principle the possibility that the synthesized protein can be localized in any compartment of the plant cell (e.g. in the cytosol, plastids, vacuole, mitochondria) or the plant (e.g. in the apoplast). In order to achieve the localization in a particular compartment, the coding region must, where necessary, be linked to DNA sequences ensuring localization in the corresponding compartment. The signal sequences used must each be arranged in the same reading frame as the DNA sequence encoding the enzyme.

In order to ensure the location in the plastids it is conceivable to use one of the following transit peptides: of the plastidic Ferredoxin: NADP+ oxidoreductase (FNR) of spinach which is enclosed in Jansen et al. (Current Genetics 13 (1988), 517–522). In particular, the sequence ranging from the nucleotides −171 to 165 of the cDNA Sequence disclosed therein can be used, which comprises the 5'nontranslated region as well as the sequence encoding the transit peptide. Another example is the transit peptide of the waxy protein of maize including the first 34 amino acid residues of the mature waxy protein (Klösgen et al., Mol. Gen. Genet. 217 (1989), 155–161). It is also possible to use this transit peptide without the first 34 amino acids of the mature protein. Furthermore, the signal peptides of the ribulose bisphosphate carboxylase small subunit (Wolter et al., Proc. Natl. Acad. Sci. USA 85 (1988), 846–850; Nawrath et al., Proc. Natl. Acad. Sci. USA 91 (1994), 12760–12764), of the NADP malate dehydrogenase (Gallardo et al., Planta 197 (1995), 324–332), of the glutathione reductase (Creissen et al., Plant J. 8 (1995), 167–175) or of the R1 protein Lorberth et al. (Nature Biotechnology 16, (1998), 473–477) can be used.

In order to ensure the location in the vacuole it is conceivable to use one of the following transit peptides: the N-terminal sequence (146 amino acids) of the patatin protein (Sonnewald et al., Plant J. 1 (1991), 95–106) or the signal sequences described by Matsuoka und Neuhaus, Journal of Experimental Botany 50 (1999), 165–174; Chrispeels und Raikhel, Cell 68 (1992), 613–616; Matsuoka und Nakamura, Proc. Natl. Acad. Sci. USA 88 (1991), 834–838; Bednarek und Raikhel, Plant Cell 3 (1991), 1195–1206; Nakamura und Matsuoka, Plant Phys. 101 (1993), 1–5.

In order to ensure the location in the mitochondria it is for example conceivable to use the transit peptide described by Braun et al.(EMBO J. 11, (1992), 3219–3227). In order to ensure the location in the apoplast it is conceivable to use one of the following transit peptides: signal sequence of the proteinase inhibitor 11-gene (Keil et al., Nucleic Acid Res. 14 (1986), 5641–5650; von Schaewen et al., EMBO J. 9 (1990), 30–33), of the levansucrase gene from *Erwinia amylovora* (Geier and Geider, Phys. Mol. Plant Pathol. 42 (1993), 387–404), of a fragment of the patatin gene B33 from *Solanum tuberosum*, which encodes the first 33 amino acids (Rosahl et al., Mol Gen. Genet. 203 (1986), 214–220) or of the one described by Oshima et al. (Nucleic Acid Res. 18 (1990), 181).

The nucleic acid sequence indicated in Seq. ID No. 1 encodes an extracellular alternansucrase. Secretion is ensured by a signal sequence comprising the first approximately 39 N-terminal amino acid residues of the Seq. ID No. 2.

The transgenic plants may, in principle, be plants of any plant species, that is to say they may be monocotyledonous and dicotyledonous plants. Preferably, the plants are useful plants cultivated by man for nutrition or for technical, in particular industrial, purposes. They are preferably starch-storing plants, for instance cereal species (rye, barley, oat, wheat, millet, sago etc.), rice, pea, marrow pea, cassava and potato; tomato, rape, soybean, hemp, flax, sunflower, cow pea or arrowroot, fiber-forming plants (e.g. flax, hemp, cotton), oil-storing plants (e.g. rape, sunflower, soybean) and protein-storing plants (e.g. legumes, cereals, soybeans). The invention also relates to fruit trees and palms. Moreover, the invention relates to forage plants (e.g. forage and pasture grasses, such as alfalfa, clover, ryegrass) and vegetable plants (e.g. tomato, lettuce, chicory) and ornamental plants (e.g. tulips, hyacinths). Sugar-storing and/or starch-storing plants are preferred. Sugar cane and sugar beet,. and potato plants, maize, rice, wheat and tomato plants are particularly preferred.

A further subject of the invention is a method for the production of transgenic plant cells and transgenic plants which in comparison to non-transformed wildtype cells/non-transformed wildtype plants synthesize alternan. In this method the expression and/or the activity of proteins encoded by the nucleic acid molecules of the invention is increased in comparison to corresponding wild-type cells/wildtype plants which do not show any alternansucrase expression and/or activity. In particular, such a method comprises the expression of a nucleic acid molecule according to the invention in plant cells. The nucleic acid molecule according to the invention is preferably linked to a promoter ensuring expression in plant cells. In a particularly preferred embodiment the method comprises the introduction of a nucleic acid molecule according to the invention into a plant cell and regeneration of a plant from this cell.

Such an increase in expression may, e.g., be detected by Northern blot analysis. The increase in activity may be detected by testing protein extracts for their alternansucrase activity derived from plant cells. The enzymatic activity of an alternansucrase can be measured, for instance, as described in Lopez-Munguia et al. (Annals New York Academy of Sciences 613, (1990), 717–722) or as described in the examples of the present application.

The invention also relates to propagation material of the plants of the invention. The term "propagation material" comprises those components of the plant which are suitable to produce offspring vegetatively or generatively. Suitable means for vegetative propagation are for instance cuttings, callus cultures, rhizomes or tubers. Other propagation material includes for instance fruits, seeds, seedlings, protoplasts, cell cultures etc. The preferred propagation materials are tubers and seeds. The invention also relates to harvestable parts of the plants of the invention such as, for instance, fruits, seeds, tubers or rootstocks.

Another embodiment of the invention relates to methods for preparing alternan which comprise the step of extracting and isolating alternan from a plant of the invention.

The extraction and isolation of alternan from a plant of the invention may be carried out by standard methods, such as precipitation, extraction and chromatographic methods.

Moreover, the present invention relates to alternan obtainable from a plant of the invention or from propagation material of the invention.

Moreover, the present invention relates to a method for preparing alternan and/or fructose, wherein a host cell of the invention secretes an alternansucrase into a saccharose-containing culture medium and alternan and/or fructose is/are isolated from the culture medium.

A preferred embodiment of the method of the invention uses an alternansucrase recombinantly produced and secreted by the host cell into the culture medium, thus avoiding the necessity of breaking up the cells and purifying the protein further, because the secreted protein can be obtained from the supernatant. The residual components of the culture medium can be removed by methods usual in processing technology, such as dialysis, reverse osmosis, chromatographic methods, etc. The same applies to the concentration of the protein secreted into the culture medium. The secretion of proteins by microorganisms is normally mediated by N-terminal signal peptides (signal sequence, leader-peptide, transit peptide). Proteins possessing this signal sequence are able to penetrate the cell membrane of the microorganism. A secretion of proteins can be achieved by adding the DNA sequence encoding this signal peptide to the corresponding region encoding the alternansucrase.

The natural signal peptide of the expressed alternansucrase is preferred, that of the alternansucrase from *Leuconostoc mesenteroides* NRRL B 1355 (see the first approximately 25 to 45 N-terminal amino acid residues of Seq. ID No. 2) is particularly preferred.

The signal peptide of α-CGTase from *Klebsiella oxytoca* M5A1 (Fiedler et al., J. Mol. Biol. 256 (1996), 279–291) or a signal peptide as encoded by the nucleotides 11529–11618 of the sequence available under the GenBank accession number X86014 is most preferred.

The preparation of alternan and/or fructose requires neither activated glucose derivatives nor co-factors, as are necessary in most synthesis reactions for polysaccharides occurring within the cells. Hence, alternansucrase-secreting microorganisms can be cultured in saccharose-containing medium, the secreted alternansucrase leading to a synthesis of alternan and fructose in the culture medium.

Contrary to host cells from *Leuconostoc mesenteroides*, which secrete alternansucrase by nature, the host cells used according to the invention have the advantage that they do not secrete proteins possessing adverse polysaccharide-synthesizing side reactions, such as dextransucrase, with the result that outside the host cell, apart from alternan, no other polysaccharides can be formed which, as a rule, can be separated from alternan only by costly and time-consuming procedures. Moreover, the host cells according to a preferred embodiment of the invention do not have any adverse polysaccharide-degrading side activities, which would otherwise lead to losses in the yield of the alternan produced.

The method of the invention yields fructose apart from alternan. Fructose can be used for the inexpensive isolation of so-called "high-fructose-containing syrups" (HFCS). Conventional methods for preparing fructose on the one hand provide for the enzymatic break down of saccharose by means of an invertase or for the break down of starch into glucose units, mostly brought about by acid hydrolysis, and for subsequent enzymatic conversion of the glucose into fructose by glucose isomerases. However, both methods lead to mixtures of glucose and fructose. The two components must subsequently be separated from each other by chromatographic methods.

The separation of the two reaction products of the method of the invention, or the separation of the reaction products from the substrate saccharose can be achieved for example with the use of membranes permitting the penetration of fructose, but not the penetration of saccharose and/or alternans. If continuous removal of fructose via such a membrane is provided for, a more or less complete conversion of saccharose occurs.

The isolation of alternan and fructose can be carried out by standard methods or can be carried out as for instance described in the working examples.

According to one embodiment of the method, the host cells originate from microorganisms, preferably from *Escherichia coli*.

In another embodiment, the method of the invention works with fungal host cells, in particular cells of yeasts, such as *Saccharomyces cerevisiae*. Yeast cells producing alternan in saccharose-containing medium because of the enzymatic activity of an alternansucrase, cannot be readily used, as yeasts secrete an invertase which breaks down the extracellular saccharose. The yeasts take up the resulting hexoses via a hexose transporter. However, one yeast strain has been described (Riesmeier et al. EMBO J. 11 (1992), 4705–4713) which carries a defective suc2 gene, and therefore cannot secrete invertase. Moreover, these yeast cells do not contain a transportation system able to import saccharose into the cells. If such a strain is so modified by means of the nucleic acid molecules of the invention that it secretes an alternansucrase into the culture medium, then fructose and alternan will be synthesized in saccharose-containing medium. The resulting fructose can subsequently be taken up by the yeast cells.

In another preferred embodiment of this method the host cell of the invention is present in an immobilized form.

As a rule, host cells are immobilized by inclusion of the cells in a suitable material, such as alginate, polyacrylamide, gelatin, cellulose or chitosan. However, adsorption or covalent binding of the cells to a carrier material is also possible (Brodelius and Mosbach, Methods in Enzymology Vol. 135 (1987), 222–230) An advantage of the immobilization of cells is that it allows substantially higher cell densities to be achieved than does culturing in liquid culture. This results in a higher productivity. Moreover, the costs for agitation and aeration of the culture decrease as do the costs for measures to maintain sterility. Another important aspect is the possibility of a continuous alternan production with the result that unproductive phases regularly occurring in fermentation processes can be avoided or at least greatly reduced.

Another embodiment of the invention relates to a method for preparing alternan and/or fructose, wherein
a) a saccharose-containing solution is contacted with a protein of the invention under conditions permitting the conversion of saccharose into alternan and/or fructose; and
b) alternan and/or fructose is/are isolated from the solution.

In this embodiment, the invention thus relates to a method for preparing alternan and/or fructose in vitro by means of a cell-free enzyme preparation. In this case, microorganisms which for instance secrete alternansucrase are cultured up to the stationary phase in a saccharose-free medium permitting the formation of alternansucrase protein. After removing the cells from the culture medium by centrifugation, the secreted enzyme can be recovered from the supernatant. The enzyme can subsequently be added to saccharose-containing solutions in order to synthesize alternan and/or fructose. Compared to the above-described synthesis of alternan in a system not freed from cells, this method offers the advantage that the reaction conditions can be controlled better and the reaction products are substantially purer and easier to purify. The purification of the protein can be carried out as already described above.

A preferred embodiment of the method of the invention uses a purified alternansucrase. Purified alternansucrase is understood to mean an enzyme which is largely free from cell components of the cells in which the protein is synthesized and shows no contamination with proteins possessing polysaccharide-synthesizing activities (e.g. dextransucrases) or degrading activities, and/or no contamination with (polysaccharide) acceptors. The term "purified alternansucrase" preferably means an alternansucrase possessing a degree of purity of at least 70%, preferably at least 85%, and particularly preferably at least 95%.

The use of a purified protein for preparing alternan and/or fructose offers various advantages. Compared to methods working with partially purified protein extracts, the reaction medium of the method of the invention does not contain any residues of the production strain (microorganism) which is used for the purification of the protein or for its preparation by genetic engineering.

Moreover, the use of the purified protein is advantageous for food and pharmaceutical industry applications. Thanks to the fact that the reaction medium is defined in its composition and freed from all unnecessary components, the product is likewise more precisely defined in respect of its components. In consequence of this, the procedure for obtaining food and pharmaceutical industry approval of these products produced by genetic engineering requires substantially less documentation, especially since these products should not show any traces of a transgenic microorganism.

Moreover, contrary to the so far described in vitro methods in cell free systems using partially purified alternansucrase preparations, the method of the invention using a purified alternansucrase has the advantage that it allows highly pure alternan to be prepared without the occurrence of dextransucrase and dextran contaminations, because of the high purity of the protein of the invention. Moreover, the method of the invention permits the production of alternan in high yields, without losses caused for instance by adverse side reactions of a dextransucrase, which would convert part of the substrate saccharose into undesired dextran, the separation of which from alternan would only be possible using time-consuming and expensive methods.

The method of the invention produces fructose in addition to alternan. The fructose can be used for the inexpensive recovery of so-called "high-fructose-containing syrups" (HFCS). The method of the invention yields products of high purity, because of the use of a purified alternansucrase. Hence, compared to conventional methods for preparing HFCS from maize starch, which comprise costly process steps for removing the buffer salts by ion exchange, (Crabb and Mitchinson, TIBTECH 15 (1997), 349–352) the method of the invention does not require an expensive purification of the fructose.

Another preferred embodiment of the method of the invention uses a recombinantly prepared alternansucrase.

According to another preferred embodiment, the enzyme possessing the enzymatic activity of an alternansucrase is immobilized on a carrier material. Immobilization of the alternansucrase offers the advantage that the enzyme being the catalyst of the synthesis reaction can be easily recovered from the reaction mixture and reused several times. As the purification of enzymes is normally costly and time consuming, immobilization and reutilization of the enzymes allow for a substantial cost saving. Another advantage is the degree of purity of the reaction products not containing any residual protein.

There are many carrier materials available for the immobilization of proteins, and coupling to the carrier material can be made via covalent or non-covalent bonds (for an overview see: Methods in Enzymology 135, 136, 137). Widely used carrier materials include for instance agarose, alginate, cellulose, polyacrylamide, silica or nylon.

According to another embodiment of the invention, the alternansucrase (immobilized on a carrier material) is present between two membranes, one of which allows fructose, but not saccharose and alternan to penetrate, the other one of which allows saccharose, but not alternan to penetrate. The supply with substrate occurs through the membrane which allows saccharose to penetrate it. The synthesized alternan remains in the space between the two membranes and the released fructose can be continuously removed from the reaction equilibrium via the membrane which only allows fructose to penetrate it. Such an arrangement permits an efficient separation of the reaction products, and thus the production of pure fructose.

Moreover, the separation of fructose by ion exchange chromatography has been described ("Starch Hydrolysis Products, Worldwide Technology, Production, and Application", Edited by F. W. Schenck, R. E. Hebeda, (1992), VCH Publishers, Inc., New York).

Thus, the use of alternansucrases for preparing pure fructose on the one hand involves the advantage that the relatively inexpensive substrate saccharose can be used as the starting material, and on the other hand the fructose can be isolated easily from the reaction mixture without additional enzymatic conversions or chromatographic methods.

Moreover, the invention relates to methods for preparing alternan and/or fructose, wherein
- a) a saccharose-containing solution is contacted with a protein of the invention and acceptor molecules under conditions permitting the conversion of saccharose to alternan and/or fructose; and
- b) alternan and/or fructose is/are isolated from the solution.

Within the framework of the present invention an acceptor molecule is understood to mean a molecule at which an alternansucrase is able to catalyze a chain-extending reaction. The acceptor which can be added to the reaction mixture at the beginning of the reaction is preferably a carbohydrate or a carbohydrate derivative. The use of external acceptors leads to the production of low molecular products which are to be designated alternan in the context of the present invention. The carbohydrate acceptor is preferably an oligo or polysaccharide, in particular a branched polysaccharide, such as dextrin, glycogen or amylopectin, preferably a linear polysaccharide, and particularly preferably a saccharide selected from the group consisting of maltose, isomaltose, isomaltotriose and methyl-α-D-glucan. If an extension of the alternan chain at these acceptors occurs, then products are formed which have a higher molecular weight than the educt. Where maltose, isomaltose, isomaltotriose and methyl-α-D-glucan are used, one obtains products which have a lower molecular weight than the alternan that can be prepared in the absence of external carbohydrate acceptors.

The size of the molecular weight of the oligoalternans prepared depends on the saccharose/acceptor ratio used. For instance the degree of polymerization of the products increases as the saccharose/isomaltose ratio increases.

Moreover, the saccharose/acceptor ratio has an influence on the oligoalternan yield. For instance, the oligoalternan yield increases as the saccharose/isomaltose ratio decreases.

The hitherto described methods for producing oligoalternan with the use of alternansucrases which the authors claim have been purified (Pelenc et al., Sciences Des Aliments 11 (1991), 465–476) only yielded product mixtures of oligoalternan and oligodextran, in the presence of the carbohydrate acceptor maltose. In this case, the synthesis of oligodextran is presumably attributable to dextransucrase-contaminations of the alternansucrase preparation. Compared to this method, the method of the invention offers the advantage that the use of recombinantly produced alternansucrase protein not containing any dextransucrase contaminants permits the preparation of oligoalternan without the simultaneous formation of oligodextran. Thus, the method of the invention makes it possible to provide oligoalternan, without requiring additional costly purification steps for separating oligodextran.

According to another preferred embodiment, the enzyme possessing the enzymatic activity of an alternansucrase is immobilized on a carrier material.

According to another preferred embodiment of the method of the invention, a recombinantly produced alternansucrase is used.

Moreover, the present invention relates to end products containing alternan. In this context, end products are understood to mean cosmetic products, preferably food products, fodder and particularly preferably pharmaceutical products.

Finally, the present invention relates to a method for preparing the afore-mentioned products comprising one of the above-described alternan manufacturing methods of the invention and the formulation of the thus obtained alternan in a form which is suitable for one of the afore-mentioned applications of the corresponding product.

These and other embodiments are disclosed and obvious to a skilled person and embraced by the description and the examples of the present invention. Additional literature regarding one of the above-mentioned methods, means and applications, which can be used within the meaning of the present invention, can be obtained from the state of the art, for instance from public libraries for instance by the use of electronic means. This purpose can be served inter alia by public databases, such as the "medline", which are accessible via internet. Other databases and addresses are known to a skilled person and can be obtained from the internet. An overview of sources and information regarding patents and patent application in biotechnology is contained in Berks, TIBTECH 12 (1994), 352–364.

Linear map of the entire sequence region which was cloned after the screening of a genomic library of *Leuconostoc mesenteroides* NRRL B 1355 by the corresponding overlapping fragments of the clones AS-19B1, AS-19B2, AS-28B and AS-29Ba.

Figure 2:
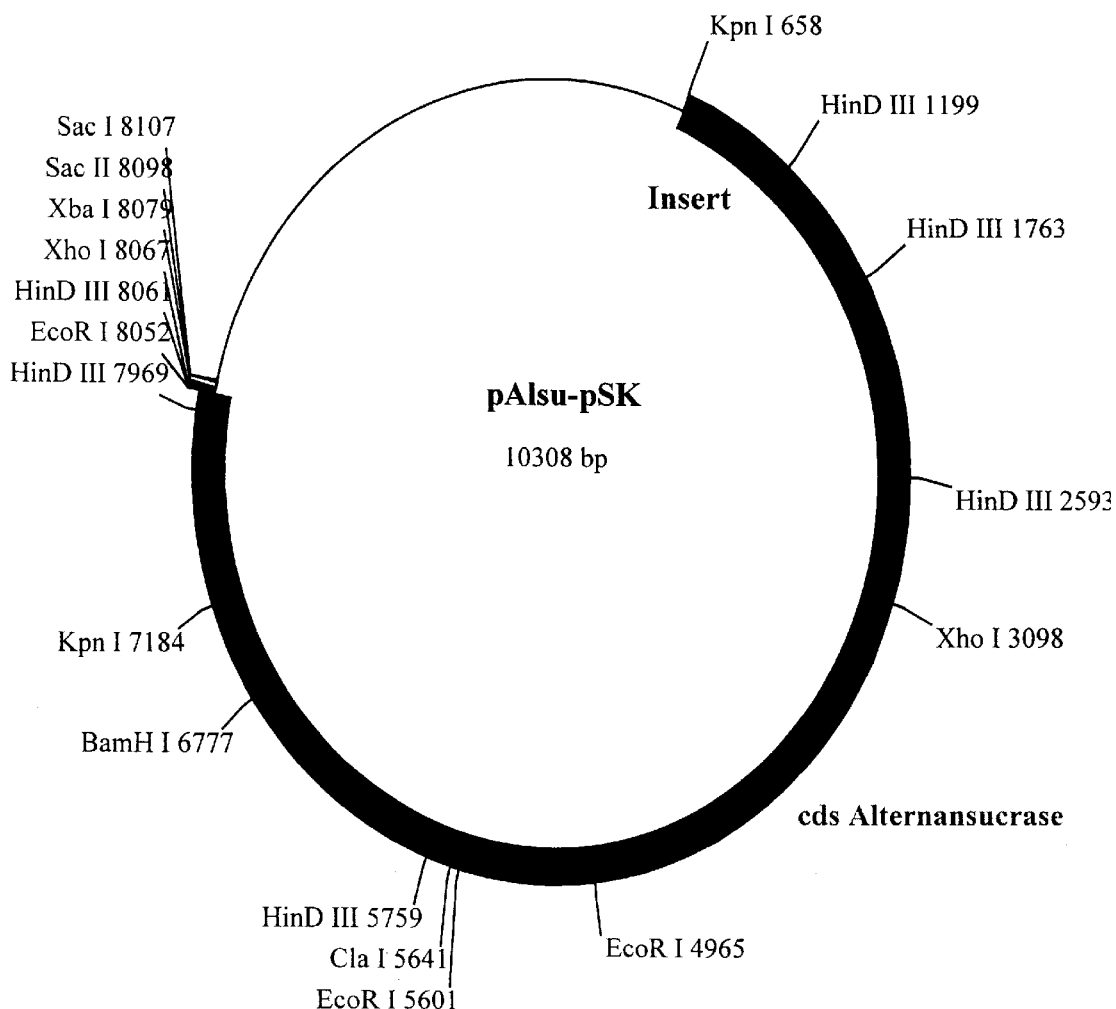
Figure 3:
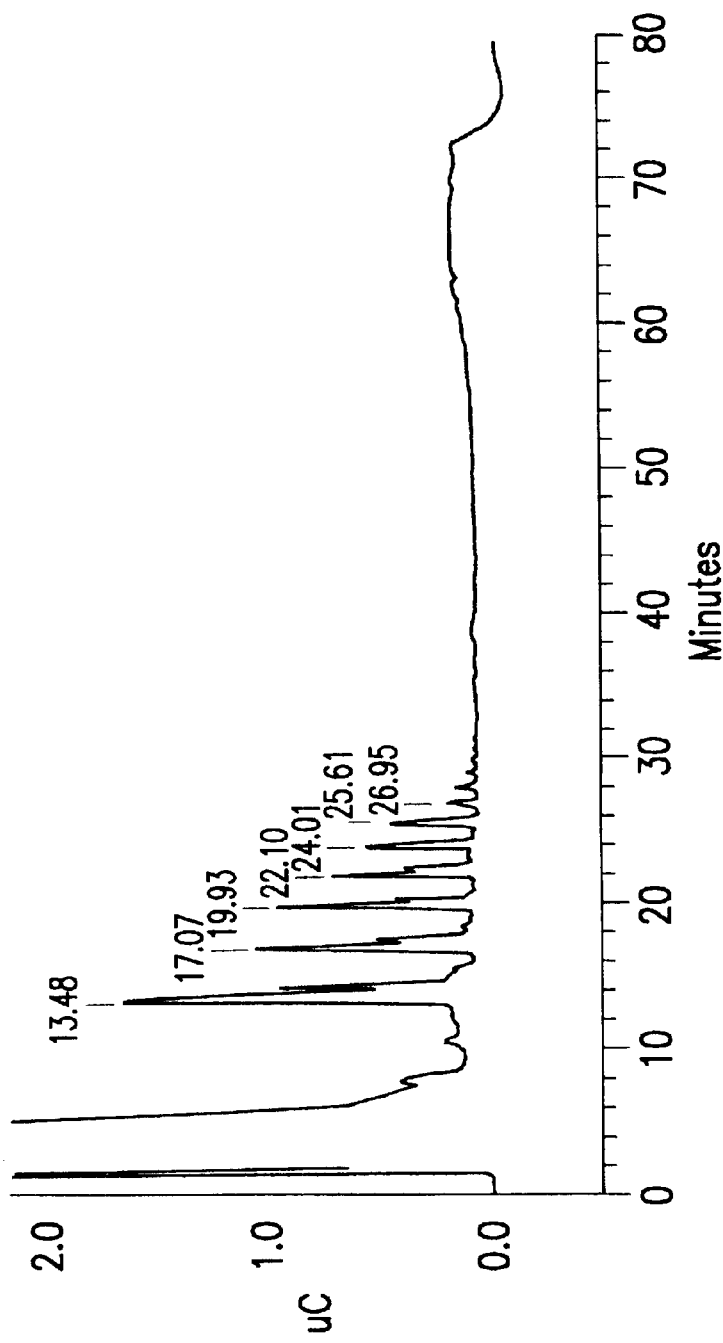
Figure 4:
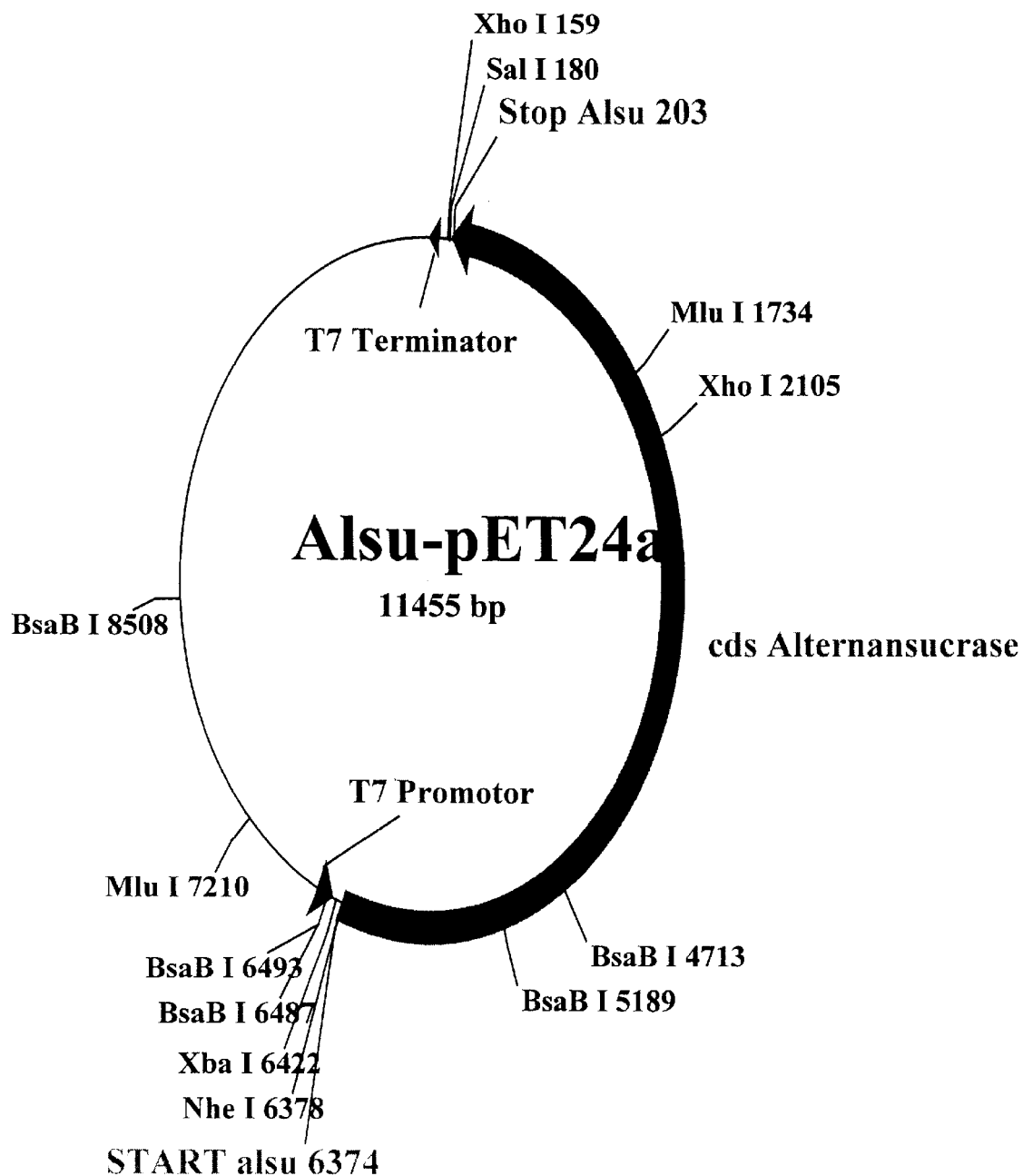

FIG. 2:
Plasmid map pAlsu-pSK
FIG. 3:
HPLC chromatogram: Preparation of oligoalternan in the presence of maltose (Example 2).
FIG. 4:
Plasmid map pAlsu-pET24a
FIG. 5:
SDS PAGE with subsequent assay of sucrase activity (see Example 6) The following protein extracts are used 1+2) *E. coli* BL21 (DE3) containing pAlsu-pET24a-3

3+4) *E. coli* BL21 (DE3) containing pAlsu-pET24a-7

5+6) *E. coli* BL21 (DE3) containing pAlsu-pET24a-21

Figure 6:
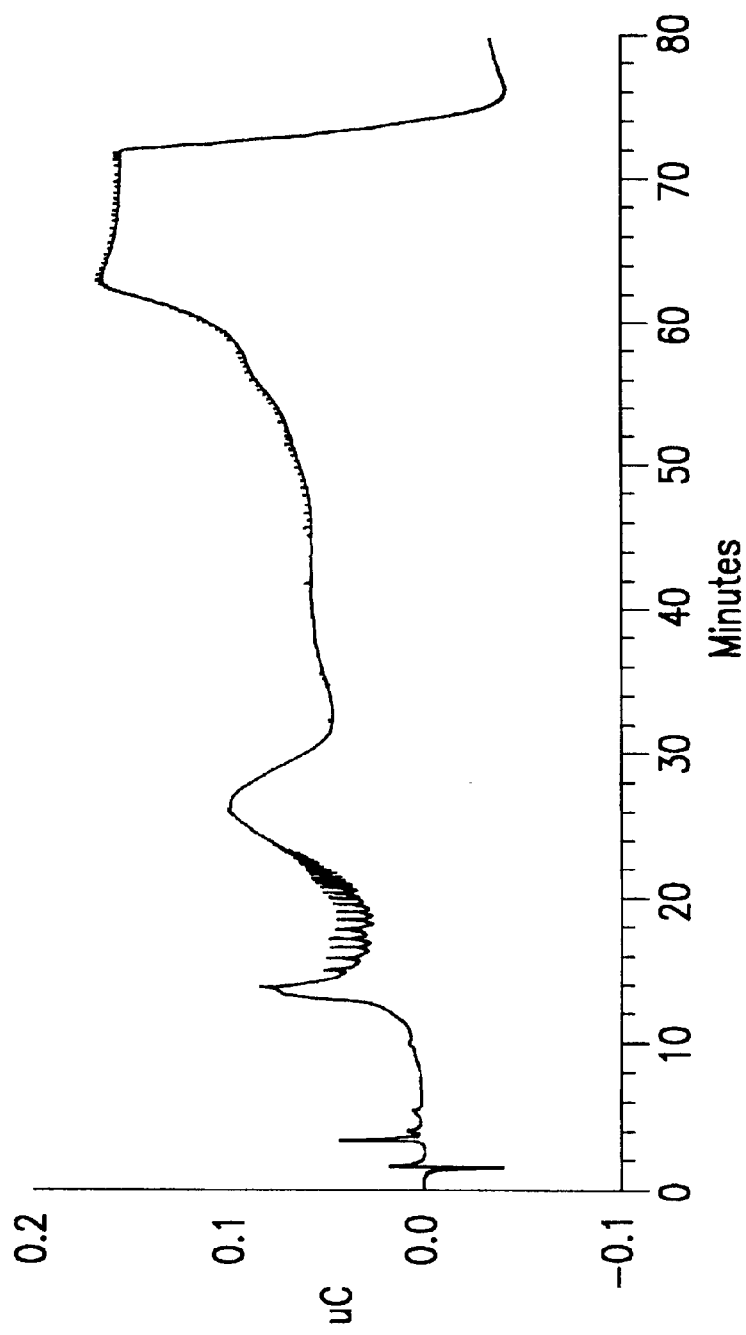
Figure 7:
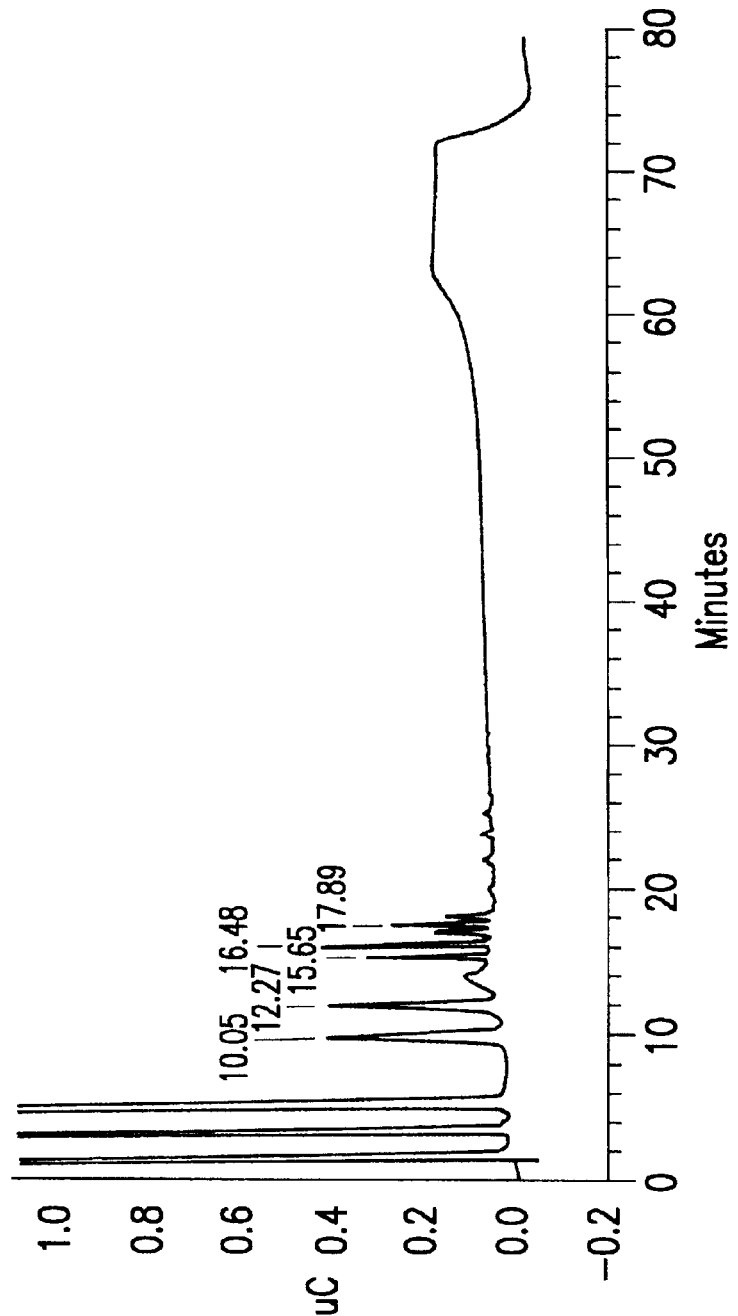
Figure 8:
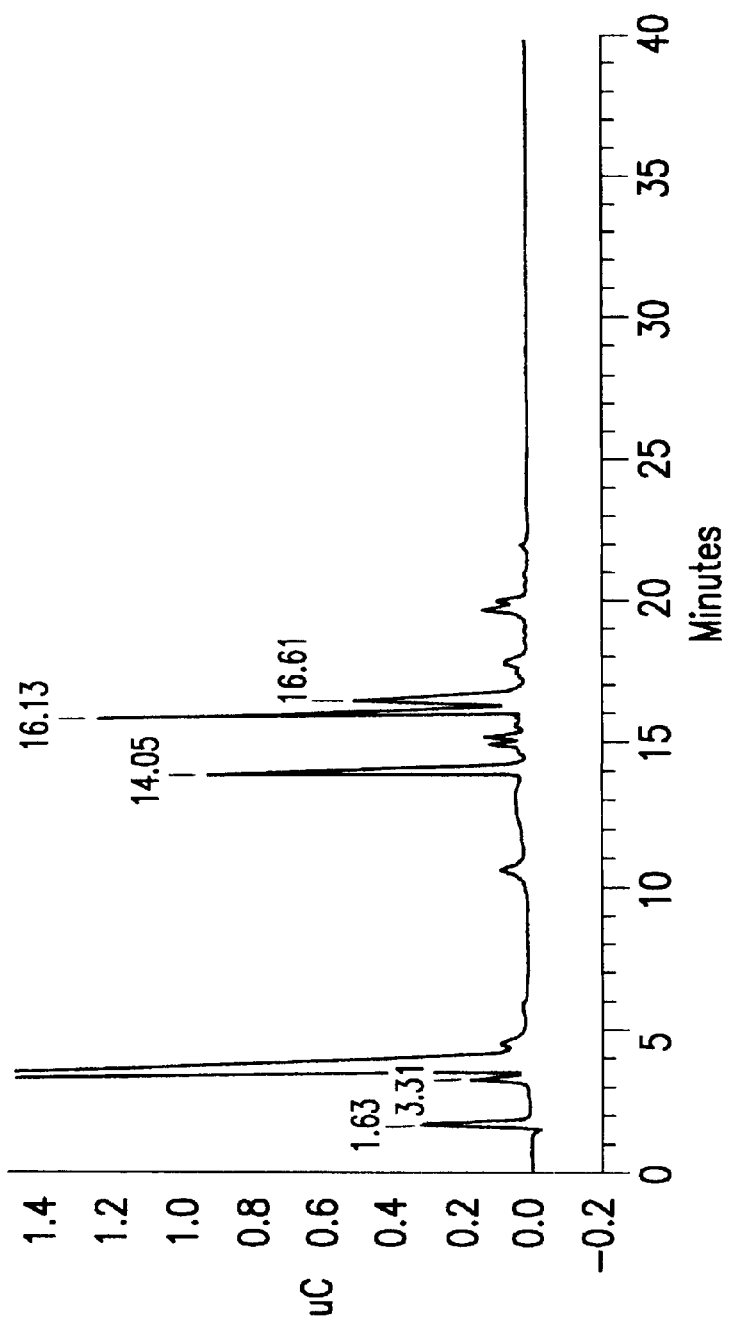
Figure 9:
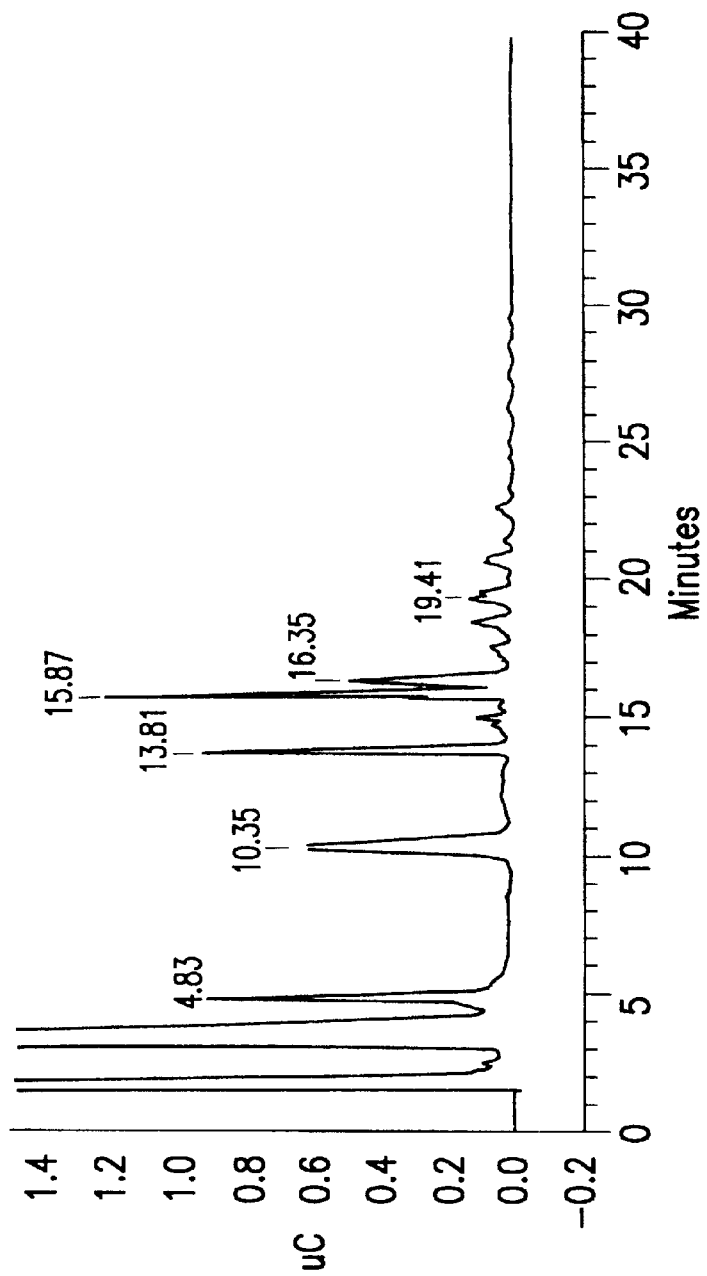
Figure 10:
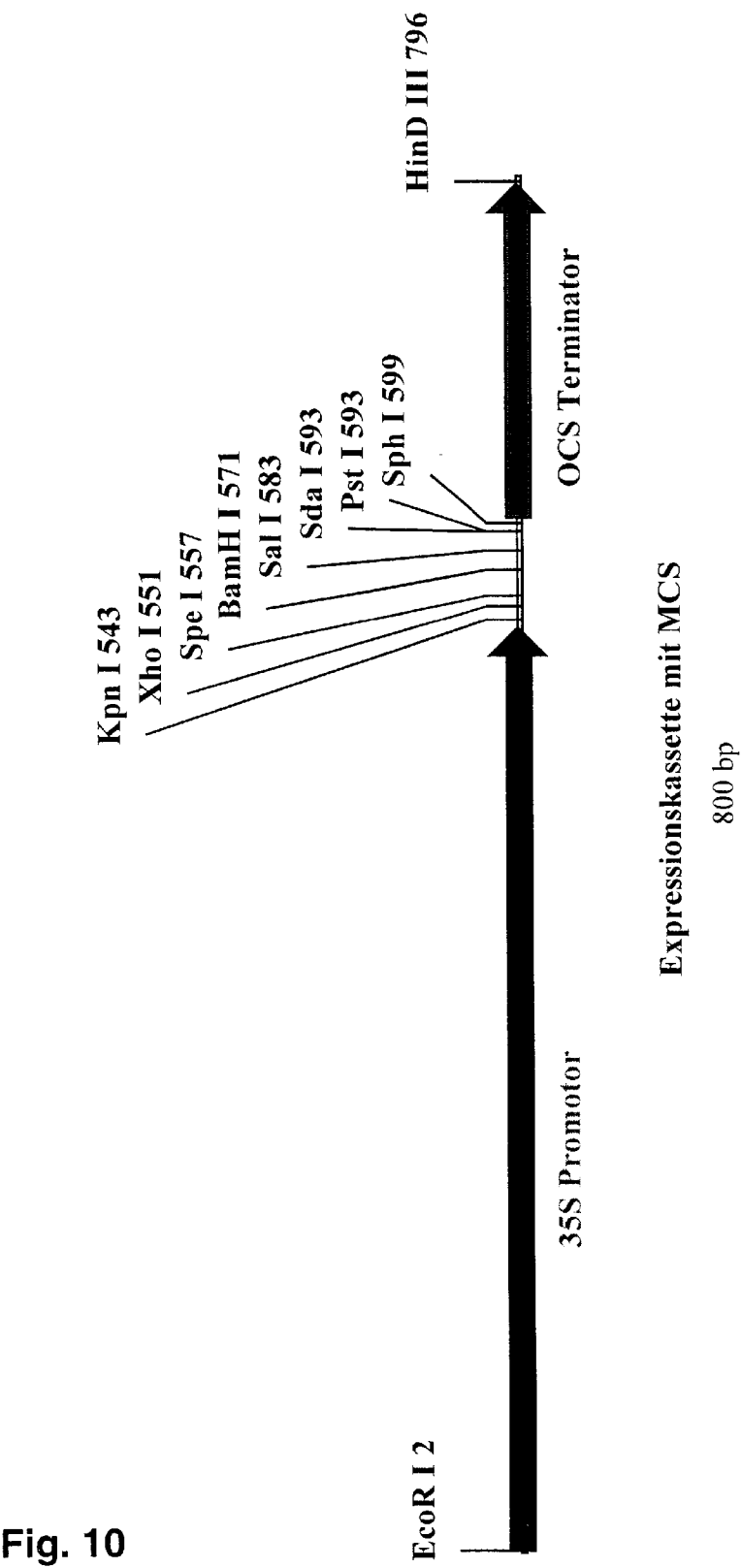
Figure 11:
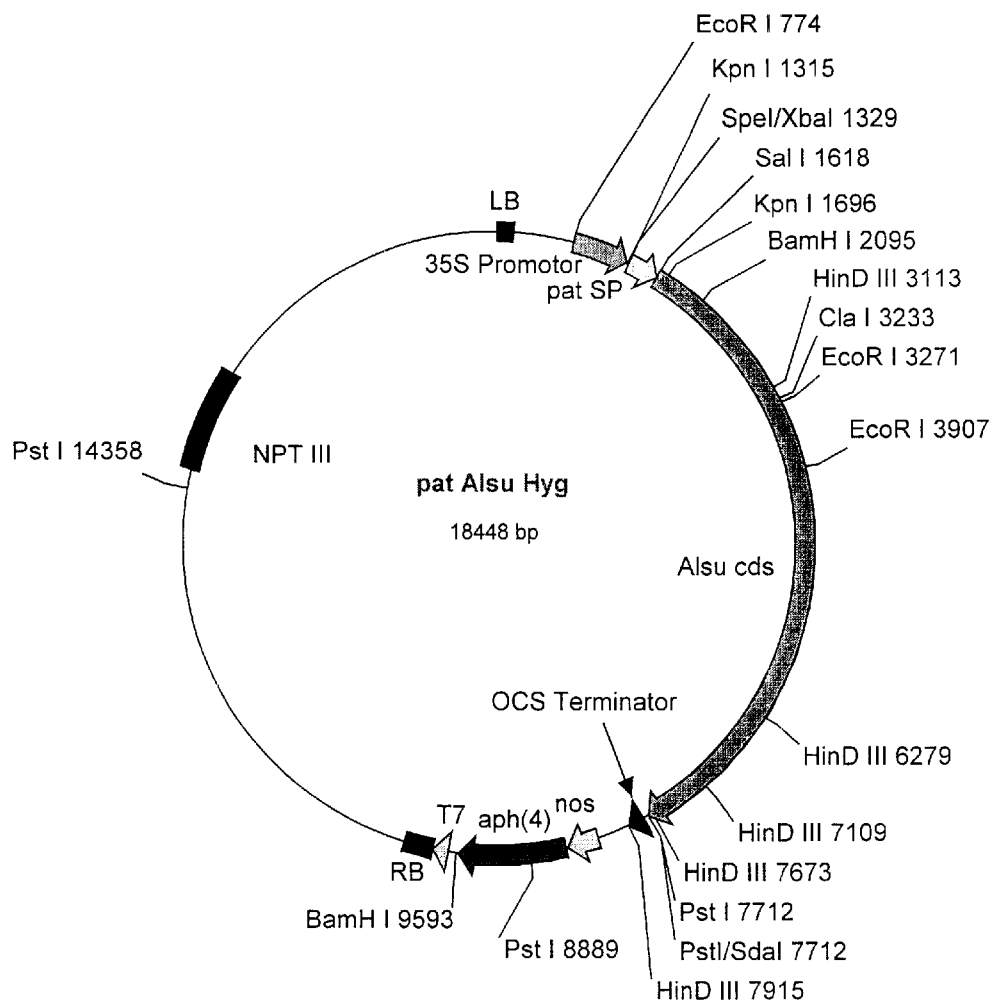
Figure 12:
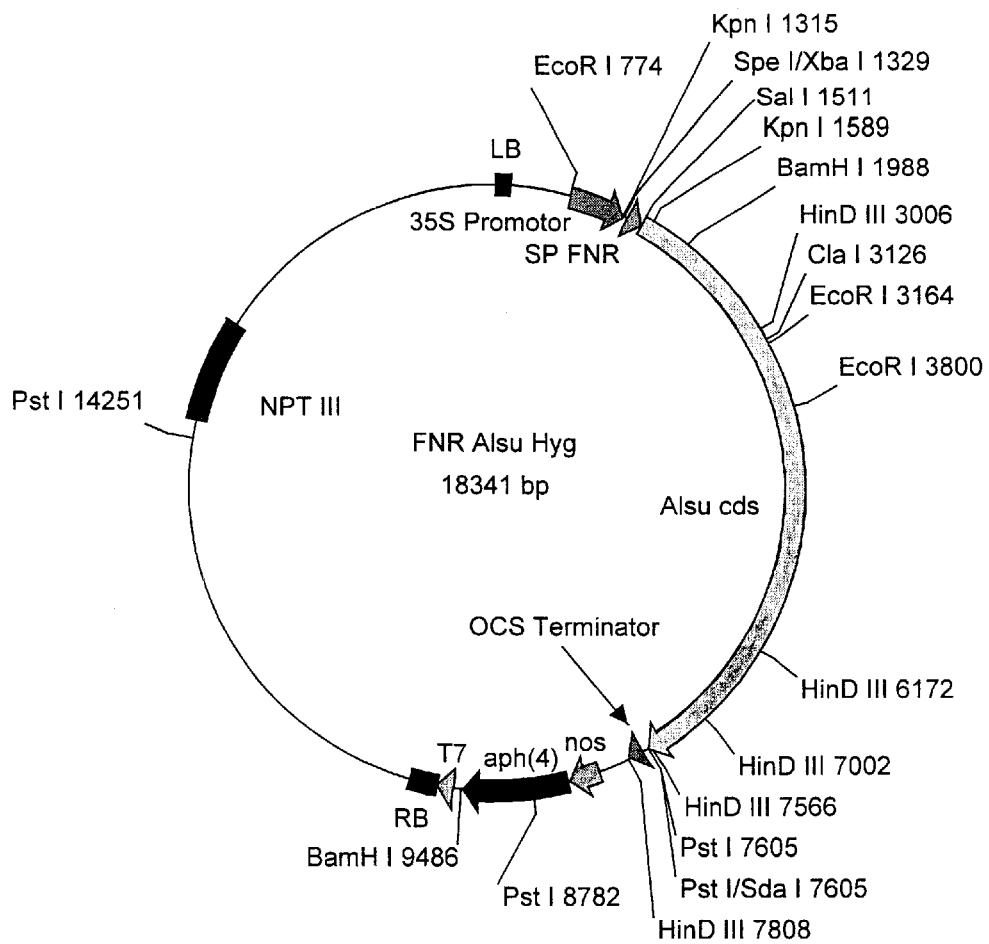

7+8) *E. coli* BL21 (DE3) containing pET24a 1, 3, 5, 7) culture before induction with IPTG 2, 4, 6, 8) culture at the end of culturing FIG. 6:
HPLC chromatogram of dextran T10
FIG. 7:
HPLC chromatogram of dextran T10 after dextranase digestion
FIG. 8:
HPLC chromatogram of oligoalternan
FIG. 9:
HPLC chromatogram of oligoalternan after dextranase digestion.
FIG. 10:
Map of the expression cassette including the polylinker of the plasmid pBinAR-N.
FIG. 11: Plasmid map pat-Alsu-Hyg.
FIG. 12:
Plasmid map fnr-Alsu-Hyg.

DETAILED DESCRIPTION OF THE INVENTION

EXAMPLES

Vectors used in the Examples:

1. pBinAR-N

By the use of standard methods (Sambrook et al., Molecular cloning: A laboratory manual, 2nd issue; Cold Spring Harbor Laboratory Press, N.Y., USA (1989)) we introduced a different polylinker (see FIG. 10) between the 35S Promoter and the OCS-Terminator into the plasmid pBinAR (H öfgen und Willmitzer, Plant Science 66 (1990), 221–230). The resulting plasmid was called pBinAR-N.

2. pBinAR-Hyg-N

Via standard methods (Sambrook et al., Molecular cloning: A laboratory manual, 2nd issue; Cold Spring Harbor Laboratory Press, N.Y., USA (1989)) we isolated an EcoRI/HinDIII-fragment from pBinAR-N containing the 35S Promoter, the polylinker and the OCS-Terminator. This fragment was then ligated into the same restriction sites of plasmid pBIB-Hyg (Becker, Nucleic Acids Research 18 (1990), 203). The resulting plasmid was called pBinAR-Hyg-N.

3. pBinAR-pat-Hyg

By using the oligonucleotides Sp-pat-5' and Sp-pat-3' (s. SEQ ID Nos. 48 and SEQ ID No. 49) we amplified DNA molecules coding for the leader peptide of the patatin protein from potato (see SEQ ID No. 50, which differs from the sequence used by Sonnewald et al. Plant J. 1 (1991), 95–106) via a PCR approach using plasmid pgT5 (Rosahl et al., Mol. Gen. Genet. 203 (1986), 214–220; Sonnewald et al., Plant J. 1 (1991), 95–106) as a template. The resulting PCR products were cut by the restriction enzymes Xbal and Sall and then ligated into the plasmid pBinAR-Hyg-N which was linearized before by using the restriction enzymes SpeI and Sall. The resulting plasmid was called pBinAR-pat-Hyg.

PCR Conditions:

Buffer and polymerase from Boehringer Mannheim (Pwo Polymerase No. 1644947)

| DNA | 0,2 ng |
|---|---|
| 10x Buffer + $MgSO_4$ | 5 µl |
| dNTPs (je 10 mM) | 1 µl |
| Primer Sp-pat-5' | 120 nM |
| Primer Sp-pat-3' | 120 nM |
| Pwo Polymerase | 1,0 units |
| Distilled water | ad 50 µl |

Reaction conditions:

| Step 1 | 95° C. | 2:30 min |
|---|---|---|
| Step 2 | 95° C. | 0:30 min |
| Step 3 | 64° C. | 0:30 min |
| Step 4 | 72° C. | 0:30 min |
|  | (plus 1 sec per cycle) | |
| Step 5 | 72° C. | 5:00 min. |

The steps 2 to 4 were repeated 35 times in a cyclical manner.

4. pBinAR-FNR-Hyg

By using the oligonucleotides Sp-fnr-5' and Sp-fnr-3 (see SEQ ID No. 51 and 52) we amplified DNA molecules coding for the transit peptide of the FNR protein from spinach via a PCR approach using plasmid p6SocFNR-15 (Jansen et al., Current Genetics 13, (1988), 517–522) as a template. The resulting PCR products were cut by Xbal and Sall and then cloned into the Spel/Sall-opened pBinAR-Hyg-N. Resulting plasmid was called pBinAR-fnr-Hyg.

PCR Conditions:

Buffer and polymerase from Gibco BRL (Platinum Taq DNA Polymerase High Fidelity No. 1304-011)

| DNA | 0,2 ng |
|---|---|
| 10x Buffer | 5 µl |
| MgSO4 | 2,0 µl |
| dNTPs (per 10 mM) | 1 µl |
| Primer Sp-fnr-5' | 150 nM |
| Primer Sp-fnr-3' | 150 nM |
| Taq Platinum Hifi Polymerase | 1,5 units |
| distilled water | ad 50 µl |

Reaction conditions:

| Step 1 | 95° C. | 2:30 min |
|---|---|---|
| Step 2 | 95° C. | 0:30 min |
| Step 3 | 58° C. | 0:30 min |
| Step 4 | 68° C. | 0:20 min |
|  | (plus 1 sec per cycle) | |
| Step 5 | 68° C. | 3:00 min |

The steps 2 to 4 were repeated 35 times in a cyclical manner.

Example 1

Cloning of Alternansucrase from *Leuconostoc Mesenteroides* NRRL-B1355

Isolation and Sequencing of Alternansucrase

The strain *Leuconostoc mesenteroides* NRRL-B1355 was cultured in 1 l of Lactobacilli MRS Broth (Difco) complemented with 5% saccharose at 28° C. for two days. After the culture was subjected to centrifugation at 20,000×g for 30 minutes, the supernatant was admixed with the same volume of 10% trichloro acetic acid and stirred at 4° C. for 16 hours. This solution was then subjected to centrifugation at 10,000×g for 30 minutes. The thus obtained precipitate was dissolved in 4.5 ml of 40 mM Tris-HCl, pH 8.8, and subsequently neutralized with (about 0.5 ml) 2 M Tris-base. This protein solution was given to the company Toplab Gesellschaft fur angewandte Biotechnologie mbH, Martinsried, Germany, for protein sequencing. At this company, the protein solution was electrophoretically separated in SDS polyacrylamide gel, the gel was stained with Coomassie Blue and the staining was subsequently removed by 10% acetic acid. For the enzymatic digestion of the protein, the protein bands were cut from the gel, pressed through a sieve and fragmented (pores 30 μm×100 μm). The crushed gel was then washed with half concentrated incubation buffer (12.5 mM Tris, 0.5 mM EDTA pH 8.5) for 2 minutes. Subsequently, it was subjected to centrifugation, the buffer was removed and the gel was dried in the "Speedvac" for one hour (about 5% residual water, rubber-like). Subsequently, a solution of endoproteinase LysC in 400 μl 12.5 mM Tris/HCl, pH 8.5 (enzyme: protein=1: 10) and 0.1% of laurylmaltosite was prepared. 200 μl of this solution were added to the sample and incubated in the heat block shaker at 37° C. overnight. In order to elute the peptide fragments, a one hour incubation with 1% TFA was carried out, twice, followed by centrifugation, and subsequently by elution with 10% formic acid, 20% isopropanol, 60% acetonitrile for 3 hours. The peptide fragments obtained were then separated from each other by HPLC (column Superspher 60 RP select B (Merck, Darmstadt) 2 mm×125 mm; buffer A 0.1% trifluoro acetic acid, buffer B: 0.085% TFA in acetonitrile; flow rate: 0.2 ml/min; gradient: 5–60% in 60 min; detection at 206 nm. The peptide fragments obtained were then sequenced in an automatic sequencer Procise 492 (Applied Biosystems, PE); the procedure being the stepwise Edman degradation in a modification according to Hunkapiller (Hunkapiller et al., Meth. Enzymol. 91 (1983), 399–413). Six different peptide sequences (see Seq. ID Nos. 5 to 9, Seq. ID No. 21) were identified which were designated lysC-66, IysC-67, lysC-82, IysC-83, lysC-88 and "N-terminus".

Preparation of a Genomic DNA Library from *Leuconostoc Mesenteroides* NRRL B1355

*Leuconostoc mesenteroides* NRRL-B1355 (purchased from ATCC) was cultured in 100 ml YT medium (Sambrook et al, loc. cit.) additionally containing 2% (w/v) of glucose and 50 mM sodium phosphate buffer pH 7.0, at 28° C. for 36 hours. After harvesting the cells by centrifugation, genomic DNA was isolated according to Ausubel et al. (Current Protocols in Molecular Biology, Volume 1, Greene and John Wiley & Sons (1994), USA).

100 μg of genomic DNA from *Leuconostoc mesenteroides* NRRL-B1355 were partially digested with 0.001 units of the restriction enzyme Sau3A for 30 minutes, subsequently extracted with phenol:chloroform:isoamyl alcohol. (25:24:1) and precipitated with ethanol. 2.5 μg of the partially digested DNA obtained from *Leuconostoc mesenteroides* NRRL-B1355 were ligated with T4 DNA ligase in 1 μg of the BamHl-cut and dephosphorylated vector pBKCM-VBamHl (Stratagene) under the conditions indicated by the manufacturer (Stratagene, pBK phagemid vectors instruction manual & T4 DNA ligase ligation kit). 2 μl of the ligation mixture were packaged with Gigapack III Gold (Stratagene) according to the instructions of the manufacturer and stored after the amount of phage content had been determined.

Preparation of the Probe for Isolating the Alternansucrase Gene

From the peptide sequences lysC-66 (Seq. ID No. 5), lysC-67 (Seq. ID No. 6), IysC-82 (Seq. ID No. 7), lysC-83 (Seq. ID No. 8) and lysC-88 (Seq. ID No. 9) obtained after tryptic digestion of the purified alternansucrase protein (see above) the peptides lysC-82 and lysC-83, after having undergone reverse translation, were selected for the synthesis of degenerated oligonucleotides (Seq. ID No. 10, Seq. ID No. 11). Said oligonucleotides served as primers in a PCR reaction on genomic DNA of NRRL-B1355. All positions within oligonucleotides depicted as N were replaced by inosin in the primer synthesis.

PCR Reaction Conditions

The reaction mixture was prepared with the buffers supplied for Taq polymerase (Company GibcoBRL). Reaction mixture:

| Taq Polymerase (Gibco) | |
|---|---|
| DNA | 100 ng (genomic NRRL-B1355) |
| DNTPs | 2.5 mM for each nucleotide |
| primer | 10 μl of a solution containing 0.2 μMol |
| 10 fold buffer | 5 μl |
| magnesium chloride | 2 mM |
| polymerase | 1 unit |
| water | ad 50 μl |
| Step 1 | 95° C. | 3' |
| Step 2 | 95° C. | 1' |
| Step 3 | 58° C. | 2' |
| Step 4 | 72° C. | 2' |
| Step 5 | 72° C. | 10' |

40 Repetitions of Steps 2 to 4

An 837 bp fragment (Seq. ID No. 12) resulting from this PCR reaction, the ends of which were blunted with T4 DNA polymerase, was cloned into the Smal-cut pBlueSkript vector (Stratagene). The resulting plasmid was designated pAlsu-PCR-lysc82/83. After sequencing of the insert and computer-aided translation into the corresponding protein sequences, a data base comparison was carried out in the Swiss Prot data base. This comparison showed homologies to known glycosyl transferases (P49331, P11001, P68987, P13470, P27470, P29336).

About 5,000 phages of the genomic DNA library of *Leuconostoc mesenteroides* NRRL-B1355 were plated out using the bacterial strains and nutrient solutions indicated by the manufacturer (Stratagene), and after incubation at 37° C. for 12 hours were transferred to nitrocellulose filters. This was followed by denaturation of the phages by immersion of the nitrocellulose filters in 1.5 m sodium chloride, 0.5 M caustic soda solution for 2 minutes and neutralization of the filters by immersion in 1.5 M sodium chloride, 0.5 M Tris-HCl, pH 8.0 for 5 minutes. After rinsing the filters in 0.2 M Tris-HCl, 2×SSC, the phage DNA was bound to the membranes by UV cross link (Stratalinker of the company Stratagene, 120,000 μJ for 30 seconds). The filters were incubated in a prehybridization solution (5×SSC, 0.5% BSA, 5×Denhardt, 1% SDS, 40 mM sodium phosphate buffer, pH 7.2, 100 mg/l herring sperm-DNA, 25% formamide) at 42° C. for 6 hours. 30 ng of the isolated insert from the plasmid pAlsu-PCR-lysc82/83 were radioactivley labeled by means of a multiprime kit (Boehringer Mannheim) using $\alpha$-$^{32}$p dCTP (ICN Biomedicals). This radioactive probe was added to the prehybridization mixture and the filters were incubated in this hybridization mixture at 42° C. overnight. After removal of the hybridization mixture the filters were washed three times in a washing solution (0.1×SSC, 0.5% SDS) at 55° C. for 15 minutes. An X-ray film (Kodak) was then placed on the filter for 18 hours. Phage colonies, producing hybridization signals, were identified, isolated, resuspended in SM medium and then again plated out in a dissolution such that they could be recognized as single plaques. After these phages were transferred to nitrocellulose filters and subjected to further treatment and hybridization under conditions as described above, hybridizing phages were obtained as individual isolates by means of the radioactive gene probe used. After in vivo excision of the isolated phages in accordance with the manufacturer's instructions (Stratagene) the clones AS-19B1 and AS-19B2 could be isolated as plasmids. After complete sequencing of both clones (Agowa) (Seq. ID No. 13, Seq. ID No. 14) both sequences showed an 1008 bp overlap. The joining of Seq. ID No. 13 with Seq. No. 14 followed by computer aided translation of all possible reading frames allowed a continuous reading frame, starting with the codon ATG (corresponding to the bases 678 to 680 in Seq. ID No. 1), to be identified. As no stop codon could be found in this composed reading frame, additional clones were isolated in order to obtain the complete coding sequence of alternansucrase.

Figure 1:
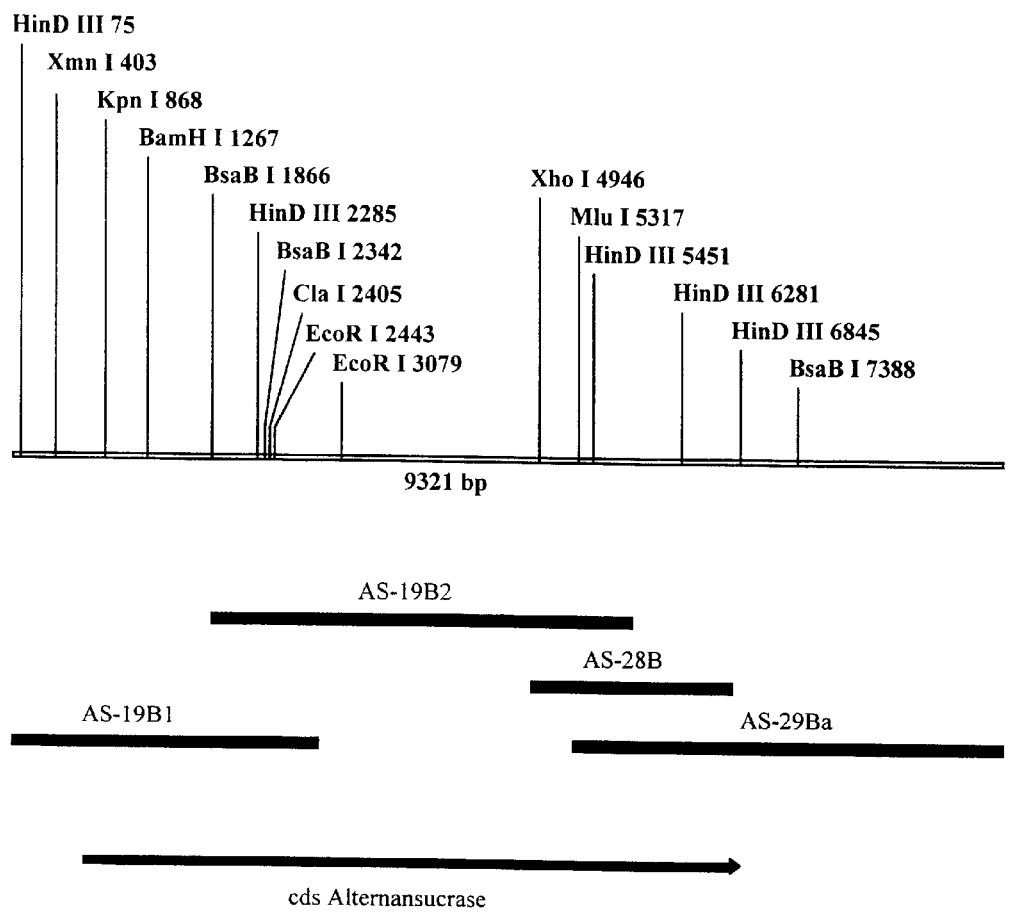
FIG. 1.

Therefore, about 5,000 phages of the genomic DNA library of *L. mesenteroides* NRRL-B1355 were again examined for hybridization by means of a clone AS-19B2 subfragment radioactively labeled using the multiprime kit (Boehringer Mannheim), as described above. The hybridization probe was prepared with the use of the HindIII (restriction site in the insert of AS-19B2)/SalI (cuts the pBKCMV phagemid vector in the polylinker)-fragment from AS-19B2. Said fragment contains 372 bases of the 3' end of the sequences encoding the above-described reading frame. The screening of the phage library, singling out, and transformation of the phages into plasmids was carried out under the above-described conditions. After complete sequence analysis of the thus isolated clones AS-28B (see Seq. ID No. 15) and AS-29Ba (Seq. ID No. 16) it was possible to identify an overlap of 960 identical bases (corresponding to bases 4863 to 5823 in Seq. ID No. 1) between clones AS-19B2 (Seq. ID No. 14) and AS-28B and an overlap of 567 identical bases (corresponding to bases 5256 to 5823 in Seq. ID No. 1) between clones AS-19B2 and AS-29Ba (Seq. ID No. 16). Clones AS-28B and AS-29Ba have 1523 identical bases (corresponding to bases 5256 to 6779 in Seq. ID No. 1). After computer-aided joining of clones AS-19B1, AS-19-B2 and AS-28B a continuous reading frame starting with codon ATG (bases 678 to 680 on the complete sequence) appeared. This reading frame also does not contain a stop codon. After the joining of clones AS-1 9B1, AS-1 9B2, AS-28B and AS-29Ba it was possible to identify a reading frame starting with the codon "ATG" (corresponding to bases 678 to 680 in Seq. ID No. 1) and ending with "TM" (corresponding to bases 6849 to 6851 in Seq. ID No. 1) encoding 2057 amino acids. In addition to the coding region, the entire isolated and identified DNA sequence of the composed clones (Seq. ID Nos. 13–16) contains 677 bases in the 5' region and 2469 bases in the 3' region which represent sequences not encoding alternansucrase (see FIG. 1).

Example 2

Construction of Plasmid pAlsu-pSK for the Transformation of *E. Coli* and Test of the Protein Extracts for Enzymatic Activity Plasmids AS-19B1, AS-19B2, AS-28B and AS-29Ba (see Example 1) were joined in the following manner: A NotI- (restriction site in the polylinker of vector pBK CMV, company Novagen)/ClaI-fragment of clone AS-19B1 was inserted into the vector pBluescript SK (company Stratagene) at the same restriction sites (=first cloning step). Consecutive insertion of the ClaI/XhoI fragment from AS-19B2, XhoI/MluI fragment from AS-28B and MluI/BsaBI (BsaBI-cut fragment cloned into the blunted ApaI restriction site of the vector) fragment of AS-28B into the clone obtained from the first cloning step produced plasmid pAlsu-pSK (see FIG. 2). This plasmid contains the complete coding sequence of the alternansucrase from *Leuconostoc mesenteroides* NRRL-B1355 as well as non-coding sequences of 677 bp (promoter region) in the 5' region and 539 bp in the 3' region (Seq. ID No. 17).

Plasmid pAlsu-pSK was then transformed in *E. coli* (DH5α company Fermentas). The bacteria were then cultured at 27° C. for two days in 50 ml "Terrific broth" (the composition of which is described in Sambrook et al., Molecular Cloning, A Laboratory Manual, $2^{nd}$ edition (1989) Cold Spring Harbor Laboratory Press, Cold Spring Harbor, N.Y. (supplemented with 0.5% glucose) or in a fermentation medium having the following composition: $KH_2PO_4$ 1.5 g/l, $(NH_4)_2SO_4$ 5.0 g/l, NaCl 0.5 g/l, Na-citrate 1.0 g/l, $Fe^{2+}SO_4 \times 7$ $H_2O$, 0.075 g/l, yeast extract 0.5 g/l, tryptone 1.0 g/l, glucose 15.0 g/l, $MgSO_4 \times 7$, $H_2O$ 0.3 g/l, $CaCl_2 \times 2$ $H_2O$ 0.014 g/l, mineral salts 10 ml/l, $H_3BO_3$ 2.5 g/l, $CoCl_2 \times 6$ $H_2O$ 0.7 g/l, $CuSO_4 \times 5$ $H_2O$ 0.25 g/l, $MnCl_2 \times 4$ $H_2O$, 1.6 g/l, $ZnSO_4 \times 7$ $H_2O$ 0.3 g/l, $Na_2MoO_4 \times 2$ $H_2O$ 0.15 g/l, vitamin B1 (thiamine) 0.005 g/l.

All cultures contained 100 mg/l ampicillin. The cells were then harvested by centrifugation, resuspended in 2 ml 50 mM Na-phosphate buffer pH 7.2 and crushed by a French Press. Subsequently, they were again subjected to centrifugation to remove solid particles of the crushed cells, and the supernatant (hereinafter referred to as (protein) extract) was used after sterilfiltration (Sterivex GV 0.2 μm, millipore) for further analyses.

In vitro Preparation of Alternan by Means of Protein Extracts

For the in vitro preparation of alternan, 200 μl each of the extracts obtained were examined in 2 ml each of 100 mM Na-citrate buffer pH 6.5 and 20% (w/v) saccharose for activity in the presence and absence of 100 μl of 10 mM maltose. The reaction mixture was incubated at 37° C. for 24 hours. In the subsequent precipitation with the same volume of ethanol in the absence of maltose no precipitable polymer was found. In the batch containing maltose, HPLC chromatography (Dionex PA-100 column, running buffer 150 mM NaOH, elution buffer 150 mM NaOH+3 M sodium acetate buffer gradient) showed the formation of oligomers (see FIG. 3).

Activity Gel 20 ml each of the individual protein extracts were applied to a 6% SDS-PM gel and separated at a current strength of 20 mA per gel. (Before application to the gels, the extracts were not incubated at 95° C.). Subsequently, the extracts were examined for sucrase activity according to the method of Miller and Robyt (Analytical Biochemistry 156 (1986), 357–363).

The control (dextransucrase NRRL-B-512F, see Example 3 for its preparation) showed polymerizing activity. The protein extracts of the above-described *E. coli* cells containing the plasmid pAlsu-pSK, did not show any polymer-forming activity.

Example 3

Cloning and Expression of Dextransucrase from Leuconostoc Mesenteroides NRRL-B512F Isolation of Genomic DNA Leuconostoc mesenteroides NRRL-B512F (obtained from ATCC) was cultured at 28° C. for 48 hours in YT-medium (Sambrook et al., Molecular Cloning: A Laboratory Course Manual, $2^{nd}$ edition (1989), Cold Spring Harbor Press, New York) additionally containing 1 % of saccharose and 50 mM sodium phosphate buffer pH 7.0. After harvesting the cells by centrifugation, genomic DNA was isolated according to Ausubel et al. (Current Protocols in Molecular Biology, Volume 1, Greene and John Wiley & Sons (1994), USA).

PCR Amplification of the Dextransucrase Gene and Cloning in pET24a

For the recombinant expression of dextransucrase in *E. coli*, the gene encoding dextransucrase was cloned in the expression vector pET24a (Novagen) after PCR amplification. For this purpose, an EagI restriction site was introduced at the 5' end of the sequences encoding the dextransucrase and an XhoI restriction site at the 3' end, together with the PCR primers used (5'b512-1: 5'-ACTgCggCCgCATgCCATTTACAgAAAAAg-3'; Seq. ID No. 3 and 3'b512: 5'-ACTgCTCgAgTTATgCTgACACAgCATTTC-3'; Seq. ID No. 4) derived from the sequence of WO 89/12386. Subsequent cloning into the corresponding restriction sites of the polylinker of pET24a was carried out. The resulting plasmid was designated UL5–20.

PCR Reaction Conditions

Buffer and polymerase of the company Gibco BRL were used.

| DNA: | 100 ng (genomic NRRL-B512F) |
|---|---|
| 10 fold buffer | 5 µl |
| MgCl2 | 4 mM |
| 5' primer | 50 ng |
| 3' primer | 50 ng |
| dNTP | 1 mM of each nucleotide |
| Pfu polymerase | 0.5 units |
| water | ad 50 µl |
| step 1 | 95° C. | 4 minutes |
| step 2 | 95° C. | 1 minute |
| step 3 | 55° C. | 1 minute |
| step 4 | 72° C. | 5 minutes |
| step 5 | 72° C. | 10 minutes |

40 repetitions were made between steps 2 and 4.

Preparation of Recombinant Dextransucrase

B21(DE3) *E. coli* cells containing the plasmid UL5–20 were cultured in YT medium (see above) at 37° C. up to an OD $_{600}$=0.8. Subsequently, the cells were subjected to induction with 0.2 mM IPTG and cultured anew at 18° C. for 24 hours. After harvesting the cells by centrifugation and resuspending them in sodium phosphate buffer, pH 5.2, the cells were crushed in a French Press. The solution obtained was freed from insoluble components by centrifugation and the supernatant containing dextransucrase and referred to hereinafter as the extract was obtained.

Example 4

PCR Amplification of the Coding Region of Alternansucrase and Cloning in pET24a The coding region of alternansucrase was amplified in a PCR reaction (see the reaction conditions below) with genomic DNA from the *Leuconostoc mesenteroides* strain NRRL-B1355 as a template. An NheI restriction site was introduced at the 5' end by means of primers A1–4 (Seq. ID No. 18), and a SalI-restriction site at the 3' end by means of primer Al-5 (Seq. ID No. 19). A fragment of about 6200 bp was isolated.

A1–4: 5'-GGG CCC GCT AGC ATG AAA CM CM GAA ACA GT

A1–5: 5'-CCC GGG GTC GAC CTT TGT CGA ATC CTT CCC

Reaction conditions of the PCR (kit of the company Gibco BRL):

DNA 1 µl
10×buffer 5 µl
10 mM per dNTP 2 µl
50 mM MgSO$_4$ 2 µl
primer per 1 µl
Platinum DNA polymerase 0.2 µl
distilled water 37.8 µl
step 1 95° C., 2 minutes
step 2 95° C., 20 seconds
step 3 47° C., 20 seconds
step 4 68° C., 7 minutes (prolonged by 3 seconds per cycle)
step 5 68° C., 15 minutes Steps 2 to 4 were repeated 35 times altogether before step 5 was carried out.

The PCR fragment obtained was purified according to standard methods, treated with the restriction endonucleases NheI and SalI, ligated into vector pET24a (of the company Novagen) which had likewise been cut with these enzymes, and the ligation product was transformed into *E. coli*. After preparation of the plasmid and restriction digestion, three positive clones were selected. They were designated pAlsu-pET24a-3, pAlsu-pET24a-7 and pAlsu-pET24a-21 (see FIG. 4), respectively. All contained the sequence indicated in Seq. ID No. 20 as an insertion.

Example 5

Expression of the Recombinant Alternansucrase in *E. Coli* in Shake Flask Cultures and in the Fermenter Shake Flask Culture Plasmids pAlsu-pET24a-3, pAlsu-pET24a-7, pAlsu-pET24a-21 and pET24a were transformed into *E. coli* BL21 (DE3), of the company Novagen, and after initial culturing at 37° C. for 3 hours in 3 ml YT medium (Sambrook et al., Molecular Cloning, A Laboratory Manual, $2^{nd}$ edition (1989), Cold Spring Harbor Laboratory Press, Cold Spring Harbor, N.Y.) they were each cultured in shake flasks in 2 replicas in 50 ml Davis minimal medium (DIFCO Manual, Dehydrated Culture Media and Reagents for Microbiology, $10^{th}$ edition, Detroit Mich., USA (1984)) containing 0.2% glucose instead of dextrose as a carbon source at 37° C. until an OD$_{600}$ of about 0.8 was reached. After centrifugation and resuspension, one of the two replica cultures was cultured in Davis Minimal Medium (DMA) containing 1% lactose as the carbon source and inductor at 27° C. for another 16 hours. The cells of the individual cultures were harvested after centrifugation, resuspended in 50 mM sodium acetate buffer pH 5.3, and a protein extract was prepared as described in Example 2.

Fermenter

Clone pAlsu-pET24a-21 transformed in *E. coli* BL21 (DE3) was cultured in a 2 l fermenter (Biostad B; B.Braun, Melsungen) under the following conditions:

Medium:

Fermentation medium: $KH_2PO_4$ 1.5 g/l, $(NH_4)_2SO_4$ 5.0 g/l, NaCl 0.5 g/l, Na-citrate 1.0 g/l, $Fe^{2+}SO_4 \times 7\ H_2O$ 0.075 g/l, yeast extract 0.5 g/l, tryptone 1.0 g/l, glucose 15.0 g/l, $MgSO_4 \times 7\ H_2O$ 0.3 g/l, $CaCl_2 \times 2\ H_2O$ 0.014 g/l, mineral salts 10 ml/l, $H_3BO_3$ 2.5 g/l, $CoCl_2 \times 6\ H_2O$ 0.7 g/l, $CuSO_4 \times 5\ H_2O$ 0.25 g/l, $MnCl_2 \times 4H_2O$ 1.6 g/l, $ZnSO_4 \times 7\ H_2O$ 0.3 g/l, $Na_2MoO_4 \times 2\ H_2O$ 0.15 g/l, vitamin B1 (thiamine) 0.005 g/l.

Carbon source: Glucose (1.5% (w/v)) is present in the medium, 70% (w/v) glucose solution is added.

Automatic pH control by ammonia and phosphoric acid at pH 7.0+/−0.1. A 20% concentration of $pO_2$ is adjusted in the medium via control by the stirrer.

Conditions:

1.5 l of fermentation medium were inoculated with 50 ml of the preculture. The cells were first cultured at 37° C. until the glucose present was consumed. They were then cultured at the same temperature at a feeding rate of 9 g of glucose $\times l^{-1} \times h^{-1}$ until an $OD_{600}$=40 was reached. At this time, the temperature of the culture broth was lowered to 20° C. and the amount of glucose addition was lowered to $2\ g \times l^{-2} \times h^{-1}$. At a culture temperature of 20° C., the culture was subjected to induction with 0.2 mM IPTG (isopropyl-β-D-thiogalactopyranoside (Sigma)). After culturing at 20° C. for another 18 hours, the cells were harvested by centrifugation, resuspended in 50 mM sodium phosphate buffer pH 5.3 and an extract was prepared as described in Example 2.

Example 6

SDS PAGE Assay of the Activity of the Recombinant Alternansucrase, Periodic Acid Oxidation and Staining According to Schiff Protein extracts were prepared from *E. coli* shake flask cultures (strain BL21 (DE3)), containing the plasmids pAlsu-pET24a-3, pAlsu-pET24a-7, pAlsu-pET24a-21 and pET24a (control), respectively. Two different extracts were each prepared from the cells transformed with the different extracts, one of said extracts being prepared before induction with IPTG and the other one being prepared after induction with IPTG at the end of culturing. The activity of these extracts of shake flask cultures (see Example 5) was detected by SDS PAGE separation of the proteins, followed by SDS removal by washing with 50 mM sodium acetate buffer pH 5.3 and incubation of the gels in 50 mM sodium acetate pH 5.3, 5% (w/v) saccharose at 37° C. for 16 hours, followed by periodic acid oxidation of the polymer formed and staining by means of acidic Schiff reagent (Miller and Robyt, Analytical Biochemistry 156, (1986), 357–363).

Figure 5:
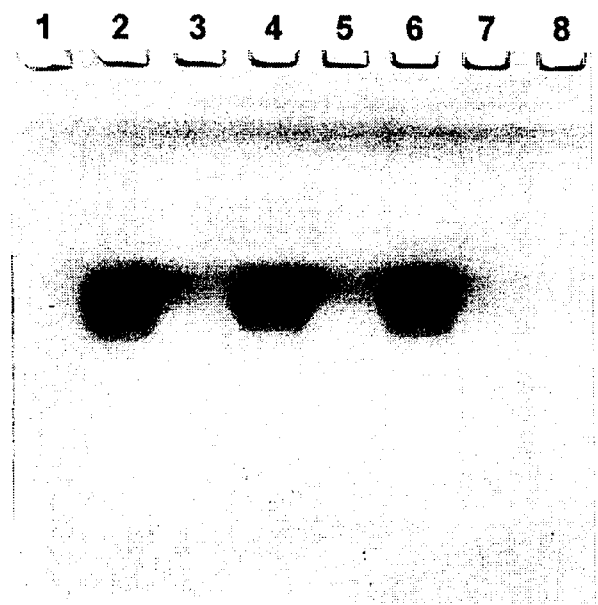

FIG. 5 shows that sucrase activity has not been found for either one of the extracts (preparation of the extract before and after IPTG-induction) containing the cloning vector pET24a. In the case of strains which had been transformed with the plasmids pAlsu-pET24a-3, pAlsu-pET24a-7 and pAlsu-pET24a-21, respectively, all protein extracts showed sucrase activity at the end of the induction phase (concentrated in one band).

Before induction with IPTG such activity bands were not found.

As the polymer formed in the gel can be stained according to the above-described methods by acidic Schiff reagent, it can be assumed not to be composed of pure α-1,3-linked units which would not lead to any staining.

As the gene contained in vectors pAlsu-pET24a-3, pAlsu-pET24a-7 and pAlsu-pET24a-21, respectively, was isolated from the *Leuconostoc mesenteroides* strain NRRL-B1355 which expresses at least one dextran sucrase apart from alternansucrase, it was not possible to determine unambiguously with this staining method whether the nucleic acid sequence contained in the plasmid actually encodes an alternansucrase. Dextrans and alternans can both be detected by this method because both polymers contain α-1,6 linkages.

Example 7

Tests for the Enzymatic Activity of Recombinantly Prepared Alternansucrases after Heat Treatment and for the Specificity of Alternansucrase In order to prove polymerization activities, extracts from shake flask cultures were used (see Example 5). 100 μl of extract were each added to 2 ml reaction buffer (50 mM sodium acetate pH 5.3, 20% saccharose) and incubated at 37° C. for 24 hours. For comparison, an extract inactivated by a 10 minute treatment at 95° C., and an extract from *E. coli* BL21(DE3) containing vector pET24a were used. Polymer formation was only found in the batch that had not been inactivated, while the batch treated at 95° C. for 10 minutes and the batch with the extract from BL21 (DE3) containing pET24a did not show any polymer formation. After addition of the same volume of absolute ethanol to all batches, polymers could only be precipitated from the batch which had not been inactivated. This finding is a clear indication of the activity of alternansucrase, because the dextransucrase present in NRRL B-1355 is inactivated by a treatment at 45° C. for 30 minutes, while alternansucrase remains active under these conditions (Lopez-Munguia et al., Enzyme Microb. Technol. 15 (1993), 77–85). The enzymatic assay by a coupled enzymatic test of the glucose and fructose released and of the saccharose still contained in the reaction mixture after 24 hours, respectively, revealed that fructose was only present in the extract that was not inactivated.

For carrying out the enzymatic test either purified protein or crude protein extract is added in different dilutions to 1 ml batches containing 5% saccharose and 50 mM acetate, pH 5.5 and subjected to incubation at 37° C. After 5 minutes, 10 minutes, 15 minutes, 20 minutes, 25 minutes and 30 minutes, 10 μl each are removed from these batches and the enzymatic activity of alternansucrase is terminated by immediate heating to 95° C. Subsequently, in the coupled photometric test, the portions of fructose and glucose released by alternansucrase and the portion of used-up saccharose, respectively, are determined. For this purpose, 1 μl to 10 μl of the inactivated sample are placed into 1 ml of 50 mM imidazole buffer, pH 6.9, 2 mM $MgCl_2$, 1 mM ATP, 0.4 mM AND and 0.5 U/ml hexokinase. After sequential addition of about 1 u of glucose-6-phosphate dehydrogenase (from *Leuconostoc mesenteroides*), about 1 u of phosphoglucose isomerase and about 5 u of invertase, the alteration of adsorption at 340 nm is measured. Subsequently, the amount of fructose and glucose released and used-up saccharose, respectively, is calculated according to the Lambert-Beer law.

In control batches (inactivation of the extract by treatment with 95° C. and extract from *E. coli* containing pET24a) no significant release of fructose and no decrease of saccharose, respectively, was found in the reaction batch after 24 hours.

These results confirm that the specificity of the sucrase encoded by plasmids pAlsu-pET24a-3, pAlsu-pET24a-7 and pAlsu-pET24a-21, respectively, is that of a glucosyltransferase. The specificity of a fructosyl transferase, the presence of which has been described for some strains of the genus Leuconostoc is to be excluded, because otherwise glucose should have been found.

Example 8

Production of Alternan by Means of Alternansucrase Prepared in *E Coli*

100 ml of extract obtained by fermentation of *E. coli* BL21(DE3) containing plasmid pAlsu-pET24a-3 (see Example 4) were added to 900 ml of reaction buffer (50 mM sodium acetate pH 5.3, 20% saccharose) and incubated at 37° C. for 24 hours. The addition of the same amount of absolute ethanol to the reaction mixture caused the alternan formed to precipitate. After the precipitate was washed twice with 50% ethanol, it was dried by lyophilization. The yield of dried polymer based on the amount of saccharose used in the reaction was 60%.

Example 9

HPLC Analysis of Alternan and Dextran After Dextranase Digestion 100 mg of the polymer prepared in Example 7 and 100 mg of dextran T10 (Pharmacia) were each dissolved in 1 ml of water. 40 µl each of these solutions were added to 700 µl reaction buffer (50 mM potassium phosphate pH 5.7, 8 units of dextranase, ICN Biomedicals Inc. No. 190097), and incubated at 37° C. for 16 hours. 50 µl of the polymer solutions not treated with dextranase (see FIG. 6) and 50 µl of the polymer solutions treated with dextranase (FIG. 7) were analyzed by HPLC (Dionex, column PA-100, NaOH/NaOH-NaAc gradient).

In the case of dextran T10 the cleavage of the polymer into different molecules of lower molecular weights can be clearly seen. The entire high molecular weight dextran is converted by dextranase into smaller units (mostly isomaltose). By contrast, in the case of alternan, short chained oligosaccharides only appear in small amounts after dextranase incubation. Most of the alternan is not digestible by dextranase. This finding suggests that the product prepared by recombinant alternansucrase is not dextran, but alternan which is known to be hardly accessible to enzymatic digestion by dextranase (Lopez-Mungia et al., Enzyme Microb. Technol. 15, (1993), 77–85).

Example 10

In vitro Preparation of Alternan in the Absence of Dextranase

100 µl extract from shake flask cultures (see Example 5) were added to 2 ml of reaction buffer (50 mM sodium acetate, pH 5.3, 20% saccharose). 50 units of dextranase (Biomedicals Inc. No. 190097) were additionally added to another batch. Two corresponding batches which contained dextransucrase from *Leuconostoc mesenteroides* NRRL-B512F instead of the enzyme extract served as controls; one of these two batches had dextranase additionally admixed to it.

After precipitation with ethanol, the reaction batch with dextransucrase and dextranase did not show any polymer formation. All other batches were found to show polymer formation.

Example 11

In vitro preparation of Oligoalternan and HPLC Analysis

Oligoalternan was prepared as described in Example 2, with a protein extract in the presence of maltose and was subsequently detected (See FIG. 8) by HPLC-chromatography (see Example 2). For comparison, a portion of this batch was admixed with 50 units of dextranase (Biomedicals Inc. 190097) after preparation of oligoalternan and subsequently separation by HPLC chromatography was carried out as well (see FIG. 9). A comparison of the two chromatograms shows that not only the height of the two peaks which can be allocated to the oligoalternan (α and β-anomer) (retention time between 15.87 and 16.61 minutes) but also the height of all the other peaks, the first signs of which are already visible without dextranase, remain unchanged. This finding suggests that recombinantly prepared alternansucrase allows oligoalternan to be prepared without the simultaneous production of oligodextran. Oligodextran would be liable to digestion by dextranase, which would have to show up in a decrease of the height of the peaks in the HPLC chromatogram, if oligodextran were present.

Example 12

Methylation Analysis of Alternan

In order to further analyze the alternan produced in vitro a methylation analysis was carried out:
Permethylation The permethylation was performed as described by Ciucanu and Kerek (Carbohydr. Res. 131 (1984), 209–218) by using NaOH/MeI in DMSO or by using a modified method according to Hakomori (Journal of Biochemistry 55 (1964 FEB), 205–208) which relies on the use of freshly prepared Li-Dimsyl/MeI (Dimsyl=methylsulfinyl carbanion) in DMSO at room temperature.

All reactions are performed under a nitrogen atmosphere. The permethylation products are isolated by extracting the excess of methyliodide by the use of dichlormethan. DMSO and salts were washed out at the end.
Degradation into Partially Methylated Sorbitacetates (Methylation Analysis)

The permethylated glucans were hydrolyzed with 2N trifluorine acetic acid at 120° C. for 1–3 hours. After cooling the acid was removed by nitrogen. Then the resulting glucans were co-distilled with a small amount of toluene, afterwards reduced by $NaBD_4$ in 1N ammonia and finally, acetylated by pyridine/acetanhydrid (3 h, 90° C.). The products were extracted by dichlormethan and washed with $NaHCO_3$. The products in the organic phase were analyzed by gas chromatography.
Analysis of the Acetylated Products The acetylated products were analyzed by gas chromatography which was performed with a chromatograph manufactured by the Carlo-Erba company model GC 6000 Vega equipped with an on-column injector, a 25 m CPSol8CB and a FID-detector. As a carrier gas hydrogen (80 kPa) was used.

The identification and integration of the peaks was performed as described by Sweet et al. (Carbohydr. Res. 40 (1975), 217).
Results The following main components were identified by gas chromatography:

| Sorbit acetylated in position | Interpretation |
| --- | --- |
| 1, 5 | Terminal Glucopyranose |
| 1, 3, 5 | 3-linked Glucopyranose |
| 1, 5, 6 | 6-linked Glucopyranose |
| 1, 3, 5, 6 | 3,6-linked Glucopyranose |

Furthermore, small amounts (rel. amount 0.2–0.4 mol %) of the following components were also found: 1, 4, 5- and 1, 3, 4, 5-sorbit and another tetraacetyl component (1,5,x,y). It is supposed that these components are due to incomplete methylation.

The following amounts were found for the above mentioned components in different experiments which were performed by changing the length of hydrolysis (indicated in bold by the number of hours) (MA=methylation analysis1; MA-b=methylation analysis 2):

| | Values in mol % | | | |
|---|---|---|---|---|
| Ac in Pos | MA (1 h) | MA (2 h) | MA (3 h) | MA-b (2 h) |
| 1,5 | 10,49 | 10,56 | 9,17 | 12,71 |
| 1,3,5 | 31,69 | 34,70 | 32,95 | 23,12 |
| 1,4,5 | 0,70 | 0,30 | 0,36 | 0,33 |
| 1,5,6 | 47,02 | 44,17 | 47,23 | 54,62 |
| 1,3,4,5 | 0,27 | 0,22 | 0,25 | 0,31 |
| 1,5,x,y | 0,19 | 0,32 | 0,36 | 0,24 |
| 1,3,5,6 | 9,64 | 9,73 | 9,68 | 8,67 |

Example 13

Construction of an Expression Cassette for Plants: Vacuolar and Plastidic Expression of an Alternansucrase By using plasmid Alsu-pET24a as a template and the PCR primers Al-5'-1.2 and Al-3'-2.2 (see SEQ ID NO 53 and 54) we amplified the coding region of alternansucrase from *Leuconostoc mesenteroides* which was then cut by the restriction enzymes SalI and PstI. Afterwards the resulting fragments were cloned into SalI and SdaI digested plasmids a) pBinAR-pat-Hyg and b) pBinAR-fnr-Hyg. The resulting plasmids were called a) pat-Alsu-Hyg (see FIG. 11) and b) fnr-Alsu-Hyg (see FIG. 12).

Note: The bacterial secretion signal peptide was removed from the cds by choice of the PCR primers.

PCR Conditions:

Buffer and polymerase from Boehringer Mannheim (Pwo Polymerase No. 1644947)

| | |
|---|---|
| DNA | 0,5 ng |
| 10x Buffer + MgSO$_4$ | 5 µl |
| dNTPs (je 10 mM) | 2 µl |
| Primer Sp-AS-5' | 100 nM |
| Primer Sp-AS-3' | 100 nM |
| Pwo Polymerase | 1,0 unit |
| distilled water | ad 50 µl |

| Reaction conditions: | | |
|---|---|---|
| Step 1 | 95° C. | 2:30 min |
| Step 2 | 95° C. | 0:30 min |
| Step 3 | 47° C. | 0:30 min |
| Step 4 | 68° C. | 7:00 min |
| | (plus 3 sec per cycle) | |
| Step 5 | 68° C. | 15:00 min |

The steps 2 to 4 were repeated 35 times in a cyclical manner.

Example 14

Northern Blot Analysis for Expression of Alternansucrase in Transgenic Plants

Leaves or tubers from potato plants transformed via agrobacteria with plasmids pat-Alsu-Hyg and fnr-Alsu-Hyg, respectively, were pulverized in a mill, type MM 200, (Retsch GmbH & Co. KG, 42781 Haan, Germany) at 30 Hz for 50 sec. RNA was extracted according to Logemann et al. (Anal. Biochem. 163 (1987), 16–20). 50 µg RNA per sample were loaded on 1 % agarose gels containing formaldehyde. After electrophoresis the RNA was transferred to nylon membranes (Hybond N, Amersham, UK) by the capillary transfer method (Sambrook et al., Molecular cloning: A laboratory manual, 2nd issue; Cold Spring Harbor Laboratory Press, NY, USA (1989)). Fixation of nucleic acids at the membrane was achieved by UV crosslinking (Stratalinker by Stratagene).

Membranes were prehybridized at 42° C. in hybridization buffer (25% (v/v) formamide, 250 mM sodium phosphate, pH 7.2, 250 mM sodiumchloride, 1 mM EDTA 7% (w/v) SDS, 25% (w/v) polyethyleneglycol 6000, 0,25 mg/ml sheared salmon sperm DNA) for 6 h. Afterwards hybridization was performed at 42° C. over night in hybridization buffer containing a radiolabelled probe in addition. The radioactive probe was prepared by using the Random Primed DNA Labelling Kit (Boehringer Mannheim, 1004760) and the approx. 4 kb Kpnl/Xhol-fragment from plasmid pAlsu-pSK according to the manufacturers manual. Membranes were washed at 50° C. once for 20 min in 3xSSC (Sambrook et al., Molecular cloning: A laboratory manual, 2nd issue; Cold Spring Harbor Laboratory Press, NY, USA (1989)) followed by washing once for 20 min in 0.5xSSC before exposing the membrane to an x-ray-film over night.

What is claimed is:

1. An isolated nucleic acid molecule selected from the group consisting of
   (a) nucleic acid molecules encoding at least the mature form of a protein comprising the amino acid sequence indicated in SEQ ID No. 2 or the amino acid sequence which is encoded by the DNA contained in plasmid DSM 12666;
   (b) nucleic acid molecules comprising the nucleotide sequence indicated in SEQ ID No. 1 or the nucleotide sequence of the DNA contained in plasmid DSM 12666 or a corresponding ribonucleotide sequence;
   (c) nucleic acid molecules encoding a protein, the amino acid sequence of which has a homology of at least 80% to the amino acid sequence indicated in SEQ ID No 2; and
   (d) nucleic acid molecules, the nucleotide sequence of which deviates on account of the degeneracy of the genetic code from the sequence of the nucleic acid molecules as defined in (a), (b) or (c),
wherein said nucleic acid molecule encodes an alternansucrase that catalyzes the conversion of sucrose to alternan.

2. A vector containing a nucleic acid molecule according to claim 1.

3. The vector according to claim 2, wherein the nucleic acid molecule is connected in sense orientation to regulatory elements ensuring the transcription and synthesis of a translatable RNA in prokaryotic or eukaryotic cells.

4. Plasmid pAlsu-pSK deposited under the accession No. DSM 12666.

5. A host cell transformed with a nucleic acid molecule of claim 1 or a vector of claim 2 or 3 or a cell descended from such a transformed host cell, wherein said descendant retains the introduced nucleic acid molecule or vector.

6. The host cell according to claim 5, which is a cell of a microorganism.

7. The host cell according to claim 5, which is an *E. coli* cell.

8. A method for preparing a protein that catalyzes the conversion of sucrose to alternan, wherein a host cell of claim 5 is cultured under conditions permitting the synthesis of the protein, and wherein the protein is isolated from the cultured cells and/or the culture medium.

9. A transgenic plant cell transformed with a nucleic acid molecule of claim 1 or a vector of claim 2 or 3, or a plant cell descended from such a cell, wherein said nucleic acid molecule encoding a protein that catalyzes the conversion of sucrose to alternan is under the control of regulatory elements permitting the transcription of a translatable mRNA in plant cells, wherein said descendant retains said nucleic acid molecule or vector.

10. A plant containing the plant cell of claim 9.

11. The plant according to claim 10, which is a plant that is cultivated for nutrition or a technical purpose.

12. The plant according to claim 10, which is a sugar-storing or starch-storing plant.

13. Propagation material of a plant according to claim 12, wherein said propagation material retains said nucleic acid molecule or vector.

14. A method for preparing alternan comprising the steps of extracting and isolating the alternan from a plant according to claim 12.

15. A method for preparing alternan and/or fructose, wherein (a) a host cell of claim 5 secretes an alternansucrase into a sucrose-containing culture medium; and (b) alternan and/or fructose is/are isolated from the culture medium.

16. The method according to claim 15, wherein the host cell is immobilized.

17. The plant according to claim 11, wherein said plant is selected from the group consisting of rye, maize, barley, oat, wheat, rice, pea, cassava, potato, rape, sunflower, soybean, flax, hemp, cotton, sugar cane, sugar beet, alfalfa, clover, ryegrass, tomato, lettuce, and chicory.

* * * * *

SEQUENCE LISTING

```
<160> NUMBER OF SEQ ID NOS: 54

<210> SEQ ID NO 1
<211> LENGTH: 9321
<212> TYPE: DNA
<213> ORGANISM: Leuconostoc mesenteroides
<220> FEATURE:
<221> NAME/KEY: CDS
<222> LOCATION: (678)..(6848)

<400> SEQUENCE: 1
gatcaaatag atgctaccgt tatacgagac gttaaggatt atcccaatct agtcgttttg      60
cgtaccttgt cgaaagctta tggtctggca aacctgagaa tcggctatgg cgtcatgcag     120
```

-continued

| | |
|---|---|
| gaaccactttt atcaggttat gcaggccgta cgtttaccat ataatttaaa tacctatcaa | 180 |
| atcacaggtg cagtagctgc ccttagtgat caactttatc tgcaatcagt tgttgctaag | 240 |
| gtgaagtctg aacgtgaaaa atttgaacaa tttttgacga acaccagtt taagtattat | 300 |
| caatcacaaa ccaactttct ctggattaaa gttggtgatg cgaaacgtgt tggtgaggct | 360 |
| cttctgtcag aagggtatca aattaatgac cgcctaaatg ccgaatggat tcgcattgca | 420 |
| ttaggaactg tgtctgataa tgaggggatg cagcgcattt tattgaattg ttaaaaaata | 480 |
| gctaagagag tatgttcttc tcttacctat ttttatttgt aattcctatt atttaatttt | 540 |
| gcatgacaat attaatagcg tgttacgatt ctactattta atgttaataa aattaataaa | 600 |
| tatggtatta tcttatatgg gtgatagatg caccaaatac tgtatcatgt ctggtcacat | 660 |

| gaaagggaga ataatta atg aaa caa caa gaa aca gtt acc cgt aaa aaa | 710 |
|---|---|
|                                 Met Lys Gln Gln Glu Thr Val Thr Arg Lys Lys | |
|                                  1               5                        10 | |
| ctt tat aaa tcc ggt aag gtt tgg gtt gca gca gct act gca ttt gcg | 758 |
| Leu Tyr Lys Ser Gly Lys Val Trp Val Ala Ala Ala Thr Ala Phe Ala | |
|              15                    20                    25 | |
| gta ttg ggg gtt tca act gta aca aca gtc cat gcg gat aca aat tcg | 806 |
| Val Leu Gly Val Ser Thr Val Thr Thr Val His Ala Asp Thr Asn Ser | |
|        30                    35                    40 | |
| aat gtc gct gtt aag caa ata aat aat aca gga acc aat gat tct ggc | 854 |
| Asn Val Ala Val Lys Gln Ile Asn Asn Thr Gly Thr Asn Asp Ser Gly | |
|  45                     50                    55 | |
| gaa aaa aag gta ccg gtt cca tca act aat aat gat agt ttg aag caa | 902 |
| Glu Lys Lys Val Pro Val Pro Ser Thr Asn Asn Asp Ser Leu Lys Gln | |
| 60               65                    70                    75 | |
| gga aca gat ggt ttt tgg tat gat tca gac ggc aat cgt gtc gat cag | 950 |
| Gly Thr Asp Gly Phe Trp Tyr Asp Ser Asp Gly Asn Arg Val Asp Gln | |
|                   80                    85                    90 | |
| aag acc aat cag att ctg ctt act gcg gaa caa ctt aaa aaa aat aac | 998 |
| Lys Thr Asn Gln Ile Leu Leu Thr Ala Glu Gln Leu Lys Lys Asn Asn | |
|              95                    100                 105 | |
| gaa aaa aat tta tca gta atc agt gat gat aca tca aaa aaa gat gat | 1046 |
| Glu Lys Asn Leu Ser Val Ile Ser Asp Asp Thr Ser Lys Lys Asp Asp | |
|        110                   115                 120 | |
| gaa aat att tct aag cag acc aaa att gct aat caa caa aca gta gat | 1094 |
| Glu Asn Ile Ser Lys Gln Thr Lys Ile Ala Asn Gln Gln Thr Val Asp | |
| 125                    130                 135 | |
| act gct aaa ggc ctg act acc agt aat tta tct gat ccc atc act ggg | 1142 |
| Thr Ala Lys Gly Leu Thr Thr Ser Asn Leu Ser Asp Pro Ile Thr Gly | |
| 140                    145                150                155 | |
| ggt cac tat gaa aat cac aat ggc tac ttt gtt tat ata gat gct tca | 1190 |
| Gly His Tyr Glu Asn His Asn Gly Tyr Phe Val Tyr Ile Asp Ala Ser | |
|                  160                   165                 170 | |
| gga aaa caa gta aca ggt ttg caa aat att gat ggt aat tta caa tat | 1238 |
| Gly Lys Gln Val Thr Gly Leu Gln Asn Ile Asp Gly Asn Leu Gln Tyr | |
|              175                  180                185 | |
| ttt gat gac aat gga tat caa gtc aag gga tcc ttc cga gat gtc aac | 1286 |
| Phe Asp Asp Asn Gly Tyr Gln Val Lys Gly Ser Phe Arg Asp Val Asn | |
|           190                    195                200 | |
| ggc aag cat atc tat ttt gat tca gta aca ggg aaa gct agt tca aat | 1334 |
| Gly Lys His Ile Tyr Phe Asp Ser Val Thr Gly Lys Ala Ser Ser Asn | |
|       205                   210                 215 | |
| gtt gat att gtt aac ggt aaa gct caa gga tat gat gcg caa ggc aac | 1382 |
| Val Asp Ile Val Asn Gly Lys Ala Gln Gly Tyr Asp Ala Gln Gly Asn | |
| 220                    225                230                235 | |

```
caa tta aag aaa agt tat gtc gcc gat agt tct ggg caa act tac tat         1430
Gln Leu Lys Lys Ser Tyr Val Ala Asp Ser Ser Gly Gln Thr Tyr Tyr
            240                 245                 250 ttt gat ggt aat ggc caa ccg tta atc ggc ttg caa aca att gat ggg         1478
Phe Asp Gly Asn Gly Gln Pro Leu Ile Gly Leu Gln Thr Ile Asp Gly
        255                 260                 265 aac cta caa tat ttt aac caa caa ggg gtt caa ata aag ggt ggt ttc         1526
Asn Leu Gln Tyr Phe Asn Gln Gln Gly Val Gln Ile Lys Gly Gly Phe
    270                 275                 280 caa gat gtt aac aat aaa cgt att tat ttt gca cca aac aca ggt aat         1574
Gln Asp Val Asn Asn Lys Arg Ile Tyr Phe Ala Pro Asn Thr Gly Asn
285                 290                 295 gcc gtt gcc aat act gaa ata att aac ggt aaa tta cag ggg cgt gac         1622
Ala Val Ala Asn Thr Glu Ile Ile Asn Gly Lys Leu Gln Gly Arg Asp
300                 305                 310                 315 gca aat ggt aac cag gta aag aat gca ttt agt aaa gat gtt gca gga         1670
Ala Asn Gly Asn Gln Val Lys Asn Ala Phe Ser Lys Asp Val Ala Gly
                320                 325                 330 aat aca ttt tat ttt gac gca aac ggt gtg atg tta aca ggg ttg caa         1718
Asn Thr Phe Tyr Phe Asp Ala Asn Gly Val Met Leu Thr Gly Leu Gln
            335                 340                 345 act att tca gga aag aca tat tat ctt gat gaa caa gga cac ctg aga         1766
Thr Ile Ser Gly Lys Thr Tyr Tyr Leu Asp Glu Gln Gly His Leu Arg
        350                 355                 360 aaa aat tac gcg gga aca ttc aat aat cag ttt atg tac ttc gat gct         1814
Lys Asn Tyr Ala Gly Thr Phe Asn Asn Gln Phe Met Tyr Phe Asp Ala
    365                 370                 375 gat aca ggt gcg ggt aaa aca gcg att gaa tat caa ttt gat caa gga         1862
Asp Thr Gly Ala Gly Lys Thr Ala Ile Glu Tyr Gln Phe Asp Gln Gly
380                 385                 390                 395 ttg gta tca caa agt aat gaa aat act cct cac aat gcc gca aag tct         1910
Leu Val Ser Gln Ser Asn Glu Asn Thr Pro His Asn Ala Ala Lys Ser
                400                 405                 410 tat gat aaa agt agt ttt gaa aat gtt gat ggt tac tta aca gca gat         1958
Tyr Asp Lys Ser Ser Phe Glu Asn Val Asp Gly Tyr Leu Thr Ala Asp
            415                 420                 425 aca tgg tat cgt cca acc gat att tta aaa aat gga gat act tgg acg         2006
Thr Trp Tyr Arg Pro Thr Asp Ile Leu Lys Asn Gly Asp Thr Trp Thr
        430                 435                 440 gca tct acc gaa act gat atg cgt ccg ctt tta atg aca tgg tgg cct         2054
Ala Ser Thr Glu Thr Asp Met Arg Pro Leu Leu Met Thr Trp Trp Pro
    445                 450                 455 gac aaa caa aca caa gca aat tac ttg aat ttt atg tct agt aaa gga         2102
Asp Lys Gln Thr Gln Ala Asn Tyr Leu Asn Phe Met Ser Ser Lys Gly
460                 465                 470                 475 ctt ggt ata acg acc act tat aca gca gct acg tca caa aaa aca cta         2150
Leu Gly Ile Thr Thr Thr Tyr Thr Ala Ala Thr Ser Gln Lys Thr Leu
                480                 485                 490 aat gac gca gcc ttt gtt att caa aca gca att gaa caa caa ata tct         2198
Asn Asp Ala Ala Phe Val Ile Gln Thr Ala Ile Glu Gln Gln Ile Ser
            495                 500                 505 ttg aaa aaa agt act gag tgg tta cgt gat gca att gat agt ttt gtg         2246
Leu Lys Lys Ser Thr Glu Trp Leu Arg Asp Ala Ile Asp Ser Phe Val
        510                 515                 520 aag acg caa gct aat tgg aat aag caa aca gaa gat gaa gct ttc gat         2294
Lys Thr Gln Ala Asn Trp Asn Lys Gln Thr Glu Asp Glu Ala Phe Asp
    525                 530                 535 ggt ttg cag tgg ctt caa ggg gga ttc cta gct tat caa gat gat tca         2342
Gly Leu Gln Trp Leu Gln Gly Gly Phe Leu Ala Tyr Gln Asp Asp Ser
540                 545                 550                 555
```

-continued

| | |
|---|---|
| cat cgg acg ccg aat act gat tca gga aat aac aga aaa cta gga cgt<br>His Arg Thr Pro Asn Thr Asp Ser Gly Asn Asn Arg Lys Leu Gly Arg<br>560 565 570 | 2390 |
| caa cca att aat atc gat ggt tcg aaa gat aca act gat ggt aaa ggc<br>Gln Pro Ile Asn Ile Asp Gly Ser Lys Asp Thr Thr Asp Gly Lys Gly<br>575 580 585 | 2438 |
| tct gaa ttc tta tta gct aac gat att gac aac tca aat ccg att gtt<br>Ser Glu Phe Leu Leu Ala Asn Asp Ile Asp Asn Ser Asn Pro Ile Val<br>590 595 600 | 2486 |
| caa gct gag caa tta aac tgg cta cac tat tta atg aat ttt ggt agt<br>Gln Ala Glu Gln Leu Asn Trp Leu His Tyr Leu Met Asn Phe Gly Ser<br>605 610 615 | 2534 |
| att aca ggt aat aat gac aat gcg aat ttt gat ggc att cgt gta gat<br>Ile Thr Gly Asn Asn Asp Asn Ala Asn Phe Asp Gly Ile Arg Val Asp<br>620 625 630 635 | 2582 |
| gct gtt gat aat gtt gat gct gat tta cta aaa ata gct ggc gat tat<br>Ala Val Asp Asn Val Asp Ala Asp Leu Leu Lys Ile Ala Gly Asp Tyr<br>640 645 650 | 2630 |
| ttt aaa gct cta tat ggt aca gat aaa agc gac gcc aat gcc aat aag<br>Phe Lys Ala Leu Tyr Gly Thr Asp Lys Ser Asp Ala Asn Ala Asn Lys<br>655 660 665 | 2678 |
| cat ttg tct att tta gaa gac tgg aac ggt aaa gat cct cag tat gtt<br>His Leu Ser Ile Leu Glu Asp Trp Asn Gly Lys Asp Pro Gln Tyr Val<br>670 675 680 | 2726 |
| aat caa cag ggc aat gcg caa tta aca atg gat tac aca gtt act tca<br>Asn Gln Gln Gly Asn Ala Gln Leu Thr Met Asp Tyr Thr Val Thr Ser<br>685 690 695 | 2774 |
| cag ttt ggc aat tct cta aca cat ggc gcc aac aac agg agt aac atg<br>Gln Phe Gly Asn Ser Leu Thr His Gly Ala Asn Asn Arg Ser Asn Met<br>700 705 710 715 | 2822 |
| tgg tat ttc tta gat act ggc tat tat ctt aat gga gat ctt aat aag<br>Trp Tyr Phe Leu Asp Thr Gly Tyr Tyr Leu Asn Gly Asp Leu Asn Lys<br>720 725 730 | 2870 |
| aag ata gta gat aag aac cgt cca aat tct ggc act ttg gtt aac aga<br>Lys Ile Val Asp Lys Asn Arg Pro Asn Ser Gly Thr Leu Val Asn Arg<br>735 740 745 | 2918 |
| att gct aat tca ggt gat aca aaa gtt att cca aat tat agt ttt gtt<br>Ile Ala Asn Ser Gly Asp Thr Lys Val Ile Pro Asn Tyr Ser Phe Val<br>750 755 760 | 2966 |
| aga gca cat gat tac gat gct caa gat cca att aga aaa gcc atg att<br>Arg Ala His Asp Tyr Asp Ala Gln Asp Pro Ile Arg Lys Ala Met Ile<br>765 770 775 | 3014 |
| gat cat ggt att att aaa aac atg cag gat act ttc act ttt gac caa<br>Asp His Gly Ile Ile Lys Asn Met Gln Asp Thr Phe Thr Phe Asp Gln<br>780 785 790 795 | 3062 |
| ctg gct cag gga atg gaa ttc tac tat aaa gat caa gag aat ccg tct<br>Leu Ala Gln Gly Met Glu Phe Tyr Tyr Lys Asp Gln Glu Asn Pro Ser<br>800 805 810 | 3110 |
| ggt ttc aaa aag tat aac gat tat aac tta cct agt gct tat gca atg<br>Gly Phe Lys Lys Tyr Asn Asp Tyr Asn Leu Pro Ser Ala Tyr Ala Met<br>815 820 825 | 3158 |
| ttg ttg act aat aag gat act gta cct cgt gtc tat tat gga gat atg<br>Leu Leu Thr Asn Lys Asp Thr Val Pro Arg Val Tyr Tyr Gly Asp Met<br>830 835 840 | 3206 |
| tac ctc gaa ggc ggg caa tat atg gaa aaa ggg acg att tac aat cct<br>Tyr Leu Glu Gly Gly Gln Tyr Met Glu Lys Gly Thr Ile Tyr Asn Pro<br>845 850 855 | 3254 |
| gtc att tca gcg ttg ctc aaa gct aga ata aaa tat gtt tct ggt ggg<br>Val Ile Ser Ala Leu Leu Lys Ala Arg Ile Lys Tyr Val Ser Gly Gly<br>860 865 870 875 | 3302 |

-continued

| | |
|---|---|
| caa aca atg gct acc gat agt tct gga aaa gac ctt aaa gat ggc gaa<br>Gln Thr Met Ala Thr Asp Ser Ser Gly Lys Asp Leu Lys Asp Gly Glu<br>                    880                 885                 890 | 3350 |
| act gat ttg tta aca agt gtt cga ttt ggt aaa gga att atg aca tca<br>Thr Asp Leu Leu Thr Ser Val Arg Phe Gly Lys Gly Ile Met Thr Ser<br>            895                 900                 905 | 3398 |
| gat caa acc aca aca caa gac aat agc caa gat tat aaa aat caa ggc<br>Asp Gln Thr Thr Thr Gln Asp Asn Ser Gln Asp Tyr Lys Asn Gln Gly<br>910                 915                 920 | 3446 |
| atc ggt gtc att gtt ggt aat aac cct gac ctt aag ttg aac aat gat<br>Ile Gly Val Ile Val Gly Asn Asn Pro Asp Leu Lys Leu Asn Asn Asp<br>    925                 930                 935 | 3494 |
| aag acc att acc ttg cat atg gga aag gcg cat aag aat caa ctt tac<br>Lys Thr Ile Thr Leu His Met Gly Lys Ala His Lys Asn Gln Leu Tyr<br>940                 945                 950                 955 | 3542 |
| cgt gcc tta gta tta tca aat gac tca gga att gat gtt tat gat agt<br>Arg Ala Leu Val Leu Ser Asn Asp Ser Gly Ile Asp Val Tyr Asp Ser<br>                    960                 965                 970 | 3590 |
| gat gat aaa gca cca act ttg aga aca aat gac aac ggt gac ttg att<br>Asp Asp Lys Ala Pro Thr Leu Arg Thr Asn Asp Asn Gly Asp Leu Ile<br>            975                 980                 985 | 3638 |
| ttc cat aag aca aat acg ttt gtg aag caa gat gga act att ata aat<br>Phe His Lys Thr Asn Thr Phe Val Lys Gln Asp Gly Thr Ile Ile Asn<br>990                 995                 1000 | 3686 |
| tac gaa atg aag gga tca tta aat gct tta att tca ggt tat tta ggt<br>Tyr Glu Met Lys Gly Ser Leu Asn Ala Leu Ile Ser Gly Tyr Leu Gly<br>    1005                 1010                 1015 | 3734 |
| gtc tgg gtg cca gtt gga gct agt gat tca caa gat gct cgt aca gtg<br>Val Trp Val Pro Val Gly Ala Ser Asp Ser Gln Asp Ala Arg Thr Val<br>1020                 1025                 1030                 1035 | 3782 |
| gca act gag tca tca tca agt aat gat ggt tct gta ttc cat tca aat<br>Ala Thr Glu Ser Ser Ser Ser Asn Asp Gly Ser Val Phe His Ser Asn<br>                    1040                 1045                 1050 | 3830 |
| gct gca tta gat tct aat gtt ata tat gaa ggc ttt tca aac ttt caa<br>Ala Ala Leu Asp Ser Asn Val Ile Tyr Glu Gly Phe Ser Asn Phe Gln<br>            1055                 1060                 1065 | 3878 |
| gcg atg ccg act tct cct gag caa agt aca aat gtt gtt att gca aca<br>Ala Met Pro Thr Ser Pro Glu Gln Ser Thr Asn Val Val Ile Ala Thr<br>1070                 1075                 1080 | 3926 |
| aag gct aac tta ttt aaa gaa tta ggt att act agt ttt gag tta gca<br>Lys Ala Asn Leu Phe Lys Glu Leu Gly Ile Thr Ser Phe Glu Leu Ala<br>    1085                 1090                 1095 | 3974 |
| cct caa tat agg tct agt ggt gac act aat tac ggt ggc atg tca ttc<br>Pro Gln Tyr Arg Ser Ser Gly Asp Thr Asn Tyr Gly Gly Met Ser Phe<br>1100                 1105                 1110                 1115 | 4022 |
| tta gat tct ttc tta aat aat ggt tat gca ttt acc gat aga tat gat<br>Leu Asp Ser Phe Leu Asn Asn Gly Tyr Ala Phe Thr Asp Arg Tyr Asp<br>                    1120                 1125                 1130 | 4070 |
| tta ggc ttt aac aaa gca gac ggg aat cct aac cca aca aag tat gga<br>Leu Gly Phe Asn Lys Ala Asp Gly Asn Pro Asn Pro Thr Lys Tyr Gly<br>            1135                 1140                 1145 | 4118 |
| aca gat caa gat tta cgt aat gca ata gag gca tta cac aaa aac ggc<br>Thr Asp Gln Asp Leu Arg Asn Ala Ile Glu Ala Leu His Lys Asn Gly<br>1150                 1155                 1160 | 4166 |
| atg cag gct ata gct gat tgg gtt cct gac caa ata tat gct tta cca<br>Met Gln Ala Ile Ala Asp Trp Val Pro Asp Gln Ile Tyr Ala Leu Pro<br>    1165                 1170                 1175 | 4214 |
| gga aag gaa gtt gtt acc gct act aga gta gac gaa cgg gga aat caa<br>Gly Lys Glu Val Val Thr Ala Thr Arg Val Asp Glu Arg Gly Asn Gln<br>1180                 1185                 1190                 1195 | 4262 |

-continued

```
cta aaa gac aca gat ttt gtc aac tta ctc tat gtt gct aat act aaa    4310
Leu Lys Asp Thr Asp Phe Val Asn Leu Leu Tyr Val Ala Asn Thr Lys
        1200            1205                1210 agt agt ggt gtg gat tat cag gca aag tat ggc ggc gaa ttt tta gat    4358
Ser Ser Gly Val Asp Tyr Gln Ala Lys Tyr Gly Gly Glu Phe Leu Asp
            1215            1220                1225 aaa tta aga gaa gag tac cca tcg tta ttc aaa cag aac caa gta tcg    4406
Lys Leu Arg Glu Glu Tyr Pro Ser Leu Phe Lys Gln Asn Gln Val Ser
        1230            1235                1240 aca ggt cag cca att gat gct tct aca aaa att aag caa tgg tca gct    4454
Thr Gly Gln Pro Ile Asp Ala Ser Thr Lys Ile Lys Gln Trp Ser Ala
    1245            1250                1255 aaa tat atg aat ggg acc aat att tta cat cga ggt gct tat tat gtt    4502
Lys Tyr Met Asn Gly Thr Asn Ile Leu His Arg Gly Ala Tyr Tyr Val
1260            1265                1270                1275 ttg aaa gac tgg gct act aac cag tat ttt aac att gca aaa acg aat    4550
Leu Lys Asp Trp Ala Thr Asn Gln Tyr Phe Asn Ile Ala Lys Thr Asn
            1280            1285                1290 gaa gta ttt ttg cca cta cag ttg cag aat aaa gat gcg caa act ggt    4598
Glu Val Phe Leu Pro Leu Gln Leu Gln Asn Lys Asp Ala Gln Thr Gly
        1295            1300                1305 ttc att agt gat gcc tcc ggt gta aaa tat tac tca att agt ggt tat    4646
Phe Ile Ser Asp Ala Ser Gly Val Lys Tyr Tyr Ser Ile Ser Gly Tyr
    1310            1315                1320 caa gca aaa gat act ttt att gaa gat ggt aat ggg aat tgg tat tac    4694
Gln Ala Lys Asp Thr Phe Ile Glu Asp Gly Asn Gly Asn Trp Tyr Tyr
1325            1330                1335 ttt gat aaa gat ggt tac atg gtg cgt tcg cag caa gga gaa aat cct    4742
Phe Asp Lys Asp Gly Tyr Met Val Arg Ser Gln Gln Gly Glu Asn Pro
1340            1345                1350                1355 ata aga aca gtc gaa act agt gtc aac aca cga aac ggt aat tat tac    4790
Ile Arg Thr Val Glu Thr Ser Val Asn Thr Arg Asn Gly Asn Tyr Tyr
        1360            1365                1370 ttt atg cca aat ggt gtc gag ttg cgc aaa ggc ttt gga acg gat aat    4838
Phe Met Pro Asn Gly Val Glu Leu Arg Lys Gly Phe Gly Thr Asp Asn
    1375            1380                1385 agt ggt aat gtc tat tat ttt gat gat caa ggt aag atg gtg aga gat    4886
Ser Gly Asn Val Tyr Tyr Phe Asp Asp Gln Gly Lys Met Val Arg Asp
        1390            1395                1400 aaa tac att aac gat gat gct aat aat ttt tat cac tta aat gtt gat    4934
Lys Tyr Ile Asn Asp Asp Ala Asn Asn Phe Tyr His Leu Asn Val Asp
    1405            1410                1415 ggg act atg tct cga gga cta ttt aaa ttt gat tct gat act cta cag    4982
Gly Thr Met Ser Arg Gly Leu Phe Lys Phe Asp Ser Asp Thr Leu Gln
1420            1425            1430                1435 tat ttt gct agt aat ggt gtc caa ata aaa gat agt tat gcg aag gat    5030
Tyr Phe Ala Ser Asn Gly Val Gln Ile Lys Asp Ser Tyr Ala Lys Asp
        1440            1445                1450 agt aaa ggc aat aaa tat tat ttt gac tca gct aca gga aat aac gat    5078
Ser Lys Gly Asn Lys Tyr Tyr Phe Asp Ser Ala Thr Gly Asn Asn Asp
    1455            1460                1465 act ggg aaa gcc caa act tgg gat ggt aat ggc tac tat att act att    5126
Thr Gly Lys Ala Gln Thr Trp Asp Gly Asn Gly Tyr Tyr Ile Thr Ile
        1470            1475                1480 gat tct gat gcg aac aat aca att ggg gtt aac aca gac tac act gcc    5174
Asp Ser Asp Ala Asn Asn Thr Ile Gly Val Asn Thr Asp Tyr Thr Ala
1485            1490                1495 tac atc act agc tcg ctg cgc gaa gat ggc tta ttt gct aac gca cct    5222
Tyr Ile Thr Ser Ser Leu Arg Glu Asp Gly Leu Phe Ala Asn Ala Pro
1500            1505                1510                1515
```

-continued

| | |
|---|---|
| tac ggt gtt gta aca aaa gac caa aat ggt aac gat ctt aag tgg cag<br>Tyr Gly Val Val Thr Lys Asp Gln Asn Gly Asn Asp Leu Lys Trp Gln<br>        1520                    1525                    1530 | 5270 |
| tat att aac cat acg aaa cag tac gaa ggg caa caa gtg caa gtc acg<br>Tyr Ile Asn His Thr Lys Gln Tyr Glu Gly Gln Gln Val Gln Val Thr<br>    1535                  1540                  1545 | 5318 |
| cgt caa tac aca gac agt aag gga gtc agc tgg aac tta att acc ttt<br>Arg Gln Tyr Thr Asp Ser Lys Gly Val Ser Trp Asn Leu Ile Thr Phe<br>1550                  1555                  1560 | 5366 |
| gct ggt ggt gat tta caa gga caa agg ctt tgg gtg gat agt cgt gcg<br>Ala Gly Gly Asp Leu Gln Gly Gln Arg Leu Trp Val Asp Ser Arg Ala<br>        1565                  1570                  1575 | 5414 |
| tta act atg aca cca ttt aaa acg atg aac caa ata agc ttc att agt<br>Leu Thr Met Thr Pro Phe Lys Thr Met Asn Gln Ile Ser Phe Ile Ser<br>1580                  1585                  1590                  1595 | 5462 |
| tat gct aac cgc aat gat ggg ttg ttt ttg aat gcg cca tac caa gtc<br>Tyr Ala Asn Arg Asn Asp Gly Leu Phe Leu Asn Ala Pro Tyr Gln Val<br>        1600                  1605                  1610 | 5510 |
| aag ggg tat caa tta gct ggg atg tcc aac caa tac aag ggc caa caa<br>Lys Gly Tyr Gln Leu Ala Gly Met Ser Asn Gln Tyr Lys Gly Gln Gln<br>            1615                  1620                  1625 | 5558 |
| gtg acc att gct ggg gtg gcg aac gtt tct gga aaa gac tgg agt ctg<br>Val Thr Ile Ala Gly Val Ala Asn Val Ser Gly Lys Asp Trp Ser Leu<br>    1630                  1635                  1640 | 5606 |
| att agt ttt aat ggg aca cag tac tgg att gat agt cag gca ttg aat<br>Ile Ser Phe Asn Gly Thr Gln Tyr Trp Ile Asp Ser Gln Ala Leu Asn<br>        1645                  1650                  1655 | 5654 |
| acc aat ttc aca cat gac atg aac caa aag gtc ttt gtc aat aca act<br>Thr Asn Phe Thr His Asp Met Asn Gln Lys Val Phe Val Asn Thr Thr<br>1660                  1665                  1670                  1675 | 5702 |
| agt aat ctt gat ggg tta ttc tta aat gcg cca tac cgt caa ccg ggt<br>Ser Asn Leu Asp Gly Leu Phe Leu Asn Ala Pro Tyr Arg Gln Pro Gly<br>        1680                  1685                  1690 | 5750 |
| tat aag tta gcc ggt ttg gct aaa aat tac aac aac caa acg gtt act<br>Tyr Lys Leu Ala Gly Leu Ala Lys Asn Tyr Asn Asn Gln Thr Val Thr<br>            1695                  1700                  1705 | 5798 |
| gtt agt caa cag tac ttt gat gat caa ggc acg gtc tgg agt cag gtt<br>Val Ser Gln Gln Tyr Phe Asp Asp Gln Gly Thr Val Trp Ser Gln Val<br>    1710                  1715                  1720 | 5846 |
| gtc ctt ggg ggt cag acg gtc tgg gtt gat aac cat gca ttg gca cag<br>Val Leu Gly Gly Gln Thr Val Trp Val Asp Asn His Ala Leu Ala Gln<br>        1725                  1730                  1735 | 5894 |
| atg caa gtt agt gat aca gac caa cag ctc tat gtg aat agc aat ggt<br>Met Gln Val Ser Asp Thr Asp Gln Gln Leu Tyr Val Asn Ser Asn Gly<br>1740                  1745                  1750                  1755 | 5942 |
| cgg aat gat ggg tta ttc ttg aat gcg cca tat cgt ggt caa ggg tca<br>Arg Asn Asp Gly Leu Phe Leu Asn Ala Pro Tyr Arg Gly Gln Gly Ser<br>            1760                  1765                  1770 | 5990 |
| caa ctg ata ggc atg acg gca gat tat aat ggg caa cat gta caa gtg<br>Gln Leu Ile Gly Met Thr Ala Asp Tyr Asn Gly Gln His Val Gln Val<br>    1775                  1780                  1785 | 6038 |
| acc aag caa ggg caa gat gcc tat ggt gca caa tgg cgt ctt att acg<br>Thr Lys Gln Gly Gln Asp Ala Tyr Gly Ala Gln Trp Arg Leu Ile Thr<br>        1790                  1795                  1800 | 6086 |
| cta aat aat caa cag gtc tgg gtt gat agt cgc gct ttg agc aca aca<br>Leu Asn Asn Gln Gln Val Trp Val Asp Ser Arg Ala Leu Ser Thr Thr<br>            1805                  1810                  1815 | 6134 |
| atc atg caa gcc atg aat gat aat atg tat gta aat agc agc caa cgg<br>Ile Met Gln Ala Met Asn Asp Asn Met Tyr Val Asn Ser Ser Gln Arg<br>1820                  1825                  1830                  1835 | 6182 |

```
                                 -continued aca gat ggc ttg tgg tta aac gca cct tat acg atg agt ggg gct aaa       6230
Thr Asp Gly Leu Trp Leu Asn Ala Pro Tyr Thr Met Ser Gly Ala Lys
        1840                1845                1850 tgg gct ggt gat aca cgt tca gct aat ggg cgc tat gtc cat att tca       6278
Trp Ala Gly Asp Thr Arg Ser Ala Asn Gly Arg Tyr Val His Ile Ser
    1855                1860                1865 aaa gct tat tca aac gaa gtc ggc aat aca tat tac ttg acg aat ttg       6326
Lys Ala Tyr Ser Asn Glu Val Gly Asn Thr Tyr Tyr Leu Thr Asn Leu
1870                1875                1880 aat ggt caa agc aca tgg att gac aag cgg gcg ttt act gtg acc ttc       6374
Asn Gly Gln Ser Thr Trp Ile Asp Lys Arg Ala Phe Thr Val Thr Phe
    1885                1890                1895 gat cag gtg gtg gca tta aat gca acg att gtg gca cgc caa cga cca       6422
Asp Gln Val Val Ala Leu Asn Ala Thr Ile Val Ala Arg Gln Arg Pro
1900                1905                1910                1915 gat ggg atg ttt aag aca gca cca tat ggt gaa gcg ggg gcg cag ttt       6470
Asp Gly Met Phe Lys Thr Ala Pro Tyr Gly Glu Ala Gly Ala Gln Phe
        1920                1925                1930 gtc gat tat gtg aca aac tat aac cag caa acc gtg cca gta aca aag       6518
Val Asp Tyr Val Thr Asn Tyr Asn Gln Gln Thr Val Pro Val Thr Lys
    1935                1940                1945 caa cat tca gat gct cag ggg aat caa tgg tac tta gcg aca gtg aat       6566
Gln His Ser Asp Ala Gln Gly Asn Gln Trp Tyr Leu Ala Thr Val Asn
1950                1955                1960 ggg aca caa tac tgg att gat caa cgg tca ttt tca cca gta gta acg       6614
Gly Thr Gln Tyr Trp Ile Asp Gln Arg Ser Phe Ser Pro Val Val Thr
    1965                1970                1975 aag gtg gtt gat tat caa gct aag att gtg cca cgg aca aca cgt gat       6662
Lys Val Val Asp Tyr Gln Ala Lys Ile Val Pro Arg Thr Thr Arg Asp
1980                1985                1990                1995 ggt gtg ttt agt ggc gca ccc tat ggg gaa gtg aat gct aag cta gtt       6710
Gly Val Phe Ser Gly Ala Pro Tyr Gly Glu Val Asn Ala Lys Leu Val
        2000                2005                2010 aac atg gca act gcg tat caa aat caa gtt gtc cat gcg aca ggg gaa       6758
Asn Met Ala Thr Ala Tyr Gln Asn Gln Val Val His Ala Thr Gly Glu
    2015                2020                2025 tat acg aat gct tca ggg atc aca tgg agt cag ttc gcg tta agc ggg       6806
Tyr Thr Asn Ala Ser Gly Ile Thr Trp Ser Gln Phe Ala Leu Ser Gly
2030                2035                2040 caa gaa gac aag cta tgg att gat aag cgt gct ttg caa gct                6848
Gln Glu Asp Lys Leu Trp Ile Asp Lys Arg Ala Leu Gln Ala
    2045                2050                2055 taagggaagg attcgacaaa ggagggtaac attatcagcg gatggtgtta tcctcctttc      6908
ctgtactcag tatttcccaa ataattgaga cagtttcatg acaaatcaac aaaactagtg      6968
tcaatgcctc ggttatgggg taaactacta ttagttaaag ggttgttgca taataatatc      7028
acattcaata tattatgtat ttttatctga ttatgtgatt ttttgagatt tggagcgaaa      7088
atgaataaag taataattaa taaaagtttc tgtgttttgg taatgagttt gttgtcgata      7148
tttctattct cattaagagt agacgctcgt tccaatagtg gctacaatca atatctttt       7208 aatcaacatg aaattgctta tgcgcctttt agtcaagtac cttggtatgc aactgtgaat      7268
gtcggaatgt ctgcagacaa aaataatatc tatacagcta ttgatatggg gccatagtat      7328
caaggaactt ctttttttcc gtggtggtat caacatgata attatgatta tcatgatggt      7388
tatcaacttg cgattgacaa tcaatcgctt tcatagaaa tggttgatac aggaaggtcg       7448
tcgtttgatg ttattgagtt gtatacaggt aaaaagttg gttatggaaa attcacagcc       7508
tataactata acaagacttc atggcagttt caaatatctt taaaggcgat aaagaaaatt      7568
```

-continued

```
ttaaataata acatatcaga aaatgcgaca attagtttgt acaatggtta tctattcaaa    7628
caagccgaaa gtatcacgta tgctggttca ccaacagggc catggttact tgccggtatt    7688
ggtttggttt ttgctggtgg gggctattac ctgcaaaatc agcgccgaaa acgattacg     7748 gcatcatcaa caaacgaggt aacccatgct aataatgct gttattattg gtctaattat     7808
tatttgggtc tatgtattat ctgttctgaa gcgtgctaaa acggatgcgt tttattttt     7868 ggctggcagc gcaggcttgt tcgtcattct tcttttatgg agtaaacctt atggtgtttg    7928
gttgttttcg accattctca cttggtcggc cggggttgtt ggtcatctca ctggcttatt    7988
tgatactttc tatgcgtcac atgttattca ggttgtggcg aatcatcata ccagcatttt    8048
attggttgat tatgaatgtt caggcattat tgaaacaacg gcattttggg gattaattgc    8108
cttttatcct gtgtatgatg cacaaaagcg gttaatgttg gcgcttattg gggcattatg    8168 gttttttcctt gcaaatacgt tacgactatc ttttgttgca gttgtaattt attattttgg    8228
cgatggcgct tttatgttg ctcattcaat tatcggacgc ctgttgttct attcaattgt     8288
aatcttgctt tattatctag tcttcataaa ggggcaactt gttaatcaaa tgctcaaaaa    8348
acagggataa actatgtcat tttatttaca tcaatttact tatcagttag gttttggtt     8408 cacttggttg ctcattccgt tgttgtgga aattttccca gctattattt caatctagtt      8468
ttgataaaaa catcaaaaaa gcatcaagtg atgcaagaac cattgaaatt accaatggta    8528
tctattgtat tacctatata taattcagga caaacattat accagtgtat tcagtcgatt    8588
agtcaatcaa cctatccaaa acaattaatc caaattattg ccgtgaataa tcaaagcact    8648
gataacagtt ttacagtgtt taatcaggct caagctgatt tcccaatact tagaatgcag    8708
tggatgaaca cagatcaagg taaagcgcgt gcactaaatg ctgctatta taatagtatg     8768 gggcaatata ttattaattt ggatactgat ggttggttag aacccaatgc cttaaaacgg     8828
tttgtgcttt attttgaaaa tcactcagaa attgatgtag caactggtac gattctgaca    8888
caaaaaaaaa tgattcaaaa aacgcaaagt aaatggctta aattgctaca gttaaacgaa    8948
tattttgagt atgcacaatc attcttatca ggccgtagta ttgaaaaccg tggtaatcgt    9008
ttgttcacaa tgtcaggtgc attttcagcg tttagacgtg atgtattagt tcagacattt    9068
atgtataatg ttgacacggt tggtgaagat actgatatga catttcaact gcgattccgc    9128
ctaggcaagc gtattggttt ctgtgatgat gccatgtttt atgttgaacc aatatcaggt    9188
tatagtgaac tttatttaca acggcagcgt tggcagcgtg gcaaattga agtcgcacaa     9248 aatttcatgc agaataagtt gagtgtccgt cagattttta ctaactttat gattagtcga    9308
ttaatgattg atc                                                         9321
```

<210> SEQ ID NO 2
<211> LENGTH: 2057
<212> TYPE: PRT
<213> ORGANISM: Leuconostoc mesenteroides

<400> SEQUENCE: 2

Met Lys Gln Gln Glu Thr Val Thr Arg Lys Lys Leu Tyr Lys Ser Gly
 1               5                  10                  15

Lys Val Trp Val Ala Ala Ala Thr Ala Phe Ala Val Leu Gly Val Ser
                20                  25                  30

Thr Val Thr Thr Val His Ala Asp Thr Asn Ser Asn Val Ala Val Lys
            35                  40                  45

Gln Ile Asn Asn Thr Gly Thr Asn Asp Ser Gly Glu Lys Lys Val Pro
        50                  55                  60

-continued

```
Val Pro Ser Thr Asn Asn Asp Ser Leu Lys Gln Gly Thr Asp Gly Phe
 65                  70                  75                  80

Trp Tyr Asp Ser Asp Gly Asn Arg Val Asp Gln Lys Thr Asn Gln Ile
             85                  90                  95

Leu Leu Thr Ala Glu Gln Leu Lys Lys Asn Glu Lys Asn Leu Ser
        100                 105                 110

Val Ile Ser Asp Asp Thr Ser Lys Lys Asp Asp Glu Asn Ile Ser Lys
            115                 120                 125

Gln Thr Lys Ile Ala Asn Gln Gln Thr Val Asp Thr Ala Lys Gly Leu
    130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asp Asn Gly
            180                 185                 190

Tyr Gln Val Lys Gly Ser Phe Arg Asp Val Asn Gly Lys His Ile Tyr
        195                 200                 205

Phe Asp Ser Val Thr Gly Lys Ala Ser Ser Asn Val Asp Ile Val Asn
    210                 215                 220

Gly Lys Ala Gln Gly Tyr Asp Ala Gln Gly Asn Gln Leu Lys Lys Ser
225                 230                 235                 240

Tyr Val Ala Asp Ser Ser Gly Gln Thr Tyr Tyr Phe Asp Gly Asn Gly
                245                 250                 255

Gln Pro Leu Ile Gly Leu Gln Thr Ile Asp Gly Asn Leu Gln Tyr Phe
            260                 265                 270

Asn Gln Gln Gly Val Gln Ile Lys Gly Gly Phe Gln Asp Val Asn Asn
        275                 280                 285

Lys Arg Ile Tyr Phe Ala Pro Asn Thr Gly Asn Ala Val Ala Asn Thr
    290                 295                 300

Glu Ile Ile Asn Gly Lys Leu Gln Gly Arg Asp Ala Asn Gly Asn Gln
305                 310                 315                 320

Val Lys Asn Ala Phe Ser Lys Asp Val Ala Gly Asn Thr Phe Tyr Phe
                325                 330                 335

Asp Ala Asn Gly Val Met Leu Thr Gly Leu Gln Thr Ile Ser Gly Lys
            340                 345                 350

Thr Tyr Tyr Leu Asp Glu Gln Gly His Leu Arg Lys Asn Tyr Ala Gly
        355                 360                 365

Thr Phe Asn Asn Gln Phe Met Tyr Phe Asp Ala Asp Thr Gly Ala Gly
    370                 375                 380

Lys Thr Ala Ile Glu Tyr Gln Phe Asp Gln Gly Leu Val Ser Gln Ser
385                 390                 395                 400

Asn Glu Asn Thr Pro His Asn Ala Ala Lys Ser Tyr Asp Lys Ser Ser
                405                 410                 415

Phe Glu Asn Val Asp Gly Tyr Leu Thr Ala Asp Thr Trp Tyr Arg Pro
            420                 425                 430

Thr Asp Ile Leu Lys Asn Gly Asp Thr Trp Thr Ala Ser Thr Glu Thr
        435                 440                 445

Asp Met Arg Pro Leu Leu Met Thr Trp Trp Pro Asp Lys Gln Thr Gln
    450                 455                 460

Ala Asn Tyr Leu Asn Phe Met Ser Ser Lys Gly Leu Gly Ile Thr Thr
465                 470                 475                 480
```

```
Thr Tyr Thr Ala Ala Thr Ser Gln Lys Thr Leu Asn Asp Ala Ala Phe
                485                 490                 495

Val Ile Gln Thr Ala Ile Glu Gln Gln Ile Ser Leu Lys Lys Ser Thr
                500                 505                 510

Glu Trp Leu Arg Asp Ala Ile Asp Ser Phe Val Lys Thr Gln Ala Asn
                515                 520                 525

Trp Asn Lys Gln Thr Glu Asp Glu Ala Phe Asp Gly Leu Gln Trp Leu
            530                 535                 540

Gln Gly Gly Phe Leu Ala Tyr Gln Asp Asp Ser His Arg Thr Pro Asn
545                 550                 555                 560

Thr Asp Ser Gly Asn Asn Arg Lys Leu Gly Arg Gln Pro Ile Asn Ile
                565                 570                 575

Asp Gly Ser Lys Asp Thr Thr Asp Gly Lys Ser Glu Phe Leu Leu
                580                 585                 590

Ala Asn Asp Ile Asp Asn Ser Asn Pro Ile Val Gln Ala Glu Gln Leu
                595                 600                 605

Asn Trp Leu His Tyr Leu Met Asn Phe Gly Ser Ile Thr Gly Asn Asn
                610                 615                 620

Asp Asn Ala Asn Phe Asp Gly Ile Arg Val Asp Ala Val Asp Asn Val
625                 630                 635                 640

Asp Ala Asp Leu Leu Lys Ile Ala Gly Asp Tyr Phe Lys Ala Leu Tyr
                645                 650                 655

Gly Thr Asp Lys Ser Asp Ala Asn Ala Asn Lys His Leu Ser Ile Leu
                660                 665                 670

Glu Asp Trp Asn Gly Lys Asp Pro Gln Tyr Val Asn Gln Gln Gly Asn
                675                 680                 685

Ala Gln Leu Thr Met Asp Tyr Thr Val Thr Ser Gln Phe Gly Asn Ser
                690                 695                 700

Leu Thr His Gly Ala Asn Asn Arg Ser Asn Met Trp Tyr Phe Leu Asp
705                 710                 715                 720

Thr Gly Tyr Tyr Leu Asn Gly Asp Leu Asn Lys Lys Ile Val Asp Lys
                725                 730                 735

Asn Arg Pro Asn Ser Gly Thr Leu Val Asn Arg Ile Ala Asn Ser Gly
                740                 745                 750

Asp Thr Lys Val Ile Pro Asn Tyr Ser Phe Val Arg Ala His Asp Tyr
                755                 760                 765

Asp Ala Gln Asp Pro Ile Arg Lys Ala Met Ile Asp His Gly Ile Ile
770                 775                 780

Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
                805                 810                 815

Asn Asp Tyr Asn Leu Pro Ser Ala Tyr Ala Met Leu Leu Thr Asn Lys
                820                 825                 830

Asp Thr Val Pro Arg Val Tyr Tyr Gly Asp Met Tyr Leu Glu Gly Gly
                835                 840                 845

Gln Tyr Met Glu Lys Gly Thr Ile Tyr Asn Pro Val Ile Ser Ala Leu
                850                 855                 860

Leu Lys Ala Arg Ile Lys Tyr Val Ser Gly Gln Thr Met Ala Thr
865                 870                 875                 880

Asp Ser Ser Gly Lys Asp Leu Lys Asp Gly Glu Thr Asp Leu Leu Thr
                885                 890                 895
```

-continued

```
Ser Val Arg Phe Gly Lys Gly Ile Met Thr Ser Asp Gln Thr Thr Thr
            900                 905                 910

Gln Asp Asn Ser Gln Asp Tyr Lys Asn Gln Gly Ile Gly Val Ile Val
            915                 920                 925

Gly Asn Asn Pro Asp Leu Lys Leu Asn Asn Asp Lys Thr Ile Thr Leu
            930                 935                 940

His Met Gly Lys Ala His Lys Asn Gln Leu Tyr Arg Ala Leu Val Leu
945                 950                 955                 960

Ser Asn Asp Ser Gly Ile Asp Val Tyr Asp Ser Asp Lys Ala Pro
            965                 970                 975

Thr Leu Arg Thr Asn Asp Asn Gly Asp Leu Ile Phe His Lys Thr Asn
            980                 985                 990

Thr Phe Val Lys Gln Asp Gly Thr Ile Ile Asn Tyr Glu Met Lys Gly
            995                 1000                1005

Ser Leu Asn Ala Leu Ile Ser Gly Tyr Leu Gly Val Trp Val Pro Val
            1010                1015                1020

Gly Ala Ser Asp Ser Gln Asp Ala Arg Thr Val Ala Thr Glu Ser Ser
025                 1030                1035                1040

Ser Ser Asn Asp Gly Ser Val Phe His Ser Asn Ala Ala Leu Asp Ser
            1045                1050                1055

Asn Val Ile Tyr Glu Gly Phe Ser Asn Phe Gln Ala Met Pro Thr Ser
            1060                1065                1070

Pro Glu Gln Ser Thr Asn Val Val Ile Ala Thr Lys Ala Asn Leu Phe
            1075                1080                1085

Lys Glu Leu Gly Ile Thr Ser Phe Glu Leu Ala Pro Gln Tyr Arg Ser
            1090                1095                1100

Ser Gly Asp Thr Asn Tyr Gly Gly Met Ser Phe Leu Asp Ser Phe Leu
105                 1110                1115                1120

Asn Asn Gly Tyr Ala Phe Thr Asp Arg Tyr Asp Leu Gly Phe Asn Lys
            1125                1130                1135

Ala Asp Gly Asn Pro Asn Pro Thr Lys Tyr Gly Thr Asp Gln Asp Leu
            1140                1145                1150

Arg Asn Ala Ile Glu Ala Leu His Lys Asn Gly Met Gln Ala Ile Ala
            1155                1160                1165

Asp Trp Val Pro Asp Gln Ile Tyr Ala Leu Pro Gly Lys Glu Val Val
            1170                1175                1180

Thr Ala Thr Arg Val Asp Glu Arg Gly Asn Gln Leu Lys Asp Thr Asp
185                 1190                1195                1200

Phe Val Asn Leu Leu Tyr Val Ala Asn Thr Lys Ser Ser Gly Val Asp
            1205                1210                1215

Tyr Gln Ala Lys Tyr Gly Gly Glu Phe Leu Asp Lys Leu Arg Glu Glu
            1220                1225                1230

Tyr Pro Ser Leu Phe Lys Gln Asn Gln Val Ser Thr Gly Gln Pro Ile
            1235                1240                1245

Asp Ala Ser Thr Lys Ile Lys Gln Trp Ser Ala Lys Tyr Met Asn Gly
            1250                1255                1260

Thr Asn Ile Leu His Arg Gly Ala Tyr Tyr Val Leu Lys Asp Trp Ala
265                 1270                1275                1280

Thr Asn Gln Tyr Phe Asn Ile Ala Lys Thr Asn Glu Val Phe Leu Pro
            1285                1290                1295

Leu Gln Leu Gln Asn Lys Asp Ala Gln Thr Gly Phe Ile Ser Asp Ala
            1300                1305                1310
```

-continued

Ser Gly Val Lys Tyr Tyr Ser Ile Ser Gly Tyr Gln Ala Lys Asp Thr
    1315                1320                1325

Phe Ile Glu Asp Gly Asn Gly Asn Trp Tyr Tyr Phe Asp Lys Asp Gly
    1330                1335                1340

Tyr Met Val Arg Ser Gln Gln Gly Glu Asn Pro Ile Arg Thr Val Glu
345                 1350                1355                1360

Thr Ser Val Asn Thr Arg Asn Gly Asn Tyr Tyr Phe Met Pro Asn Gly
    1365                1370                1375

Val Glu Leu Arg Lys Gly Phe Gly Thr Asp Asn Ser Gly Asn Val Tyr
            1380                1385                1390

Tyr Phe Asp Asp Gln Gly Lys Met Val Arg Asp Lys Tyr Ile Asn Asp
            1395                1400                1405

Asp Ala Asn Asn Phe Tyr His Leu Asn Val Asp Gly Thr Met Ser Arg
    1410                1415                1420

Gly Leu Phe Lys Phe Asp Ser Asp Thr Leu Gln Tyr Phe Ala Ser Asn
425                 1430                1435                1440

Gly Val Gln Ile Lys Asp Ser Tyr Ala Lys Asp Ser Lys Gly Asn Lys
            1445                1450                1455

Tyr Tyr Phe Asp Ser Ala Thr Gly Asn Asn Asp Thr Gly Lys Ala Gln
            1460                1465                1470

Thr Trp Asp Gly Asn Gly Tyr Tyr Ile Thr Ile Asp Ser Asp Ala Asn
    1475                1480                1485

Asn Thr Ile Gly Val Asn Thr Asp Tyr Thr Ala Tyr Ile Thr Ser Ser
    1490                1495                1500

Leu Arg Glu Asp Gly Leu Phe Ala Asn Ala Pro Tyr Gly Val Val Thr
505                 1510                1515                1520

Lys Asp Gln Asn Gly Asn Asp Leu Lys Trp Gln Tyr Ile Asn His Thr
            1525                1530                1535

Lys Gln Tyr Glu Gly Gln Gln Val Gln Val Thr Arg Gln Tyr Thr Asp
            1540                1545                1550

Ser Lys Gly Val Ser Trp Asn Leu Ile Thr Phe Ala Gly Gly Asp Leu
    1555                1560                1565

Gln Gly Gln Arg Leu Trp Val Asp Ser Arg Ala Leu Thr Met Thr Pro
    1570                1575                1580

Phe Lys Thr Met Asn Gln Ile Ser Phe Ile Ser Tyr Ala Asn Arg Asn
585                 1590                1595                1600

Asp Gly Leu Phe Leu Asn Ala Pro Tyr Gln Val Lys Gly Tyr Gln Leu
            1605                1610                1615

Ala Gly Met Ser Asn Gln Tyr Lys Gly Gln Gln Val Thr Ile Ala Gly
            1620                1625                1630

Val Ala Asn Val Ser Gly Lys Asp Trp Ser Leu Ile Ser Phe Asn Gly
    1635                1640                1645

Thr Gln Tyr Trp Ile Asp Ser Gln Ala Leu Asn Thr Asn Phe Thr His
    1650                1655                1660

Asp Met Asn Gln Lys Val Phe Val Asn Thr Thr Ser Asn Leu Asp Gly
665                 1670                1675                1680

Leu Phe Leu Asn Ala Pro Tyr Arg Gln Pro Gly Tyr Lys Leu Ala Gly
            1685                1690                1695

Leu Ala Lys Asn Tyr Asn Asn Gln Thr Val Thr Val Ser Gln Gln Tyr
            1700                1705                1710

Phe Asp Asp Gln Gly Thr Val Trp Ser Gln Val Val Leu Gly Gly Gln
    1715                1720                1725

```
Thr Val Trp Val Asp Asn His Ala Leu Ala Gln Met Gln Val Ser Asp
       1730                1735                1740

Thr Asp Gln Gln Leu Tyr Val Asn Ser Asn Gly Arg Asn Asp Gly Leu
745                 1750                1755                1760

Phe Leu Asn Ala Pro Tyr Arg Gly Gln Gly Ser Gln Leu Ile Gly Met
                1765                1770                1775

Thr Ala Asp Tyr Asn Gly Gln His Val Gln Val Thr Lys Gln Gly Gln
            1780                1785                1790

Asp Ala Tyr Gly Ala Gln Trp Arg Leu Ile Thr Leu Asn Asn Gln Gln
        1795                1800                1805

Val Trp Val Asp Ser Arg Ala Leu Ser Thr Thr Ile Met Gln Ala Met
    1810                1815                1820

Asn Asp Asn Met Tyr Val Asn Ser Ser Gln Arg Thr Asp Gly Leu Trp
825                 1830                1835                1840

Leu Asn Ala Pro Tyr Thr Met Ser Gly Ala Lys Trp Ala Gly Asp Thr
                1845                1850                1855

Arg Ser Ala Asn Gly Arg Tyr Val His Ile Ser Lys Ala Tyr Ser Asn
            1860                1865                1870

Glu Val Gly Asn Thr Tyr Tyr Leu Thr Asn Leu Asn Gly Gln Ser Thr
        1875                1880                1885

Trp Ile Asp Lys Arg Ala Phe Thr Val Thr Phe Asp Gln Val Val Ala
    1890                1895                1900

Leu Asn Ala Thr Ile Val Ala Arg Gln Arg Pro Asp Gly Met Phe Lys
905                 1910                1915                1920

Thr Ala Pro Tyr Gly Glu Ala Gly Ala Gln Phe Val Asp Tyr Val Thr
                1925                1930                1935

Asn Tyr Asn Gln Gln Thr Val Pro Val Thr Lys Gln His Ser Asp Ala
            1940                1945                1950

Gln Gly Asn Gln Trp Tyr Leu Ala Thr Val Asn Gly Thr Gln Tyr Trp
        1955                1960                1965

Ile Asp Gln Arg Ser Phe Ser Pro Val Val Thr Lys Val Val Asp Tyr
    1970                1975                1980

Gln Ala Lys Ile Val Pro Arg Thr Thr Arg Asp Gly Val Phe Ser Gly
985                 1990                1995                2000

Ala Pro Tyr Gly Glu Val Asn Ala Lys Leu Val Asn Met Ala Thr Ala
                2005                2010                2015

Tyr Gln Asn Gln Val Val His Ala Thr Gly Glu Tyr Thr Asn Ala Ser
            2020                2025                2030

Gly Ile Thr Trp Ser Gln Phe Ala Leu Ser Gly Gln Glu Asp Lys Leu
        2035                2040                2045

Trp Ile Asp Lys Arg Ala Leu Gln Ala
    2050                2055

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: artificial
      sequence

<400> SEQUENCE: 3
actgcggccg catgccattt acagaaaaag                                      30

<210> SEQ ID NO 4
<211> LENGTH: 30
```

```
<212> TYPE: DNA
<213> ORGANISM: Artificial Sequence
<220> FEATURE:
<223> OTHER INFORMATION: Description of Artificial Sequence: artificial
      sequence

<400> SEQUENCE: 4
actgctcgag ttatgctgac acagcatttc                                           30

<210> SEQ ID NO 5
<211> LENGTH: 7
<212> TYPE: PRT
<213> ORGANISM: Leuconostoc mesenteroides

<400> SEQUENCE: 5

Lys Thr Asn Glu Val Phe Leu
  1               5

<210> SEQ ID NO 6
<211> LENGTH: 7
<212> TYPE: PRT
<213> ORGANISM: Leuconostoc mesenteroides

<400> SEQUENCE: 6

Lys Phe Asp Ser Asp Arg Leu
  1               5

<210> SEQ ID NO 7
<211> LENGTH: 19
<212> TYPE: PRT
<213> ORGANISM: Leuconostoc mesenteroides

<400> SEQUENCE: 7

Lys Asn Met Gln Asp Thr Phe Thr Phe Asp Gln Leu Ala Gln Gly Met
  1               5                  10                  15

Glu Phe Tyr

<210> SEQ ID NO 8
<211> LENGTH: 15
<212> TYPE: PRT
<213> ORGANISM: Leuconostoc mesenteroides

<400> SEQUENCE: 8

Lys Ser Thr Glu Trp Leu Arg Asp Ala Ile Asp Leu Phe Val Lys
  1               5                  10                  15

<210> SEQ ID NO 9
<211> LENGTH: 22
<212> TYPE: PRT
<213> ORGANISM: Leuconostoc mesenteroides

<400> SEQUENCE: 9

Lys Gly Ser Glu Phe Leu Leu Ala Asn Asp Ile Asp Asn Ser Asn Pro
  1               5                  10                  15

Ile Val Gln Ala Glu Gln
                20

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: artificial
      sequence
```

-continued

```
<400> SEQUENCE: 10
ytgrtcraan gtraangtrt cytgcatrtt ytt                              33

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: artificial
      sequence

<400> SEQUENCE:    11 gaygcnathg ayytnttygt naar                                       24

<210> SEQ ID NO 12
<211> LENGTH: 837
<212> TYPE: DNA
<213> ORGANISM: Leuconostoc mesenteroides

<400> SEQUENCE: 12
gatgcaattg atagttttgt gaagacgcaa gctaattgga ataagcaaac agaagatgaa    60
gctttcgatg gtttgcagtg gcttcaaggg ggattcctag cttatcaaga tgattcacat   120
cggacgccga atactgattc aggaaataac agaaaactag gacgtcaacc aattaatatc   180
gatggttcga agatacaac tgatggtaaa ggctctgaat tcttattagc taacgatatt   240
gacaactcaa atccgattgt tcaagctgag caattaaact ggctacacta tttaatgaat   300
tttggtagta ttacaggtaa taatgacaat gcgaattttg atggcattcg tgtagatgct   360
gttgataatg ttgatgctga tttactaaaa atagctggcg attattttaa agctctatat   420
ggtacagata aaagcgacgc caatgccaat aagcatttgt ctattttaga agactggaac   480
ggtaaagatc tcagtatgt taatcaacag ggcaatgcgc aattaacaat ggattacaca   540
gttacttcac agtttggcaa ttctctaaca catggcgcca acaacaggag taacatgtgg   600
tatttcttag atactggcta ttatcttaat ggagatctta ataagaagat agtagataag   660
aaccgtccaa attctggcac tttggttaac agaattgcta attcaggtga tacaaaagtt   720
attccaaatt atagttttgt tagagcacat gattacgatg ctcaagatcc aattagaaaa   780
gccatgattg atcatggtat tattaaaaac atgcaggata ctttcacttt tgaccaa      837

<210> SEQ ID NO 13
<211> LENGTH: 2862
<212> TYPE: DNA
<213> ORGANISM: Leuconostoc mesenteroides

<400> SEQUENCE: 13
gatcaaatag atgctaccgt tatacgagac gttaaggatt atcccaatct agtcgttttg    60
cgtaccttgt cgaaagctta tggtctggca aacctgagaa tcggctatgg cgtcatgcag   120
gaaccacttt atcaggttat gcaggccgta cgtttaccat ataatttaaa tacctatcaa   180
atcacaggtg cagtagctgc ccttagtgat caactttatc tgcaatcagt tgttgctaag   240
gtgaagtctg aacgtgaaaa atttgaacaa ttttttgacga acaccagtt taagtattat   300 caatcacaaa ccaactttct ctggattaaa gttggtgatg cgaaacgtgt tggtgaggct   360
cttctgtcag aagggtatca aattaatgac cgcctaaatg ccgaatggat tcgcattgca   420
ttaggaactg tgtctgataa tgaggggatg cagcgcattt tattgaattg ttaaaaaata   480
gctaagagag tatgttcttc tcttacctat ttttattgt aattcctatt atttaatttt   540
```

-continued

```
gcatgacaat attaatagcg tgttacgatt ctactattta atgttaataa aattaataaa      600
tatggtatta tcttatatgg gtgatagatg caccaaatac tgtatcatgt ctggtcacat      660 gaaaggggaga ataattaatg aaacaacaag aaacagttac ccgtaaaaaa ctttataaat      720
ccggtaaggt ttgggttgca gcagctactg catttgcggt attggggtt tcaactgtaa       780 caacagtcca tgcggataca aattcgaatg tcgctgttaa gcaaataaat aatacaggaa      840
ccaatgattc tggcgaaaaa aaggtaccgg ttccatcaac taataatgat agtttgaagc      900
aaggaacaga tggttttggg tatgattcag acggcaatcg tgtcgatcag aagaccaatc      960
agattctgct tactgcggaa caacttaaaa aaaataacga aaaaaattta tcagtaatca     1020
gtgatgatac atcaaaaaaa gatgatgaaa atatttctaa gcagaccaaa attgctaatc     1080
aacaaacagt agatactgct aaaggcctga ctaccagtaa tttatctgat cccatcactg     1140
ggggtcacta tgaaaatcac aatggctact ttgttttatat agatgcttca ggaaaacaag     1200
taacaggttt gcaaaatatt gatggtaatt tacaatattt tgatgacaat ggatatcaag     1260
tcaagggatc cttccgagat gtcaacggca agcatatcta ttttgattca gtaacaggga     1320
aagctagttc aaatgttgat attgttaacg gtaaagctca aggatatgat gcgcaaggca     1380
accaattaaa gaaaagttat gtcgccgata gttctgggca aacttactat tttgatggta     1440
atggccaacc gttaatcggc ttgcaaacaa ttgatgggaa cctacaatat tttaaccaac     1500
aaggggttca ataaagggt ggtttccaag atgttaacaa taaacgtatt tattttgcac     1560
caaacacagg taatgccgtt gccaatactg aaataattaa cggtaaatta cagggggcgtg     1620 acgcaaatgg taaccaggta aagaatgcat ttagtaaaga tgttgcagga aatacatttt     1680
attttgacgc aaacggtgtg atgttaacag ggttgcaaac tatttcagga aagacatatt     1740
atcttgatga acaaggacac ctgagaaaaa attacgcggg aacattcaat aatcagttta     1800
tgtacttcga tgctgataca ggtgcgggta aacagcgat tgaatatcaa tttgatcaag     1860
gattggtatc acaagtaat gaaaatactc ctcacaatgc cgcaaagtct tatgataaaa      1920
gtagttttga aaatgttgat ggttacttaa cagcagatac atggtatcgt ccaaccgata     1980
ttttaaaaaa tggagatact tggacggcat ctaccgaaac tgatatgcgt ccgctttaa     2040 tgacatggtg gcctgacaaa caaacacaag caaattactt gaattttatg tctagtaaag     2100
gacttggtat aacgaccact tatacagcag ctacgtcaca aaaaacacta atgacgcag      2160 cctttgttat tcaaacagca attgaacaac aaatatcttt gaaaaaaagt actgagtggt     2220
tacgtgatgc aattgatagt tttgtgaaga cgcaagctaa ttggaataag caaacagaag     2280
atgaagcttt cgatggtttg cagtggcttc aagggggatt cctagcttat caagatgatt     2340
cacatcggac gccgaatact gattcaggaa ataacagaaa actaggacgt caaccaatta     2400
atatcgatgg ttcgaaagat acaactgatg gtaaaggctc tgaattctta ttagctaacg     2460
atattgacaa ctcaaatccg attgttcaag ctgagcaatt aaactggcta cactatttaa     2520
tgaattttgg tagtattaca ggtaataatg acaatgcgaa ttttgatggc attcgtgtag     2580
atgctgttga taatgttgat gctgatttac taaaaatagc tggcgattat tttaaagctc     2640
tatatggtac agataaaagc gacgccaatg ccaataagca tttgtctatt ttagaagact     2700
ggaacggtaa agatcctcag tatgttaatc aacagggcaa tgcgcaatta acaatggatt     2760
acacagttac ttcacagttt ggcaattctc taacacatgg cgccaacaac aggagtaaca     2820
tgtggtattt cttagatact ggctattatc ttaatggaga tc                       2862
```

<210> SEQ ID NO 14
<211> LENGTH: 3970
<212> TYPE: DNA
<213> ORGANISM: Leuconostoc mesenteroides

<400> SEQUENCE: 14

| | | | | | | |
|---|---|---|---|---|---|---|
| gatcaaggat | tggtatcaca | aagtaatgaa | atactcctc | acaatgccgc | aaagtcttat | 60 |
| gataaaagta | gttttgaaaa | tgttgatggt | tacttaacag | cagatacatg | gtatcgtcca | 120 |
| accgatattt | taaaaaatgg | agatacttgg | acggcatcta | ccgaaactga | tatgcgtccg | 180 |
| cttttaatga | catggtggcc | tgacaaacaa | acacaagcaa | attacttgaa | ttttatgtct | 240 |
| agtaaaggac | ttggtataac | gaccacttat | acagcagcta | cgtcacaaaa | aacactaaat | 300 |
| gacgcagcct | ttgttattca | aacagcaatt | gaacaacaaa | tatctttgaa | aaaaagtact | 360 |
| gagtggttac | gtgatgcaat | tgatagtttt | gtgaagacgc | aagctaattg | gaataagcaa | 420 |
| acagaagatg | aagctttcga | tggtttgcag | tggcttcaag | ggggattcct | agcttatcaa | 480 |
| gatgattcac | atcggacgcc | gaatactgat | tcaggaaata | cagaaaact | aggacgtcaa | 540 |
| ccaattaata | tcgatggttc | gaaagataca | actgatggta | aaggctctga | attcttatta | 600 |
| gctaacgata | ttgacaactc | aaatccgatt | gttcaagctg | agcaattaaa | ctggctacac | 660 |
| tatttaatga | attttggtag | tattacaggt | aataatgaca | atgcgaattt | tgatggcatt | 720 |
| cgtgtagatg | ctgttgataa | tgttgatgct | gatttactaa | aaatagctgg | cgattatttt | 780 |
| aaagctctat | atggtacaga | taaaagcgac | gccaatgcca | ataagcattt | gtctattta | 840 |
| gaagactgga | acggtaaaga | tcctcagtat | gttaatcaac | agggcaatgc | gcaattaaca | 900 |
| atggattaca | cagttacttc | acagtttggc | aattctctaa | cacatggcgc | caacaacagg | 960 |
| agtaacatgt | ggtatttctt | agatactggc | tattatctta | atggagatct | taataagaag | 1020 |
| atagtagata | agaaccgtcc | aaattctggc | actttggtta | acagaattgc | taattcaggt | 1080 |
| gatacaaaag | ttattccaaa | ttatagtttt | gttagagcac | atgattacga | tgctcaagat | 1140 |
| ccaattagaa | aagccatgat | tgatcatggt | attattaaaa | acatgcagga | tactttcact | 1200 |
| tttgaccaac | tggctcaggg | aatggaattc | tactataaag | atcaagagaa | tccgtctggt | 1260 |
| ttcaaaaagt | ataacgatta | taacttacct | agtgcttatg | caatgttgtt | gactaataag | 1320 |
| gatactgtac | ctcgtgtcta | ttatggagat | atgtacctcg | aaggcgggca | atatatggaa | 1380 |
| aaagggacga | tttacaatcc | tgtcatttca | gcgttgctca | aagctagaat | aaaatatgtt | 1440 |
| tctggtgggc | aaacaatggc | taccgatagt | tctggaaaag | accttaaaga | tggcgaaact | 1500 |
| gatttgttaa | caagtgttcg | atttggtaaa | ggaattatga | catcagatca | aaccacaaca | 1560 |
| caagacaata | gccaagatta | taaaaatcaa | ggcatcggtg | tcattgttgg | taataaccct | 1620 |
| gaccttaagt | tgaacaatga | taagaccatt | accttgcata | tgggaaaggc | gcataagaat | 1680 |
| caactttacc | gtgccttagt | attatcaaat | gactcaggaa | ttgatgttta | tgatagtgat | 1740 |
| gataaagcac | caactttgag | aacaaatgac | aacggtgact | tgattttcca | taagacaaat | 1800 |
| acgtttgtga | agcaagatgg | aactattata | aattcgaaa | tgaagggatc | attaaatgct | 1860 |
| ttaattttcag | gttatttagg | tgtctggtg | ccagttggag | ctagtgattc | acaagatgct | 1920 |
| cgtacagtgg | caactgagtc | atcatcaagt | aatgatggtt | ctgtattcca | ttcaaatgct | 1980 |
| gcattagatt | ctaatgttat | atatgaaggc | ttttcaaact | ttcaagcgat | gccgacttct | 2040 |
| cctgagcaaa | gtacaaatgt | tgttattgca | acaaaggcta | acttatttaa | agaattaggt | 2100 |
| attactagtt | ttgagttagc | acctcaatat | aggtctagtg | gtgacactaa | ttacggtggc | 2160 |

-continued

| | | | |
|---|---|---|---|
| atgtcattct | tagattcttt | cttaaataat | ggttatgcat | ttaccgatag | atatgattta | 2220 |
| ggctttaaca | aagcagacgg | gaatcctaac | ccaacaaagt | atggaacaga | tcaagattta | 2280 |
| cgtaatgcaa | tagaggcatt | acacaaaaac | ggcatgcagg | ctatagctga | ttgggttcct | 2340 |
| gaccaaatat | atgctttacc | aggaaaggaa | gttgttaccg | ctactagagt | agacgaacgg | 2400 |
| ggaaatcaac | taaaagacac | agattttgtc | aacttactct | atgttgctaa | tactaaaagt | 2460 |
| agtggtgtgg | attatcaggc | aaagtatggc | ggcgaatttt | tagataaatt | aagagaagag | 2520 |
| tacccatcgt | tattcaaaca | gaaccaagta | tcgacaggtc | agccaattga | tgcttctaca | 2580 |
| aaaattaagc | aatggtcagc | taaatatatg | aatgggacca | atattttaca | tcgaggtgct | 2640 |
| tattatgttt | tgaaagactg | ggctactaac | cagtattta | acattgcaaa | aacgaatgaa | 2700 |
| gtatttttgc | cactacagtt | gcagaataaa | gatgcgcaaa | ctggtttcat | tagtgatgcc | 2760 |
| tccggtgtaa | aatattactc | aattagtggt | tatcaagcaa | aagatacttt | tattgaagat | 2820 |
| ggtaatggga | attggtatta | ctttgataaa | gatggttaca | tggtgcgttc | gcagcaagga | 2880 |
| gaaaatccta | aagaacagt | cgaaactagt | gtcaacacac | gaaacggtaa | ttattacttt | 2940 |
| atgccaaatg | gtgtcgagtt | gcgcaaaggc | tttggaacgg | ataatagtgg | taatgtctat | 3000 |
| tattttgatg | atcaaggtaa | gatggtgaga | gataaataca | ttaacgatga | tgctaataat | 3060 |
| ttttatcact | taaatgttga | tgggactatg | tctcgaggac | tatttaaatt | tgattctgat | 3120 |
| actctacagt | atttttgctag | taatggtgtc | caaataaaag | atagttatgc | gaaggatagt | 3180 |
| aaaggcaata | aatattattt | tgactcagct | acaggaaata | acgatactgg | gaaagcccaa | 3240 |
| acttgggatg | gtaatggcta | ctatattact | attgattctg | atgcgaacaa | tacaattggg | 3300 |
| gttaacacag | actacactgc | ctacatcact | agctcgctgc | gcgaagatgg | cttatttgct | 3360 |
| aacgcacctt | acggtgttgt | aacaaaagac | caaaatggta | acgatcttaa | gtggcagtat | 3420 |
| attaaccata | cgaaacagta | cgaagggcaa | caagtgcaag | tcacgcgtca | atacacagac | 3480 |
| agtaagggag | tcagctggaa | cttaattacc | tttgctggtg | gtgatttaca | aggacaaagg | 3540 |
| ctttgggtgg | atagtcgtgc | gttaactatg | acaccattta | aaacgatgaa | ccaaataagc | 3600 |
| ttcattagtt | atgctaaccg | caatgatggg | ttgttttga | atgcgccata | ccaagtcaag | 3660 |
| gggtatcaat | tagctgggat | gtccaaccaa | tacaagggcc | aacaagtgac | cattgctggg | 3720 |
| gtggcgaacg | tttctggaaa | agactggagt | ctgattagtt | ttaatgggac | acagtactgg | 3780 |
| attgatagtc | aggcattgaa | taccaattc | acacatgaca | tgaaccaaaa | ggtctttgtc | 3840 |
| aatacaacta | gtaatcttga | tgggttattc | ttaaatgcgc | cataccgtca | accgggttat | 3900 |
| aagttagccg | gtttggctaa | aaattacaac | aaccaaacgg | ttactgttag | tcaacagtac | 3960 |
| tttgatgatc | | | | | | 3970 |

<210> SEQ ID NO 15
<211> LENGTH: 1917
<212> TYPE: DNA
<213> ORGANISM: Leuconostoc mesenteroides

<400> SEQUENCE: 15

| | | | | | | |
|---|---|---|---|---|---|---|
| gatcaaggta | agatggtgag | agataaatac | attaacgatg | atgctaataa | tttttatcac | 60 |
| ttaaatgttg | atgggactat | gtctcgagga | ctatttaaat | ttgattctga | tactctacag | 120 |
| tatttttgcta | gtaatggtgt | ccaaataaaa | gatagttatg | cgaaggatag | taaaggcaat | 180 |
| aaatattatt | ttgactcagc | tacaggaaat | aacgatactg | ggaaagccca | aacttgggat | 240 |
| ggtaatggct | actatattac | tattgattct | gatgcgaaca | atacaattgg | ggttaacaca | 300 |

-continued

| | |
|---|---|
| gactacactg cctacatcac tagctcgctg cgcgaagatg gcttatttgc taacgcacct | 360 |
| tacggtgttg taacaaaaga ccaaaatggt aacgatctta agtggcagta tattaaccat | 420 |
| acgaaacagt acgaagggca acaagtgcaa gtcacgcgtc aatacacaga cagtaaggga | 480 |
| gtcagctgga acttaattac ctttgctggt ggtgatttac aaggacaaag ctttgggtg | 540 |
| gatagtcgtg cgttaactat gacaccattt aaaacgatga accaaataag cttcattagt | 600 |
| tatgctaacc gcaatgatgg gttgtttttg aatgcgccat accaagtcaa ggggtatcaa | 660 |
| ttagctggga tgtccaacca atacaagggc aacaagtgac ccattgctgg ggtggcgaac | 720 |
| gtttctggaa aagactggag tctgattagt tttaatggga cacagtactg gattgatagt | 780 |
| caggcattga ataccaattt cacacatgac atgaaccaaa aggtctttgt caatacaact | 840 |
| agtaatcttg atgggttatt cttaaatgcg ccataccgtc aaccgggtta taagttagcc | 900 |
| ggtttggcta aaaattacaa caaccaaacg gttactgtta gtcaacagta ctttgatgat | 960 |
| caaggcacgg tctggagtca ggttgtcctt ggggtcaga cggtctgggt tgataaccat | 1020 |
| gcattggcac agatgcaagt tagtgataca gaccaacagc tctatgtgaa tagcaatggt | 1080 |
| cggaatgatg ggttattctt gaatgcgcca tatcgtggtc aagggtcaca actgataggc | 1140 |
| atgacggcag attataatgg gcaacatgta caagtgacca agcaagggca agatgcctat | 1200 |
| ggtgcacaat ggcgtcttat tacgctaaat aatcaacagg tctgggttga tagtcgcgct | 1260 |
| ttgagcacaa caatcatgca agccatgaat gataatatgt atgtaaatag cagccaacgg | 1320 |
| acagatggct tgtggttaaa cgcacccttat acgatgagtg gggctaaatg ggctggtgat | 1380 |
| acacgttcag ctaatgggcg ctatgtccat atttcaaaag cttattcaaa cgaagtcggc | 1440 |
| aatacatatt acttgacgaa tttgaatggt caaagcacat ggattgacaa gcgggcgttt | 1500 |
| actgtgacct tcgatcaggt ggtggcatta aatgcaacga ttgtggcacg ccaacgacca | 1560 |
| gatgggatgt taagacagc accatatggt gaagcggggg cgcagtttgt cgattatgtg | 1620 |
| acaaactata accagcaaac cgtgccagta acaaagcaac attcagatgc tcagggggaat | 1680 |
| caatggtact agcgacagt gaatgggaca caatactgga ttgatcaacg gtcattttca | 1740 |
| ccagtagtaa cgaaggtggt tgattatcaa gctaagattg tgccacggac aacacgtgat | 1800 |
| ggtgtgttta gtggcgcacc ctatggggaa gtgaatgcta agctagttaa catggcaact | 1860 |
| gcgtatcaaa atcaagttgt ccatgcgaca ggggaatata cgaatgcttc agggatc | 1917 |

<210> SEQ ID NO 16
<211> LENGTH: 4066
<212> TYPE: DNA
<213> ORGANISM: Leuconostoc mesenteroides

<400> SEQUENCE: 16

| | |
|---|---|
| gatcttaagt ggcagtatat taaccatacg aaacagtacg aagggcaaca agtgcaagtc | 60 |
| acgcgtcaat acacagacag taagggagtc agctggaact taattacctt tgctggtggt | 120 |
| gatttacaag gacaaaggct ttgggtggat agtcgtgcgt taactatgac accatttaaa | 180 |
| acgatgaacc aaataagctt cattagttat gctaaccgca atgatgggtt gttttttgaat | 240 |
| gcgccatacc aagtcaaggg gtatcaatta gctgggatgt ccaaccaata caagggccaa | 300 |
| caagtgacca ttgctggggt ggcgaacgtt tctggaaaag actggagtct gattagtttt | 360 |
| aatgggacac agtactggat tgatagtcag gcattgaata ccaatttcac acatgacatg | 420 |
| aaccaaaagg tctttgtcaa tacaactagt aatcttgatg ggttattctt aaatgcgcca | 480 |
| taccgtcaac cgggttataa gttagccggt ttggctaaaa attacaacaa ccaaacggtt | 540 |

-continued

| | |
|---|---|
| actgttagtc aacagtactt tgatgatcaa ggcacggtct ggagtcaggt tgtccttggg | 600 |
| ggtcagacgg tctgggttga taaccatgca ttggcacaga tgcaagttag tgatacagac | 660 |
| caacagctct atgtgaatag caatggtcgg aatgatgggt tattcttgaa tgcgccatat | 720 |
| cgtggtcaag ggtcacaact gataggcatg acggcagatt ataatgggca acatgtacaa | 780 |
| gtgaccaagc aagggcaaga tgcctatggt gcacaatggc gtcttattac gctaaataat | 840 |
| caacaggtct gggttgatag tcgcgctttg agcacaacaa tcatgcaagc catgaatgat | 900 |
| aatatgtatg taaatagcag ccaacggaca gatggcttgt ggttaaacgc accttatacg | 960 |
| atgagtgggg ctaaatgggc tggtgataca cgttcagcta atgggcgcta tgtccatatt | 1020 |
| tcaaaagctt attcaaacga agtcggcaat acatattact tgacgaattt gaatggtcaa | 1080 |
| agcacatgga ttgacaagcg ggcgtttact gtgaccttcg atcaggtggt ggcattaaat | 1140 |
| gcaacgattg tggcacgcca acgaccagat gggatgttta agacagcacc atatggtgaa | 1200 |
| gcgggggcgc agtttgtcga ttatgtgaca aactataacc agcaaaccgt gccagtaaca | 1260 |
| aagcaacatt cagatgctca ggggaatcaa tggtacttag cgacagtgaa tgggacacaa | 1320 |
| tactggattg atcaacggtc atttttcacca gtagtaacga aggtggttga ttatcaagct | 1380 |
| aagattgtgc cacggacaac acgtgatggt gtgtttagtg gcgcaccta tggggaagtg | 1440 |
| aatgctaagc tagttaacat ggcaactgcg tatcaaaatc aagttgtcca tgcgacaggg | 1500 |
| gaatatacga atgcttcagg gatcacatgg agtcagttcg cgttaagcgg gcaagaagac | 1560 |
| aagctatgga ttgataagcg tgctttgcaa gcttaaggga aggattcgac aaaggagggt | 1620 |
| aacattatca gcggatggtg ttatcctcct ttcctgtact cagtatttcc caaataattg | 1680 |
| agacagtttc atgacaaatc aacaaaacta gtgtcaatgc ctcggttatg ggtaaaacta | 1740 |
| ctattagtta aagggttgtt gcataataat atcacattca atatattatg tattttatc | 1800 |
| tgattatgtg attttttgag atttggagcg aaaatgaata aagtaataat taataaagt | 1860 |
| ttctgtgttt tggtaatgag tttgttgtcg atatttctat tctcattaag agtagacgct | 1920 |
| cgttccaata gtggctacaa tcaaatatct tttaatcaac atgaaattgc ttatgcgcct | 1980 |
| tttagtcaag taccttggta tgcaactgtg aatgtcggaa tgtctgcaga caaaaataat | 2040 |
| atctatacag ctattgatat ggggccatag tatcaaggaa cttctttttt tccgtggtgg | 2100 |
| tatcaacatg ataattatga ttatcatgat ggttatcaac ttgcgattga caatcaatcg | 2160 |
| cttttcatag aaatggttga tacaggaagg tcgtcgtttg atgttattga gttgtataca | 2220 |
| ggtaaaaaag ttggttatgg aaaattcaca gcctataact ataacaagac ttcatggcag | 2280 |
| tttcaaatat ctttaaaggc gataagaaa atttaaata ataacatatc agaaaatgcg | 2340 |
| acaattagtt tgtacaatgg ttatctattc aaacaagccg aaagtatcac gtatgctggt | 2400 |
| tcaccaacag ggccatggtt acttgccggt attggtttgg tttttgctgg tgggggctat | 2460 |
| tacctgcaaa atcagcgccg aaaaacgatt acggcatcat caacaaacga ggtaacccat | 2520 |
| gcttaataat gctgttatta ttggtctaat tattatttgg gtctatgtat tatctgttct | 2580 |
| gaagcgtgct aaaacggatg cgtttttattt tttggctggc agcgcaggct tgttcgtcat | 2640 |
| tcttcttttta tggagtaaac cttatggtgt tggttgtttt cgaccattc tcacttggtc | 2700 |
| ggccggggtt gttggtcatc tcactggctt atttgatact ttctatgcgt cacatgttat | 2760 |
| tcaggttgtg gcgaatcatc ataccagcat tttattggtt gattatgaat gttcaggcat | 2820 |
| tattgaaaca acggcatttt ggggattaat tgccttttat cctgtgtatg atgcacaaaa | 2880 |
| gcggttaatg ttggcgctta ttggggcatt atggtttttc cttgcaaata cgttacgact | 2940 |

```
atcttttgtt gcagttgtaa tttattattt tggcgatggc gcttttatg ttgctcattc    3000
aattatcgga cgcctgttgt tctattcaat tgtaatcttg ctttattatc tagtcttcat    3060
aaagggggcaa cttgttaatc aaatgctcaa aaaacaggga taaactatgt cattttattt    3120
acatcaattt acttatcagt taggttttg gttcacttgg ttgctcattc cgtttgttgt    3180
ggaaattttc ccagctatta tttcaatcta gttttgataa aaacatcaaa aaagcatcaa    3240
gtgatgcaag aaccattgaa attaccaatg gtatctattg tattacctat atataattca    3300
ggacaaacat taccagtg tattcagtcg attagtcaat caacctatcc aaaacaatta    3360
atccaaatta ttgccgtgaa taatcaaagc actgataaca gttttacagt gtttaatcag    3420
gctcaagctg atttcccaat acttagaatg cagtggatga acacagatca aggtaaagcg    3480
cgtgcactaa atgctgctat ttataatagt atggggcaat atattattaa tttggatact    3540
gatggttggt tagaacccaa tgccttaaaa cggtttgtgc tttatttga aaatcactca    3600
gaaattgatg tagcaactgg tacgattctg acacaaaaaa aaatgattca aaaaacgcaa    3660
agtaaatggc ttaaattgct acagttaaac gaatattttg agtatgcaca atcattctta    3720
tcaggccgta gtattgaaaa ccgtggtaat cgtttgttca caatgtcagg tgcattttca    3780
gcgttttagac gtgatgtatt agttcagaca tttatgtata atgttgacac ggttggtgaa    3840
gatactgata tgacattttca actgcgattc cgcctaggca agcgtattgg tttctgtgat    3900
gatgccatgt tttatgttga accaatatca ggttatagtg aactttattt acaacggcag    3960
cgttggcagc gtgggcaaat tgaagtcgca caaaattca tgcagaataa gttgagtgtc    4020
cgtcagattt ttactaactt tatgattagt cgattaatga ttgatc           4066

<210> SEQ ID NO 17
<211> LENGTH: 7387
<212> TYPE: DNA
<213> ORGANISM: Leuconostoc mesenteroides

<400> SEQUENCE: 17
gatcaaatag atgctaccgt tatacgagac gttaaggatt atcccaatct agtcgttttg      60
cgtaccttgt cgaaagctta tggtctggca aacctgagaa tcggctatgg cgtcatgcag     120
gaaccacttt atcaggttat gcaggccgta cgtttaccat ataatttaaa tacctatcaa     180
atcacaggtg cagtagctgc ccttagtgat caactttatc tgcaatcagt tgttgctaag     240
gtgaagtctg aacgtgaaaa atttgaacaa tttttgacga acaccagtt taagtattat     300
caatcacaaa ccaactttct ctggattaaa gttggtgatg cgaaacgtgt tggtgaggct     360
cttctgtcag aagggtatca aattaatgac cgcctaaatg ccgaatggat tcgcattgca     420
ttaggaactg tgtctgataa tgagggggatg cagcgcattt tattgaattg ttaaaaaata     480
gctaagagag tatgttcttc tcttacctat tttattttgt aattcctatt atttaatttt     540
gcatgacaat attaatagcg tgttacgatt ctactattta atgttaataa attaataaa     600
tatggtatta tcttatatgg gtgatagatg caccaaatac tgtatcatgt ctggtcacat     660
gaaagggaga ataattaatg aaacaacaag aaacagttac ccgtaaaaaa ctttataaat     720
ccggtaaggt ttgggttgca gcagctactg catttgcggt attgggggtt tcaactgtaa     780
caacagtcca tgcggataca aattcgaatg tcgctgttaa gcaaataaat aatacaggaa     840
ccaatgattc tggcgaaaaa aaggtaccgg ttccatcaac taataatgat agtttgaagc     900
aaggaacaga tggttttggg tatgattcag acggcaatcg tgtcgatcag aagaccaatc     960
agattctgct tactgcggaa caacttaaaa aaataacga aaaaaattta tcagtaatca    1020
```

```
gtgatgatac atcaaaaaaa gatgatgaaa atatttctaa gcagaccaaa attgctaatc      1080
aacaaacagt agatactgct aaaggcctga ctaccagtaa tttatctgat cccatcactg      1140
ggggtcacta tgaaaatcac aatggctact ttgtttatat agatgcttca ggaaaacaag      1200
taacaggttt gcaaaatatt gatggtaatt tacaatattt tgatgacaat ggatatcaag      1260
tcaagggatc cttccgagat gtcaacggca agcatatcta ttttgattca gtaacaggga      1320
aagctagttc aaatgttgat attgttaacg gtaaagctca aggatatgat gcgcaaggca      1380
accaattaaa gaaaagttat gtcgccgata gttctgggca aacttactat tttgatggta      1440
atggccaacc gttaatcggc ttgcaaacaa ttgatgggaa cctacaatat tttaaccaac      1500 aagggttca aataaagggt ggtttccaag atgttaacaa taaacgtatt tattttgcac      1560
caaacacagg taatgccgtt gccaatactg aaataattaa cggtaaatta caggggcgtg      1620
acgcaaatgg taaccaggta aagaatgcat ttagtaaaga tgttgcagga aatacattt       1680 attttgacgc aaacggtgtg atgttaacag ggttgcaaac tatttcagga agacatatt       1740 atcttgatga caaggacac ctgagaaaaa attacgcggg aacattcaat aatcagttta       1800
tgtacttcga tgctgataca ggtgcgggta aaacagcgat tgaatatcaa tttgatcaag      1860
gattggtatc acaaagtaat gaaaatactc ctcacaatgc cgcaaagtct tatgataaaa      1920
gtagttttga aaatgttgat ggttacttaa cagcagatac atggtatcgt ccaaccgata      1980 ttttaaaaa tggagatact tggacggcat ctaccgaaac tgatatgcgt ccgcttttaa       2040
tgacatggtg gcctgacaaa caaacacaag caaattactt gaattttatg tctagtaaag      2100
gacttggtat aacgaccact tatacagcag ctacgtcaca aaaaacacta aatgacgcag      2160
cctttgttat tcaaacagca attgaacaac aaatatcttt gaaaaaagt actgagtggt       2220 tacgtgatgc aattgatagt tttgtgaaga cgcaagctaa ttggaataag caaacagaag      2280
atgaagcttt cgatggtttg cagtggcttc aagggggatt cctagcttat caagatgatt      2340
cacatcggac gccgaatact gattcaggaa ataacagaaa actaggacgt caaccaatta      2400
atatcgatgg ttcgaaagat acaactgatg gtaaaggctc tgaattctta ttagctaacg      2460
atattgacaa ctcaaatccg attgttcaag ctgagcaatt aaactggcta cactatttaa      2520
tgaattttgg tagtattaca ggtaataatg acaatgcgaa ttttgatggc attcgtgtag      2580
atgctgttga taatgttgat gctgatttac taaaaatagc tggcgattat tttaaagctc      2640
tatatggtac agataaaagc gacgccaatg ccaataagca tttgtctatt ttagaagact      2700
ggaacggtaa agatcctcag tatgttaatc aacagggcaa tgcgcaatta acaatggatt      2760
acacagttac ttcacagttt ggcaattctc taacacatgg cgccaacaac aggagtaaca      2820
tgtggtattt cttagatact ggctattatc ttaatggaga tcttaataag aagatagtag      2880
ataagaaccg tccaaattct ggcactttgg ttaacagaat tgctaattca ggtgatacaa      2940
aagttattcc aaattatagt tttgttagag cacatgatta cgatgctcaa gatccaatta      3000
gaaaagccat gattgatcat ggtattatta aaaacatgca ggatactttc acttttgacc      3060
aactggctca gggaatggaa ttctactata agatcaaga gaatccgtct ggtttcaaaa       3120
agtataacga ttataactta cctagtgctt atgcaatgtt gttgactaat aaggatactg      3180
tacctcgtgt ctattatgga gatatgtacc tcgaaggcgg gcaatatatg gaaaagggga      3240
cgatttacaa tcctgtcatt tcagcgttgc tcaaagctag aataaaatat gtttctggtg      3300
ggcaaacaat ggctaccgat agttctggaa aagacccttaa agatggcgaa actgatttgt     3360
taacaagtgt tcgatttggt aaaggaatta tgacatcaga tcaaaccaca acacaagaca     3420
```

```
atagccaaga ttataaaaat caaggcatcg gtgtcattgt tggtaataac cctgacctta  3480
agttgaacaa tgataagacc attaccttgc atatgggaaa ggcgcataag aatcaacttt  3540
accgtgcctt agtattatca aatgactcag gaattgatgt ttatgatagt gatgataaag  3600
caccaacttt gagaacaaat gacaacggtg acttgatttt ccataagaca aatacgtttg  3660
tgaagcaaga tggaactatt ataaattacg aaatgaaggg atcattaaat gctttaattt  3720
caggttattt aggtgtctgg gtgccagttg gagctagtga ttcacaagat gctcgtacag  3780
tggcaactga gtcatcatca agtaatgatg gttctgtatt ccattcaaat gctgcattag  3840
attctaatgt tatatatgaa ggcttttcaa actttcaagc gatgccgact tctcctgagc  3900
aaagtacaaa tgttgttatt gcaacaaagg ctaacttatt taagaatta ggtattacta  3960
gttttgagtt agcacctcaa tataggtcta gtggtgacac taattacggt ggcatgtcat  4020
tcttagattc tttcttaaat aatggttatg catttaccga tagatatgat ttaggcttta  4080
acaaagcaga cgggaatcct aacccaacaa agtatggaac agatcaagat ttacgtaatg  4140
caatagaggc attacacaaa aacggcatgc aggctatagc tgattgggtt cctgaccaaa  4200
tatatgcttt accaggaaag gaagttgtta ccgctactag agtagacgaa cggggaaatc  4260
aactaaaaga cacagatttt gtcaacttac tctatgttgc taatactaaa agtagtggtg  4320
tggattatca ggcaaagtat ggcggcgaat ttttagataa attaagagaa gagtacccat  4380
cgttattcaa acagaaccaa gtatcgacag gtcagccaat tgatgcttct acaaaaatta  4440
agcaatggtc agctaaatat atgaatggga ccaatatttt acatcgaggt gcttattatg  4500
ttttgaaaga ctgggctact aaccagtatt ttaacattgc aaaaacgaat gaagtatttt  4560
tgccactaca gttgcagaat aaagatgcgc aaactggttt cattagtgat gcctccggtg  4620
taaaatatta ctcaattagt ggttatcaag caaaagatac ttttattgaa gatggtaatg  4680
ggaattggta ttactttgat aaagatggtt acatggtgcg ttcgcagcaa ggagaaaatc  4740
ctataagaac agtcgaaact agtgtcaaca cacgaaacgg taattattac tttatgccaa  4800
atggtgtcga gttgcgcaaa ggcттттggaa cggataatag tggtaatgtc tattattttg  4860
atgatcaagg taagatggtg agagataaat acattaacga tgatgctaat aatttttatc  4920
acttaaatgt tgatgggact atgtctcgag gactatttaa atttgattct gatactctac  4980
agtattttgc tagtaatggt gtccaaataa aagatagtta tgcgaaggat agtaaaggca  5040
ataaatatta ttttgactca gctacaggaa ataacgatac tgggaaagcc caaacttggg  5100
atggtaatgg ctactatatt actattgatt ctgatgcgaa caatacaatt ggggttaaca  5160
cagactacac tgcctacatc actagctcgc tgcgcgaaga tggcttattt gctaacgcac  5220
cttacggtgt tgtaacaaaa gaccaaaatg gtaacgatct aagtggcag tatattaacc  5280
atacgaaaca gtacgaaggg caacaagtgc aagtcacgcg tcaatacaca gacagtaagg  5340
gagtcagctg gaacttaatt acctttgctg gтggтgaтттt acaaggacaa aggctttggg  5400
tggatagtcg tgcgttaact atgacaccat taaaacgat gaaccaaata agcttcatta  5460
gttatgctaa ccgcaatgat gggttgtttt tgaatgcgcc ataccaagtc aaggggtatc  5520
aattagctgg gatgtccaac caatacaagg gccaacaagt gaccattgct gggtggcga  5580
acgtttctgg aaaagactgg agtctgatta gttttaatgg gacacagtac tggattgata  5640
gtcaggcatt gaataccaat ttcacacatg acatgaacca aaaggtcttt gtcaatacaa  5700
ctagtaatct tgatgggtta ttcttaaatg cgccataccg tcaaccgggt tataagttag  5760
ccggtttggc taaaaattac aacaaccaaa cggttactgt tagtcaacag tactttgatg  5820
```

-continued

```
atcaaggcac ggtctggagt caggttgtcc ttgggggtca gacggtctgg gttgataacc    5880
atgcattggc acagatgcaa gttagtgata cagaccaaca gctctatgtg aatagcaatg    5940
gtcggaatga tgggttattc ttgaatgcgc catatcgtgg tcaagggtca caactgatag    6000
gcatgacggc agattataat gggcaacatg tacaagtgac caagcaaggg caagatgcct    6060
atggtgcaca atgcgtctt attacgctaa ataatcaaca ggtctggggtt gatagtcgcg    6120 ctttgagcac aacaatcatg caagccatga atgataatat gtatgtaaat agcagccaac    6180
ggacagatgg cttgtggtta aacgcaccct atacgatgag tggggctaaa tgggctggtg    6240
atacacgttc agctaatggg cgctatgtcc atatttcaaa agcttattca aacgaagtcg    6300
gcaatacata ttacttgacg aatttgaatg gtcaaagcac atggattgac aagcgggcgt    6360
ttactgtgac cttcgatcag gtggtggcat taaatgcaac gattgtggca cgccaacgac    6420
cagatgggat gtttaagaca gcaccatatg gtgaagcggg ggcgcagttt gtcgattatg    6480
tgacaaacta taaccagcaa accgtgccag taacaaagca acattcagat gctcagggga    6540
atcaatggta cttagcgaca gtgaatggga cacaatactg gattgatcaa cggtcatttt    6600
caccagtagt aacgaaggtg gttgattatc aagctaagat tgtgccacgg acaacacgtg    6660
atggtgtgtt tagtggcgca ccctatgggg aagtgaatgc taagctagtt aacatggcaa    6720
ctgcgtatca aaatcaagtt gtccatgcga caggggaata tacgaatgct tcagggatca    6780
catggagtca gttcgcgtta agcgggcaag aagacaagct atggattgat aagcgtgctt    6840
tgcaagctta agggaaggat tcgacaaagg agggtaacat tatcagcgga tggtgttatc    6900
ctcctttcct gtactcagta tttcccaaat aattgagaca gtttcatgac aaatcaacaa    6960
aactagtgtc aatgcctcgg ttatggggta aactactatt agttaaaggg ttgttgcata    7020
ataatatcac attcaatata ttatgtattt ttatctgatt atgtgatttt ttgagatttg    7080
gagcgaaaat gaataaagta ataattaata aaagtttctg tgttttggta atgagtttgt    7140
tgtcgatatt tctattctca ttaagagtag acgctcgttc caatagtggc tacaatcaaa    7200
tatcttttaa tcaacatgaa attgcttatg cgccttttag tcaagtacct tggtatgcaa    7260
ctgtgaatgt cggaatgtct gcagacaaaa ataatatcta tacagctatt gatatggggc    7320
catagtatca aggaacttct ttttttccgt ggtggtatca acatgataat tatgattatc    7380
atgatgg                                                              7387
```

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: artificial
      sequence

<400> SEQUENCE: 18
gggcccgcta gcatgaaaca acaagaaaca gt                                  32

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: artificial
      sequence

<400> SEQUENCE: 19
cccggggtcg acctttgtcg aatccttccc                                     30

<210> SEQ ID NO 20
<211> LENGTH: 6204
<212> TYPE: DNA
<213> ORGANISM: Leuconostoc mesenteroides

<400> SEQUENCE: 20

| | | | | | |
|---|---|---|---|---|---|
| gctagcatga | aacaacaaga | aacagttacc | cgtaaaaaac | tttataaatc | cggtaaggtt | 60 |
| tgggttgcag | cagctactgc | atttgcggta | ttggggtttt | caactgtaac | aacagtccat | 120 |
| gcggatacaa | attcgaatgt | cgctgttaag | caaataaata | atacaggaac | caatgattct | 180 |
| ggcgaaaaaa | aggtaccggt | tccatcaact | aataatgata | gtttgaagca | aggaacagat | 240 |
| ggttttggt | atgattcaga | cggcaatcgt | gtcgatcaga | agaccaatca | gattctgctt | 300 |
| actgcggaac | aacttaaaaa | aaataacgaa | aaaaatttat | cagtaatcag | tgatgataca | 360 |
| tcaaaaaaag | atgatgaaaa | tatttctaag | cagaccaaaa | ttgctaatca | acaaacagta | 420 |
| gatactgcta | aaggcctgac | taccagtaat | ttatctgatc | ccatcactgg | gggtcactat | 480 |
| gaaaatcaca | atggctactt | tgtttatata | gatgcttcag | gaaaacaagt | aacaggtttg | 540 |
| caaaatattg | atggtaattt | acaatatttt | gatgacaatg | gatatcaagt | caagggatcc | 600 |
| ttccgagatg | tcaacggcaa | gcatatctat | tttgattcag | taacagggaa | agctagttca | 660 |
| aatgttgata | ttgttaacgg | taaagctcaa | ggatatgatg | cgcaaggcaa | ccaattaaag | 720 |
| aaaagttatg | tcgccgatag | ttctgggcaa | acttactatt | tgatggtaa | tggccaaccg | 780 |
| ttaatcggct | tgcaaacaat | tgatgggaac | ctacaatatt | ttaaccaaca | aggggttcaa | 840 |
| ataaagggtg | gtttccaaga | tgttaacaat | aaacgtattt | attttgcacc | aaacacaggt | 900 |
| aatgccgttg | ccaatactga | aataattaac | ggtaaattac | aggggcgtga | cgcaaatggt | 960 |
| aaccaggtaa | agaatgcatt | tagtaaagat | gttgcaggaa | atacatttta | ttttgacgca | 1020 |
| aacggtgtga | tgttaacagg | gttgcaaact | atttcaggaa | agacatatta | tcttgatgaa | 1080 |
| caaggacacc | tgagaaaaaa | ttacgcggga | acattcaata | atcagtttat | gtacttcgat | 1140 |
| gctgatacag | gtgcgggtaa | aacagcgatt | gaatatcaat | ttgatcaagg | attggtatca | 1200 |
| caaagtaatg | aaaatactcc | tcacaatgcc | gcaaagtctt | atgataaaag | tagttttgaa | 1260 |
| aatgttgatg | gttacttaac | agcagataca | tggtatcgtc | caaccgatat | tttaaaaaat | 1320 |
| ggagatactt | ggacggcatc | taccgaaact | gatatgcgtc | cgcttttaat | gacatggtgg | 1380 |
| cctgacaaac | aaaacaaagc | aaattacttg | aattttatgt | ctagtaaagg | acttggtata | 1440 |
| acgaccactt | atacagcagc | tacgtcacaa | aaaaactaa | atgacgcagc | ctttgttatt | 1500 |
| caaacagcaa | ttgaacaaca | aatatctttg | aaaaaaagta | ctgagtggtt | acgtgatgca | 1560 |
| attgatagtt | ttgtgaagac | gcaagctaat | tggaataagc | aaacagaaga | tgaagctttc | 1620 |
| gatggtttgc | agtggcttca | agggggattc | ctagcttatc | aagatgattc | acatcggacg | 1680 |
| ccgaatactg | attcaggaaa | taacagaaaa | ctaggacgtc | aaccaattaa | tatcgatggt | 1740 |
| tcgaaagata | caactgatgg | taaaggctct | gaattcttat | tagctaacga | tattgacaac | 1800 |
| tcaaatccga | ttgttcaagc | tgagcaatta | aactggctac | actatttaat | gaattttggt | 1860 |
| agtattacag | gtaataatga | caatgcgaat | tttgatggca | ttcgtgtaga | tgctgttgat | 1920 |
| aatgttgatg | ctgatttact | aaaaatagct | ggcgattatt | ttaaagctct | atatggtaca | 1980 |
| gataaaagcg | acgccaatgc | caataagcat | ttgtctatttt | tagaagactg | aacggtaaa | 2040 |
| gatcctcagt | atgttaatca | acagggcaat | gcgcaattaa | caatggatta | cacagttact | 2100 |
| tcacagtttg | gcaattctct | aacacatggc | gccaacaaca | ggagtaacat | gtggtatttc | 2160 |

-continued

```
ttagatactg gctattatct taatggagat cttaataaga agatagtaga taagaaccgt      2220
ccaaattctg gcactttggt taacagaatt gctaattcag gtgatacaaa agttattcca      2280
aattatagtt ttgttagagc acatgattac gatgctcaag atccaattag aaaagccatg      2340
attgatcatg gtattattaa aaacatgcag gatactttca cttttgacca actggctcag      2400
ggaatggaat tctactataa agatcaagag aatccgtctg gtttcaaaaa gtataacgat      2460
tataacttac ctagtgctta tgcaatgttg ttgactaata aggatactgt acctcgtgtc      2520
tattatggag atatgtacct cgaaggcggg caatatatgg aaaaagggac gatttacaat      2580
cctgtcattt cagcgttgct caaagctaga ataaaatatg tttctggtgg gcaaacaatg      2640
gctaccgata gttctggaaa agaccttaaa gatggcgaaa ctgatttgtt aacaagtgtt      2700
cgatttggta aaggaattat gacatcagat caaaccacaa cacaagacaa tagccaagat      2760
tataaaaatc aaggcatcgg tgtcattgtt ggtaataacc ctgaccttaa gttgaacaat      2820
gataagacca ttaccttgca tatgggaaag gcgcataaga atcaacttta ccgtgcctta      2880
gtattatcaa atgactcagg aattgatgtt tatgatagtg atgataaagc accaactttg      2940
agaacaaatg acaacggtga cttgattttc cataagacaa atacgtttgt gaagcaagat      3000
ggaactatta taaattacga aatgaaggga tcattaaatg ctttaatttc aggttatttta     3060 ggtgtctggg tgccagttgg agctagtgat tcacaagatg ctcgtacagt ggcaactgag      3120
tcatcatcaa gtaatgatgg ttctgtattc cattcaaatg ctgcattaga ttctaatgtt      3180
atatatgaag gcttttcaaa cttttcaagcg atgccgactt ctcctgagca aagtacaaat     3240
gttgttattg caacaaaggc taacttattt aaagaattag gtattactag ttttgagtta     3300
gcacctcaat ataggtctag tggtgacact aattacggtg gcatgtcatt cttagattct      3360
ttcttaaata tggttatgc atttaccgat agatatgatt taggcttta caaagcagac      3420 gggaatccta acccaacaaa gtatggaaca gatcaagatt tacgtaatgc aatagaggca      3480
ttacacaaaa acggcatgca ggctatagct gattgggttc ctgaccaaat atatgcttta      3540
ccaggaaagg aagttgttac cgctactaga gtagacgaac ggggaaatca actaaaagac      3600
acagattttg tcaacttact ctatgttgct aatactaaaa gtagtggtgt ggattatcag      3660
gcaaagtatg gcggcgaatt tttagataaa ttaagagaag agtacccatc gttattcaaa      3720
cagaaccaag tatcgacagg tcagccaatt gatgcttcta caaaaattaa gcaatggtca      3780
gctaaatata tgaatgggac caatattta catcgaggtg cttattatgt tttgaaagac      3840
tgggctacta accagtattt taacattgca aaaacgaatg aagtattttt gccactacag      3900
ttgcagaata aagatgcgca aactggtttc attagtgatg cctccggtgt aaaatattac      3960
tcaattagtg gttatcaagc aaaagatact tttattgaag atggtaatgg gaattggtat      4020
tactttgata agatggtta catggtgcgt tcgcagcaag gagaaaatcc tataagaaca      4080
gtcgaaacta gtgtcaacac acgaaacggt aattattact ttatgccaaa tggtgtcgag      4140
ttgcgcaaag gctttggaac ggataatagt ggtaatgtct attatttga tgatcaaggt      4200 aagatggtga gagataaata cattaacgat gatgctaata attttttatca cttaaatgtt      4260 gatgggacta tgtctcgagg actatttaaa tttgattctg atactctaca gtattttgct      4320
agtaatggtg tccaaataaa agatagttat gcgaaggata gtaaaggcaa taaatattat      4380
tttgactcag ctacaggaaa taacgatact gggaaagccc aaacttggga tggtaatggc      4440
tactatatta ctattgattc tgatgcgaac aatacaattg gggttaacac agactacact      4500
gcctacatca ctagctcgct gcgcgaagat ggcttatttg ctaacgcacc ttacggtgtt      4560
```

-continued

```
gtaacaaaag accaaaatgg taacgatctt aagtggcagt atattaacca tacgaaacag    4620
tacgaagggc aacaagtgca agtcacgcgt caatacacag acagtaaggg agtcagctgg    4680
aacttaatta cctttgctgg tggtgattta caaggacaaa ggctttgggt ggatagtcgt    4740
gcgttaacta tgacaccatt taaaacgatg aaccaaataa gcttcattag ttatgctaac    4800
cgcaatgatg ggttgttttt gaatgcgcca taccaagtca aggggtatca attagctggg    4860
atgtccaacc aatacaaggg ccaacaagtg accattgctg gggtggcgaa cgtttctgga    4920
aaagactgga gtctgattag ttttaatggg acacagtact ggattgatag tcaggcattg    4980
aataccaatt tcacacatga catgaaccaa aaggtctttg tcaatacaac tagtaatctt    5040
gatgggttat tcttaaatgc gccataccgt caaccgggtt ataagttagc cggtttggct    5100
aaaaattaca caaccaaac ggttactgtt agtcaacagt actttgatga tcaaggcacg     5160
gtctggagtc aggttgtcct tggggtcag acggtctggg ttgataacca tgcattggca     5220
cagatgcaag ttagtgatac agaccaacag ctctatgtga atagcaatgg tcggaatgat    5280
gggttattct tgaatgcgcc atatcgtggt caagggtcac aactgatagg catgacggca    5340
gattataatg ggcaacatgt acaagtgacc aagcaagggc aagatgccta tggtgcacaa    5400
tggcgtctta ttacgctaaa taatcaacag gtctgggttg atagtcgcgc tttgagcaca    5460
acaatcatgc aagccatgaa tgataatatg tatgtaaata gcagccaacg gacagatggc    5520
ttgtggttaa acgcaccta tacgatgagt ggggctaaat gggctggtga tacacgttca     5580
gctaatgggc gctatgtcca tatttcaaaa gcttattcaa acgaagtcgg caatacatat    5640
tacttgacga atttgaatgg tcaaagcaca tggattgaca gcgggcgtt tactgtgacc     5700 ttcgatcagg tggtggcatt aaatgcaacg attgtggcac gccaacgacc agatgggatg    5760
tttaagacag caccatatgg tgaagcgggg gcgcagtttg tcgattatgt gacaaactat    5820
aaccagcaaa ccgtgccagt aacaaagcaa cattcagatg ctcaggggaa tcaatggtac    5880
ttagcgacag tgaatgggac acaatactgg attgatcaac ggtcatttc accagtagta    5940 acgaaggtgg ttgattatca agctaagatt gtgccacgga caacacgtga tggtgtgttt    6000
agtggcgcac cctatgggga agtgaatgct aagctagtta acatggcaac tgcgtatcaa    6060
aatcaagttg tccatgcgac aggggaatat acgaatgctt cagggatcac atggagtcag    6120
ttcgcgttaa gcgggcaaga agacaagcta tggattgata agcgtgctt gcaagcttaa     6180 gggaaggatt cgacaaaggt cgac                                           6204
```

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: artificial
      sequence

<400> SEQUENCE: 21

Asp Thr Asn Ser Asn Val Ala
 1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: artificial
      sequence -continued

```
<400> SEQUENCE: 22

Met Lys Gln Gln Glu
  1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 23

Lys Lys Val Pro Val
  1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 24

Lys Asp Asp Glu Asn
  1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 25

Ile Asp Gly Asn Leu
  1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 26

Tyr Val Ala Asp Ser
  1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 27

His Leu Arg Lys Asn
  1               5

<210> SEQ ID NO 28
<211> LENGTH: 5
<212> TYPE: PRT
```

```
<213> ORGANISM: Artificial Sequence
<220> FEATURE:
<223> OTHER INFORMATION: Description of Artificial Sequence: artificial
      sequence

<400> SEQUENCE: 28

Asn Glu Asn Thr Pro
  1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 29

Asn Val Asp Gly Tyr
  1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 30

Asn Pro Asp Leu Lys
  1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 31

Ser Asn Asp Ser Gly
  1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 32

Asn Thr Phe Val Lys
  1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 33

Ile Ser Gly Tyr Leu
  1               5
```

```
<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 34

Ser Asn Ala Ala Leu
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 35

Arg Gln Tyr Thr Asp
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 36

Gln Leu Tyr Arg Ala
 1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 37

Asp Asp Lys Ala Pro
 1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 38

Thr Arg Gln Tyr Thr
 1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: artificial
      sequence
```

```
<400> SEQUENCE: 39

Ile Thr Phe Ala Gly
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 40

Asn Gln Tyr Lys Gly
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 41

Leu Phe Leu Asn Ala
 1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 42

Gln Val Ser Asp Thr
 1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 43

Leu Ile Thr Leu Asn
 1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 44

Gly Arg Tyr Val His
 1               5

<210> SEQ ID NO 45
<211> LENGTH: 5
<212> TYPE: PRT
```

```
<213> ORGANISM: Artificial Sequence
<220> FEATURE:
<223> OTHER INFORMATION: Description of Artificial Sequence: artificial
      sequence

<400> SEQUENCE: 45

Thr Ala Pro Tyr Gly
 1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 46

Val Val Asp Tyr Gln
 1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: artificial
      sequence

<400> SEQUENCE: 47

Leu Ser Gly Gln Glu
 1               5

<210> SEQ ID NO 48
<211> LENGTH: 26
<212> TYPE: DNA
<213> ORGANISM: Artificial Sequence

<400> SEQUENCE: 48
tctagactgc aaaatggcaa ctacta                                          26

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: artificial
      sequence

<400> SEQUENCE: 49
gtcgacggtt tcatttggag tagtta                                          26

<210> SEQ ID NO 50
<211> LENGTH: 276
<212> TYPE: DNA
<213> ORGANISM: Solanum tuberosum

<400> SEQUENCE: 50
atggcaacta ctaaatcttt tttaatttta ttttttatga tattagcaac tactagttca     60
acatgtgcta agttggaaga aatggttact gttctaagta ttgatggagg tggaattaag    120
ggaatcattc cagctatcat tctcgaattt cttgaaggac aacttcagga agtggacaat    180
aataaagatg caagacttgc agattacttt gatgtaattg gaggaacaag tacaggaggt    240
ttattgactg ctatgataac tactccaaat gaaacc                              276
```

```
<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: artificial
      sequence

<400> SEQUENCE: 51
gcgtactcta gacgtactcc gccatgacca c                                          31

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: artificial
      sequence

<400> SEQUENCE: 52
gcgtacgtcg acggccctga tgggtcccat                                            30

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence: artificial
      sequence

<400> SEQUENCE: 53
ggccgggtcg acgatacaaa ttcgaatgtc gctg                                       34

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: artificial
      sequence

<400> SEQUENCE: 54
ggccggctgc aggttaccct cctttgtcga atc                                        33
```